(12) United States Patent
Gerlach et al.

(10) Patent No.: US 7,615,549 B2
(45) Date of Patent: Nov. 10, 2009

(54) SUBSTITUTED PYRROLIDINONES, THEIR MANUFACTURE AND THEIR USE AS MEDICAMENTS

(75) Inventors: Kai Gerlach, Biberach (DE); Henning Priepke, Warthausen (DE); Roland Pfau, Biberach (DE); Wolfgang Wienen, Biberach (DE); Annette Schuler-Metz, Ulm (DE); Herbert Nar, Ochsenhausen (DE); Peter Kuehn, Alberweiler (DE); Georg Dahmann, Attenweiler (DE)

(73) Assignee: Boehringer Ingelheim International GmbH, Ingelheim (DE)

( * ) Notice: Subject to any disclaimer, the term of this patent is extended or adjusted under 35 U.S.C. 154(b) by 435 days.

(21) Appl. No.: 11/275,187

(22) Filed: Dec. 16, 2005

(65) Prior Publication Data

US 2006/0142263 A1   Jun. 29, 2006

(30) Foreign Application Priority Data

Dec. 24, 2004   (DE) ........................ 10 2004 062 544

(51) Int. Cl.
| | |
|---|---|
| A61K 31/55 | (2006.01) |
| A61K 31/5377 | (2006.01) |
| A61K 31/445 | (2006.01) |
| C07D 267/10 | (2006.01) |
| C07D 265/32 | (2006.01) |
| C07D 295/00 | (2006.01) |
| C07D 401/14 | (2006.01) |

(52) U.S. Cl. ..................... 514/211.03; 514/212.01; 514/217.03; 514/235.5; 514/237.5; 514/326; 540/488; 540/524; 544/146; 544/152; 544/173; 546/208

(58) Field of Classification Search ............. 540/488, 540/524; 544/146, 152, 173; 546/208; 514/211.03, 514/212.01, 217.03, 235.5, 237.5, 326
See application file for complete search history.

(56) References Cited

FOREIGN PATENT DOCUMENTS

| EP | 1571154 A1 | 9/2005 |
|---|---|---|
| WO | WO 03/053925 A1 | 7/2003 |
| WO | WO 2004/082687 A1 | 9/2004 |
| WO | WO 2005/111029 A1 | 11/2005 |

OTHER PUBLICATIONS

"Tautomer." Retrieved online via Internet Oct. 27, 2008: URL: http://en.wikipedia.org/wiki/Tautomer.*
Werner W.K.R. Mederski et al; Chlorothiophenecarboxamides as P1 surrogates of inhibitors of blood coagulation factor Xa; Bioorganic & Medicinal Chemistry Letters vol. 14 (2004) pp. 5817-5822; Elsevier Ltd.

* cited by examiner

Primary Examiner—Kamal A Saeed
Assistant Examiner—Samantha L Shterengarts
(74) Attorney, Agent, or Firm—Michael P. Morris; Alan R. Stempel; Edouard G. Lebel

(57) ABSTRACT

The present invention relates to new substituted pyrrolidinones of general formula

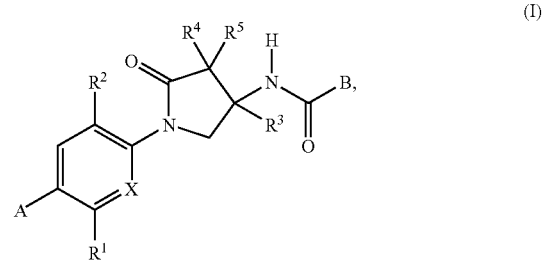

(I)

wherein A, X, B and $R^1$ to $R^9$ are as defined above, or a tautomer or salt thereof, particularly the physiologically acceptable salts thereof with inorganic or organic acids or bases, which have valuable properties.

11 Claims, No Drawings

SUBSTITUTED PYRROLIDINONES, THEIR MANUFACTURE AND THEIR USE AS MEDICAMENTS

This application claims priority to German Application DE 10 2004 062 544, filed on Dec. 24, 2004, which is incorporated herein in its entirety.

The present invention relates to new substituted pyrrolidinones of general formula

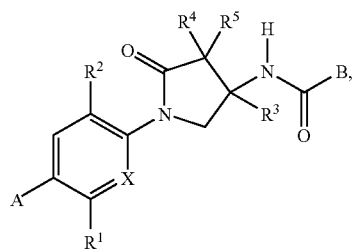

the tautomers, the enantiomers, the diastereomers, the mixtures thereof and the salts thereof, particularly the physiologically acceptable salts thereof with inorganic or organic acids or bases, which have valuable properties.

The compounds of the above general formula I as well as the tautomers, the enantiomers, the diastereomers, the mixtures thereof and the salts thereof, particularly the physiologically acceptable salts thereof with inorganic or organic acids or bases, and their stereoisomers have valuable pharmacological properties, particularly an antithrombotic activity and a factor Xa-inhibiting activity.

The present application relates to new compounds of the above general formula I, the preparation thereof, the pharmaceutical compositions containing the pharmacologically effective compounds, the preparation and use thereof.

A first embodiment of the present invention comprises those compounds of general formula I, wherein A denotes a group of general formula

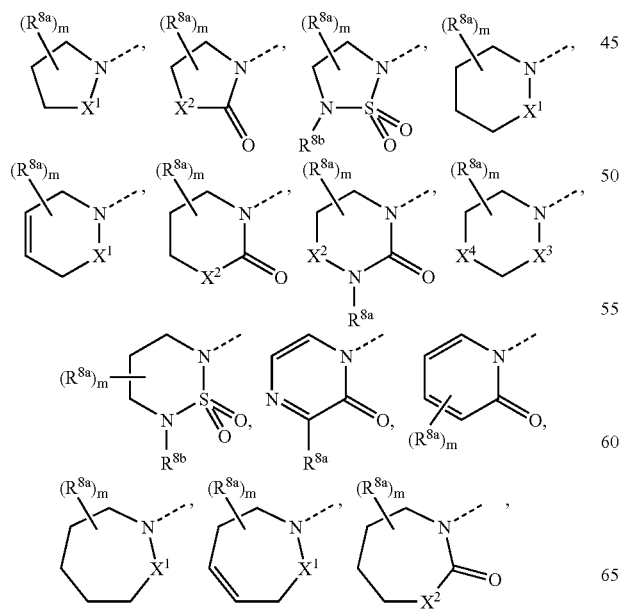

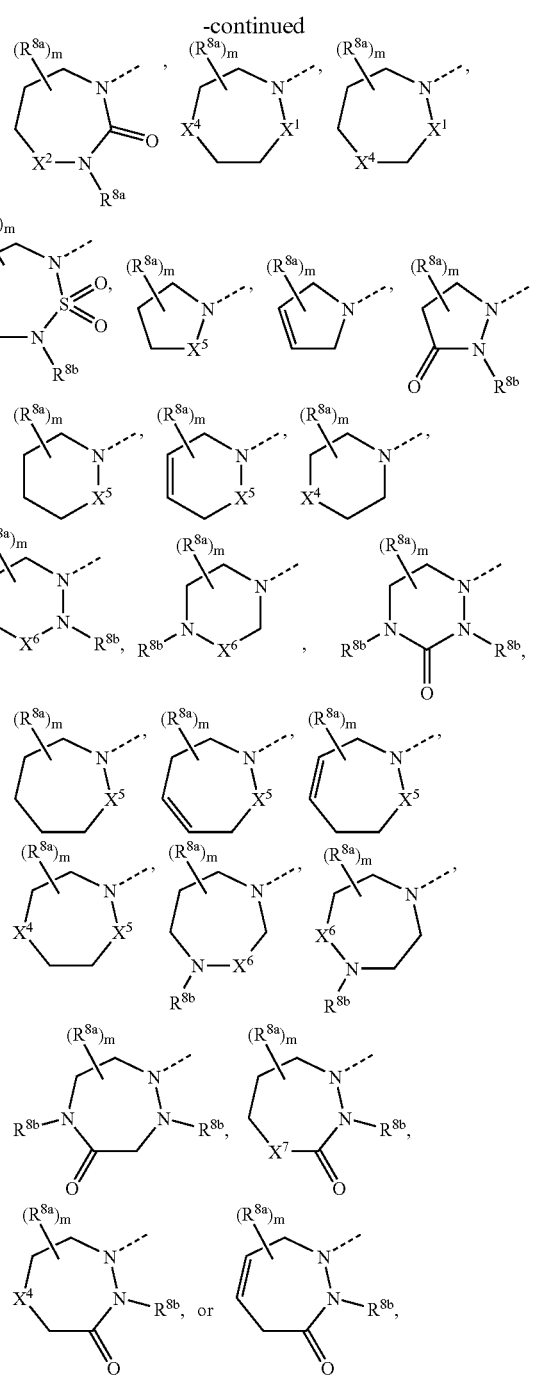

wherein m is the number 1 or 2, $R^{8a}$ in each case independently of one another denote a hydrogen or halogen atom or a $C_{1-5}$-alkyl, hydroxy, hydroxy-$C_{1-5}$- alkyl, $C_{1-5}$-alkoxy, $C_{1-5}$-alkoxy-$C_{1-5}$-alkyl, amino, $C_{1-5}$-alkylamino, di-($C_{1-5}$-alkyl)-amino, amino-$C_{1-5}$-alkyl, $C_{1-5}$-alkylamino-$C_{1-5}$-alkyl, di-($C_{1-5}$-alkyl)-amino-$C_{1-5}$-alkyl, aminocarbonyl, $C_{1-5}$-alkylaminocarbonyl, di-($C_{1-5}$-alkyl)-aminocarbonyl or $C_{1-5}$-alkylcarbonylamino group, while in the previously mentioned substituted 5- to 7-membered groups A the heteroatoms F, Cl, Br, O, or N optionally introduced with $R^{8a}$ as substituents are not separated by precisely one carbon atom from a heteroatom selected from among N, O and S, $R^{8b}$ each independently of one another denote a hydrogen atom or a $C_{1-5}$-alkyl group, $R^{8c}$ each independently of one another denote a hydrogen atom, a $C_{1-5}$-alkyl, $C_{1-5}$-alkylcarbonyl, $C_{1-5}$-alkyloxycarbonyl or $C_{1-5}$-alkylsulphonyl group, $X^1$ denotes a carbonyl, thiocarbonyl, C=$NR^{8c}$, C=N—$OR^{8c}$, C=N—$NO_2$, C=N—CN or sulphonyl group, $X^2$ denotes an oxygen atom or an —$NR^{8b}$ group, $X^3$ denotes a carbonyl, thiocarbonyl, C=$NR^{8c}$, C=N—$OR^{8c}$, C=N—$NO_2$, C=N—CN or sulphonyl group, $X^4$ denotes an oxygen or sulphur atom or an —$NR^{8c}$ group, $X^5$ denotes an oxygen atom or a —$CH_2$, —$CHR^{8a}$ or —$NR^{8c}$ group, $X^6$ denotes a carbonyl or sulphonyl group, $X^7$ denotes an oxygen atom, an —$NR^{8b}$ or methylene group, $R^1$ denotes a hydrogen or halogen atom, a $C_{1-3}$-alkyl or $C_{1-3}$-alkoxy group, while the hydrogen atoms of the $C_{1-3}$-alkyl or $C_{1-3}$-alkoxy group may optionally be wholly or partly replaced by fluorine atoms, a $C_{2-3}$-alkenyl, $C_{2-3}$-alkynyl, nitrile, nitro or amino group, $R^2$ denotes a hydrogen or halogen atom or a $C_{1-3}$-alkyl group, X denotes a nitrogen atom or a CH group, $R^3$ denotes a hydrogen atom or a $C_{1-3}$-alkyl group, $R^4$ and $R^5$ each independently of one another denote
  a hydrogen atom, a hydroxy group, an $OR^9$ group, a $C_{2-6}$-alkenyl or $C_{2-6}$-alkynyl group,
  a straight-chain or branched $C_{1-6}$-alkyl group,
    while the hydrogen atoms of the straight-chain or branched $C_{1-6}$-alkyl group may optionally be wholly or partly replaced by fluorine atoms, and which may optionally be substituted by a $C_{3-5}$-cycloalkyl group, a nitrile, hydroxy, a $C_{1-5}$-alkyloxy group, while the hydrogen atoms of the $C_{1-5}$-alkyloxy group may optionally be wholly or partly replaced by fluorine atoms, an allyloxy, propargyloxy, benzyloxy, $C_{1-5}$-alkylcarbonyloxy, $C_{1-5}$-alkyloxycarbonyloxy, carboxy-$C_{1-5}$-alkyloxy, $C_{1-5}$-alkyloxycarbonyl-$C_{1-5}$-alkyloxy, mercapto, $C_{1-5}$-alkylsulphanyl, $C_{1-5}$-alkylsulphonyl, carboxy, $C_{1-5}$-alkyloxycarbonyl, aminocarbonyl, $C_{1-5}$-alkylaminocarbonyl, di-($C_{1-5}$-alkyl)-aminocarbonyl, $C_{3-6}$-cycloalkyleneiminocarbonyl, aminosulphonyl, $C_{1-5}$-alkylaminosulphonyl, di-($C_{1-5}$-alkyl)-aminosulphonyl, $C_{3-6}$-cycloalkyleneiminosulphonyl, amino, $C_{1-5}$-alkylamino, di-($C_{1-5}$-alkyl)-amino, $C_{1-5}$-alkylcarbonylamino, $C_{1-5}$-alkylsulphonylamino, N-($C_{1-5}$-alkylsulphonyl)-$C_{1-5}$-alkylamino or $C_{3-6}$-cycloalkylcarbonylamino group,
    while the 6- to 7-membered cyclic groups of the $C_{3-6}$-cycloalkyleneiminocarbonyl group in the cyclic moiety a methylene group in the 4 position of a 6- or 7-membered cycloalkyleneimino group may be replaced by an oxygen or sulphur atom, by a carbonyl, sulphinyl, sulphonyl or —$NR^{8c}$ group and additionally a methylene group adjacent to an above-mentioned —$NR^{8c}$ group may be replaced by a carbonyl group,
  a phenyl, or heteroaryl group
    which may optionally be mono- to trisubstituted in the phenyl or heteroaryl moiety by identical or different substituents selected from among halogen atoms, $C_{1-5}$-alkyl, di-($C_{1-5}$-alkyl)-amino, hydroxy, $C_{1-5}$-alkyloxy, mono-, di- or trifluoromethoxy, carboxy- and $C_{1-5}$-alkyloxycarbonyl groups,
  a phenyl-$C_{1-5}$-alkyl or heteroaryl-$C_{1-5}$-alkyl group,
    which may optionally be mono- to trisubstituted in the phenyl or heteroaryl moiety by identical or different substituents selected from among halogen atoms, $C_{1-5}$-alkyl, di-($C_{1-5}$-alkyl)-amino, hydroxy, $C_{1-5}$-alkyloxy, mono-, di- or trifluoromethoxy, carboxy- and $C_{1-5}$-alkyloxycarbonyl groups, and which may optionally be substituted in the $C_{1-5}$-alkyl-moiety by a hydroxy, a $C_{1-5}$-alkyloxy group, while the hydrogen atoms of the $C_{1-5}$-alkyloxy group may optionally be wholly or partly replaced by fluorine atoms, an allyloxy, propargyloxy, benzyloxy, $C_{1-5}$-alkylcarbonyloxy, $C_{1-5}$-alkyloxycarbonyloxy, carboxy-$C_{1-5}$-alkyloxy, or a $C_{1-5}$-alkyloxycarbonyl-$C_{1-5}$-alkyloxy group;
  a 3- to 7-membered cycloalkyl, cycloalkyleneimino, cycloalkyl-$C_{1-5}$-alkyl or cycloalkyleneimino-$C_{1-3}$-alkyl group,
    wherein in 4- to 7-membered cyclic groups in the cyclic moiety a methylene group may optionally be replaced by an —N($R^{8c}$) group, an oxygen or sulphur atom or a —S(O) or —S(O)$_2$ group, or
    wherein in 4- to 7-membered cyclic groups in the cyclic moiety two adjacent methylene groups together may optionally be replaced by a —C(O)N($R^{8b}$) or —S(O)$_2$N($R^{8b}$) group, or
    wherein in 6- to 7-membered cyclic groups in the cyclic moiety three adjacent methylene groups together may optionally be replaced by a substituted —OC(O)N($R^{8b}$) or —N($R^{8b}$)C(O)N($R^{8b}$) or —N($R^{8b}$)S(O)$_2$N($R^{8b}$) group,
    with the proviso that a 3- to 7-membered cycloalkyl, cycloalkyleneimino, cycloalkyl-$C_{1-5}$-alkyl or cycloalkyleneimino-$C_{1-3}$-alkyl group as hereinbefore defined wherein two heteroatoms from the group oxygen and nitrogen are separated from one another by precisely one optionally substituted —$CH_2$ group, is excluded,
    while a 3- to 7-membered cycloalkyl, cycloalkyleneimino, cycloalkyl-$C_{1-5}$-alkyl or cycloalkyleneimino-$C_{1-3}$-alkyl group as hereinbefore defined may be substituted at one or two —$CH_2$ groups by one or two $C_{1-3}$-alkyl groups in each case,
  with the proviso that $R^4$ and $R^5$ may not simultaneously be defined as hydroxy or $OR^9$ groups, or $R^4$ and $R^5$ together with the carbon atom to which they are bound form a $C_{3-8}$-cycloalkyl or $C_{3-8}$-cycloalkenyl group,
  while one of the methylene groups of a $C_{4-8}$-cycloalkyl group may be replaced by an oxygen or sulphur atom or an —N($R^{8c}$), or a carbonyl, sulphinyl or sulphonyl group, and/or
  two directly adjacent methylene groups of a $C_{4-8}$-cycloalkyl group may together be replaced by a —C(O)N($R^{8b}$) or —S(O)$_2$N($R^{8b}$) group, and/or
  three directly adjacent methylene groups of a $C_{6-8}$-cycloalkyl group may together be replaced by a —OC(O)N($R^{8b}$), —N($R^{8b}$)C(O)N($R^{8b}$) or —N($R^{8b}$)S(O)$_2$N($R^{8b}$) group,
  while 1 to 3 carbon atoms of a $C_{3-8}$-cycloalkyl group may optionally be substituted independently of one another by in each case one or two identical or different halogen atoms or $C_{1-5}$-alkyl, nitrile, hydroxy, $C_{1-5}$-alkyloxy, $C_{1-5}$-alkylcarbonyloxy, carboxy-$C_{1-5}$-alkyl, $C_{1-5}$-alkyloxycarbonyl-$C_{1-5}$-alkyl, $C_{1-5}$-alkylsulphanyl, $C_{1-5}$- alkylsulphonyl, carboxy, $C_{1-5}$-alkyloxycarbonyl, aminocarbonyl, $C_{1-5}$-alkylaminocarbonyl, di-($C_{1-5}$-alkyl)-aminocarbonyl, $C_{3-6}$-cycloalkyleneiminocarbonyl, aminosulphonyl, $C_{1-5}$-alkylaminosulphonyl, di-($C_{1-5}$-alkyl)-aminosulphonyl, $C_{3-6}$-cycloalkyleneiminosulphonyl, amino, $C_{1-5}$-alkylamino, di-($C_{1-5}$-alkyl)-amino, $C_{1-5}$-alkylcarbonylamino, $C_{1-5}$-alkyl-sulphonylamino, N-($C_{1-5}$-alkylsulphonyl)-$C_{1-5}$-alkylamino or $C_{3-6}$-cycloalkylcarbonylamino groups, while 1 to 2 carbon atoms of a $C_{3-8}$-cycloalkenyl group may optionally be substituted independently of one another by in each case a $C_{1-5}$-alkyl, nitrile, carboxy-$C_{1-5}$-alkyl, $C_{1-5}$-alkyloxycarbonyl-$C_{1-5}$-alkyl, carboxy, $C_{1-5}$-alkyloxycarbonyl, aminocarbonyl, $C_{1-5}$-alkylaminocarbonyl, di-($C_{1-5}$-alkyl)-aminocarbonyl, $C_{3-6}$-cycloalkyleneiminocarbonyl, aminosulphonyl, $C_{1-5}$-alkylaminosulphonyl, di-($C_{1-5}$-alkyl)-aminosulphonyl, $C_{3-6}$-cycloalkyleneiminosulphonyl groups, and 1 to 2 carbon atoms of a $C_{4-8}$-cycloalkenyl group which are not bound by a double bond to another carbon atom, may optionally be substituted independently of one another by a fluorine atom or a hydroxy, $C_{1-5}$-alkyloxy, $C_{1-5}$-alkylcarbonyloxy, $C_{1-5}$-alkylsulphanyl, $C_{1-5}$-alkylsulphonyl, amino, $C_{1-5}$-alkylamino, di-($C_{1-5}$-alkyl)-amino, $C_{1-5}$-alkylcarbonylamino, $C_{1-5}$-alkylsulphonylamino, N-($C_{1-5}$-alkylsulphonyl)-$C_{1-5}$-alkylamino or $C_{3-6}$-cycloalkylcarbonyl-amino groups, with the proviso that a $C_{3-8}$-cycloalkyl or $C_{3-8}$-cycloalkenyl group of this kind formed from $R^4$ and $R^5$ together,
wherein two heteroatoms in the cyclic group selected from among oxygen and nitrogen are separated from one another by precisely one optionally substituted —$CH_2$ group, and/or
wherein one or both methylene groups of the cyclic group, which are directly attached to the carbon atom to which the groups $R^4$ and $R^5$ are bound, are replaced by a heteroatom selected from among oxygen, nitrogen and sulphur, and/or
wherein a substituent bound to the cyclic group, which is characterised in that a heteroatom selected from among oxygen, nitrogen, sulphur and halogen atom is bound directly to the cyclic group, is separated from another heteroatom selected from among oxygen, nitrogen and sulphur, with the exception of the sulphone group, by precisely one optionally substituted methylene group, and/or
wherein two oxygen atoms are joined together directly, is excluded, $R^9$ denotes a straight-chain or branched $C_{1-6}$-alkyl group,
while the hydrogen atoms of the straight-chain or branched $C_{1-6}$-alkyl group may optionally be wholly or partly replaced by fluorine atoms, and which may optionally be substituted by a $C_{3-5}$-cycloalkyl group, a hydroxy, a $C_{1-5}$-alkyloxy group, while the hydrogen atoms of the $C_{1-5}$-alkyloxy group may optionally be wholly or partly replaced by fluorine atoms, an allyloxy, propargyloxy, benzyloxy, $C_{1-5}$-alkylcarbonyloxy, $C_{1-5}$-alkyloxycarbonyloxy, carboxy-$C_{1-5}$-alkyloxy, $C_{1-5}$-alkyloxycarbonyl-$C_{1-5}$-alkyloxy, carboxy, $C_{1-5}$-alkyloxycarbonyl, aminocarbonyl, $C_{1-5}$-alkylaminocarbonyl, di-($C_{1-5}$-alkyl)-aminocarbonyl, $C_{3-6}$-cycloalkyleneiminocarbonyl, amino, $C_{1-5}$-alkylamino, di-($C_{1-5}$-alkyl)-amino, $C_{1-5}$-alkylcarbonylamino, $C_{1-5}$-alkylsulphonylamino, N-($C_{1-5}$-alkylsulphonyl)-$C_{1-5}$-alkylamino or $C_{3-6}$-cycloalkylcarbonylamino group,
while the 6- to 7-membered cyclic groups of the $C_{3-6}$-cycloalkyleneiminocarbonyl group in the cyclic moiety a methylene group in the 4 position of a 6- or 7-membered cycloalkyleneimino group may be replaced by an oxygen or sulphur atom, by a carbonyl, sulphinyl, sulphonyl or —$NR^{8c}$ group and additionally a methylene group adjacent to an above-mentioned —$NR^{8c}$ group may be replaced by a carbonyl group, with the proviso that the replacement of hydrogen atoms of the first carbon atom of the straight-chain or branched $C_{1-6}$-alkyl group by substituents from the group comprising oxygen, sulphur or nitrogen is excluded, a phenyl, heteroaryl, phenyl-$C_{1-5}$-alkyl or heteroaryl-$C_{1-5}$-alkyl group, which may optionally be mono- to trisubstituted in the phenyl or heteroaryl moiety by identical or different substituents selected from among halogen atoms, $C_{1-5}$-alkyl, di-($C_{1-5}$-alkyl)-amino, hydroxy, $C_{1-5}$-alkyloxy, mono-, di- or trifluoromethoxy, carboxy- and $C_{1-5}$-alkyloxycarbonyl groups, a 3- to 7-membered cycloalkyl, cycloalkyl-$C_{1-5}$-alkyl or cycloalkyleneimino-$C_{2-3}$-alkyl group,
wherein in 4- to 7-membered cyclic groups in the cyclic moiety a methylene group may optionally be replaced by an —$N(R^{8c})$ group, an oxygen or sulphur atom or a —$S(O)$ or —$S(O)_2$ group, or
wherein in 4- to 7-membered cyclic groups in the cyclic moiety two adjacent methylene groups together may optionally be replaced by a —$C(O)N(R^{8b})$ or —$S(O)_2N(R^{8b})$ group, or
wherein in 6- to 7-membered cyclic groups in the cyclic moiety three adjacent methylene groups together may optionally be replaced by a substituted —$OC(O)N(R^{8b})$ or —$N(R^{8b})C(O)N(R^{8b})$ or —$N(R^{8b})S(O)_2N(R^{8b})$ group,
with the proviso that a 3- to 7-membered cycloalkyl, cycloalkyl-$C_{1-5}$-alkyl or cycloalkyleneimino-$C_{2-3}$-alkyl group as hereinbefore defined wherein two heteroatoms from the group comprising oxygen and nitrogen are separated from one another by precisely one optionally substituted —$CH_2$ group, is excluded,
while a 3- to 7-membered cycloalkyl, cycloalkyl-$C_{1-5}$-alkyl or cycloalkyleneimino-$C_{2-3}$-alkyl group as hereinbefore defined may be substituted at one or two —$CH_2$ groups by one or two $C_{1-3}$-alkyl groups in each case, B denotes a group of general formula

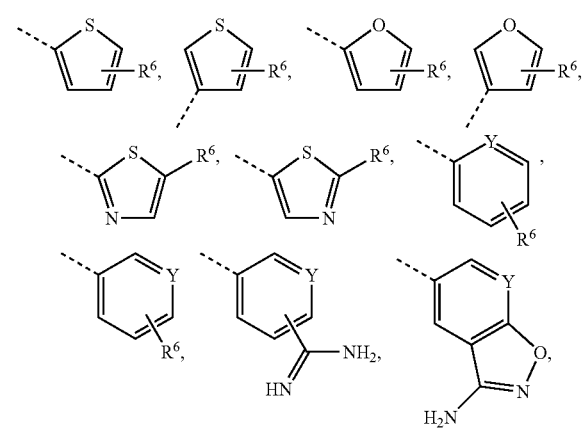

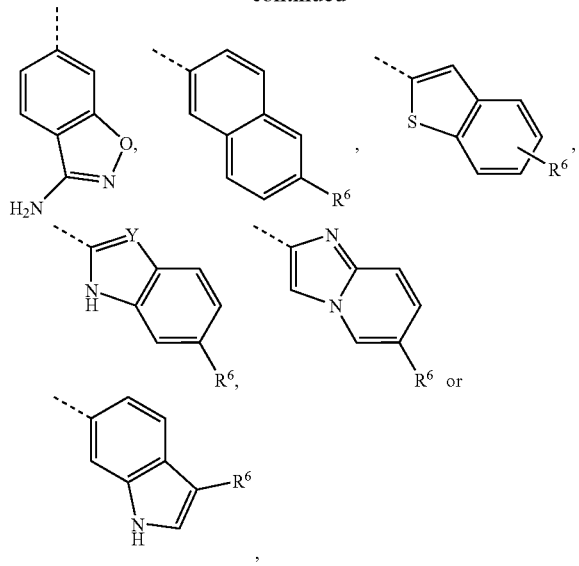

Y denotes a nitrogen atom or a CH group,

R⁶ denotes a hydrogen, a halogen atom, a nitrile group, a $C_{2-3}$-alkenyl, $C_{2-3}$-alkynyl, a $C_{1-3}$-alkyl group, or a $C_{1-3}$-alkoxy group, while the hydrogen atoms of the $C_{1-3}$-alkyl or $C_{1-3}$-alkoxy group may optionally be wholly or partly replaced by fluorine atoms, while, unless otherwise stated, by the term "heteroaryl group" mentioned hereinbefore in the definitions is meant a monocyclic 5- or 6-membered heteroaryl group, while the 6-membered heteroaryl group contains one, two or three nitrogen atoms and the 5-membered heteroaryl group contains an imino group optionally substituted by a $C_{1-3}$-alkyl, phenyl or phenyl-$C_{1-3}$-alkyl group, or an oxygen or sulphur atom or an imino group optionally substituted by a $C_{1-3}$-alkyl, phenyl, amino-$C_{2-3}$-alkyl, $C_{1-3}$-alkylamino-$C_{2-3}$-alkyl, di-($C_{1-3}$-alkyl)-amino-$C_{2-3}$-alkyl, a $C_{3-6}$-cycloalkyleneimino-$C_{1-3}$-alkyl or phenyl-$C_{1-3}$-alkyl group, or an oxygen or sulphur atom and additionally a nitrogen atom or an imino group optionally substituted by a $C_{1-3}$-alkyl or phenyl-$C_{1-3}$-alkyl group and two or three nitrogen atoms, and moreover a phenyl ring optionally substituted by a fluorine, chlorine or bromine atom, a $C_{1-3}$-alkyl, hydroxy, $C_{1-3}$-alkyloxy group, amino, $C_{1-3}$-alkylamino, di-($C_{1-3}$-alkyl)-amino or $C_{3-6}$-cycloalkyleneimino group may be fused to the above-mentioned monocyclic heteroaryl groups via two adjacent carbon atoms and the bond is effected via a nitrogen atom or a carbon atom of the heterocyclic moiety or a fused-on phenyl ring, while, unless otherwise stated, by the term "halogen atom" mentioned hereinbefore in the definitions is meant an atom selected from among fluorine, chlorine, bromine and iodine, while the alkyl, alkenyl, alkynyl and alkoxy groups contained in the above-mentioned definitions which have more than two carbon atoms may, unless otherwise stated, be straight-chain or branched and the alkyl groups in the previously mentioned dialkylated groups, for example the dialkylamino groups, may be identical or different, and the hydrogen atoms of the methyl or ethyl groups contained in the foregoing definitions, unless otherwise stated, may be wholly or partly replaced by fluorine atoms, the tautomers, the enantiomers, the diastereomers, the mixtures thereof and the salts thereof.

A second embodiment of the present invention includes those compounds of general formula I, wherein A denotes a group of general formula

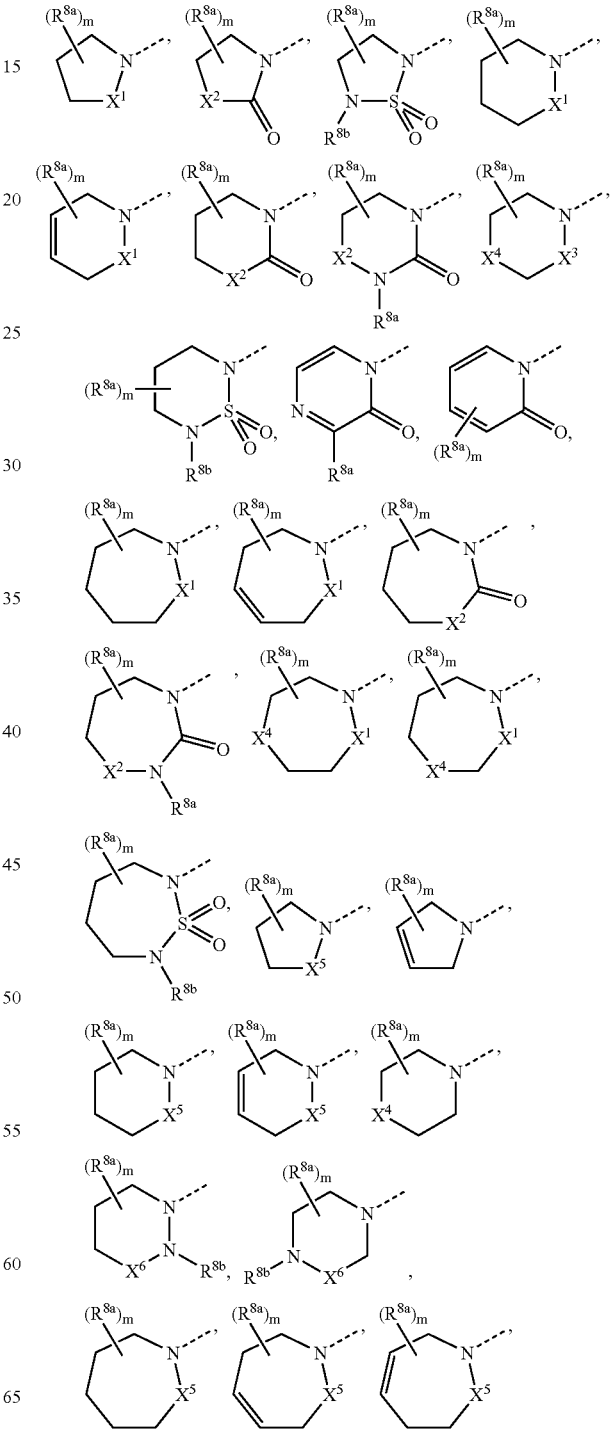

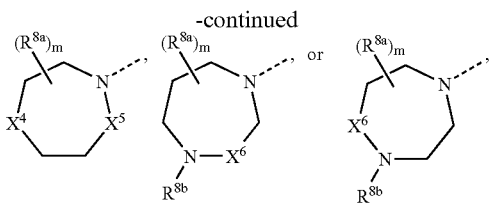

wherein m is the number 1 or 2, $R^{8a}$ each independently of one another denote a hydrogen or halogen atom or a $C_{1-5}$-alkyl, hydroxy, hydroxy-$C_{1-5}$-alkyl, $C_{1-5}$-alkoxy, $C_{1-5}$-alkoxy-$C_{1-5}$-alkyl, amino, $C_{1-5}$-alkylamino, di-($C_{1-5}$-alkyl)-amino, amino-$C_{1-5}$-alkyl, $C_{1-5}$-alkylamino-$C_{1-5}$-alkyl, di-($C_{1-5}$-alkyl)-amino-$C_{1-5}$-alkyl, aminocarbonyl, $C_{1-5}$-alkylaminocarbonyl, di-($C_{1-5}$-alkyl)-aminocarbonyl or $C_{1-5}$-alkylcarbonylamino group denotes, while in the previously mentioned substituted 5- to 7-membered groups A the heteroatoms F, Cl, Br, I, O or N optionally introduced with $R^{8a}$ as substituents are not separated by precisely one carbon atom from a heteroatom selected from among N, O and S, $R^{8b}$ each independently of one another denote a hydrogen atom or a $C_{1-5}$-alkyl group, $R^{8c}$ each independently of one another denote a hydrogen atom, a $C_{1-5}$-alkyl, $C_{1-5}$-alkylcarbonyl, $C_{1-5}$-alkyloxycarbonyl or $C_{1-5}$-alkylsulphonyl group, $X^1$ denotes a carbonyl, thiocarbonyl, C=$NR^{8c}$, C=N—$OR^{8c}$, C=N—$NO_2$, C=N—CN or sulphonyl group, $X^2$ denotes an oxygen atom or an —$NR^{8b}$ group, $X^3$ denotes a carbonyl, thiocarbonyl, C=$NR^{8c}$, C=N—$OR^{8c}$, C=N—$NO_2$, C=N—CN or sulphonyl group, $X^4$ denotes an oxygen or sulphur atom or an —$NR^{8c}$ group, $X^5$ denotes an oxygen atom or a —$CH_2$, —$CHR^{8a}$ or —$NR^{8c}$ group, $X^6$ denotes a carbonyl or sulphonyl group, $R^1$ denotes a hydrogen or halogen atom, a $C_{1-3}$-alkyl or $C_{1-3}$-alkoxy group, while the hydrogen atoms of the $C_{1-3}$-alkyl or $C_{1-3}$-alkoxy group may optionally be wholly or partly replaced by fluorine atoms, a $C_{2-3}$-alkenyl, $C_{2-3}$-alkynyl, nitrile, nitro or amino group, $R^2$ denotes a hydrogen or halogen atom or a $C_{1-3}$-alkyl group, X denotes a nitrogen atom or a CH group, $R^3$ denotes a hydrogen atom or a $C_{1-3}$-alkyl group, $R^4$ and $R^5$ each independently of one another denote a hydrogen atom, a hydroxy group, a $OR^9$ group, a $C_{2-6}$-alkenyl or $C_{2-6}$-alkynyl group, a straight-chain or branched $C_{1-6}$-alkyl group, while the hydrogen atoms of the straight-chain or branched $C_{1-6}$-alkyl group may optionally be wholly or partly replaced by fluorine atoms, and which may optionally be substituted by a $C_{3-5}$-cycloalkyl group, a nitrile, hydroxy, a $C_{1-5}$-alkyloxy group, while the hydrogen atoms of the $C_{1-5}$-alkyloxy group may optionally be wholly or partly replaced by fluorine atoms, an allyloxy, propargyloxy, benzyloxy, $C_{1-5}$-alkylcarbonyloxy, $C_{1-5}$-alkyloxycarbonyloxy, carboxy-$C_{1-5}$-alkyloxy, $C_{1-5}$-alkyloxycarbonyl-$C_{1-5}$-alkyloxy, mercapto, $C_{1-5}$-alkylsulphanyl, $C_{1-5}$-alkylsulphonyl, carboxy, $C_{1-5}$-alkyloxycarbonyl, aminocarbonyl, $C_{1-5}$-alkylaminocarbonyl, di-($C_{1-5}$-alkyl)-aminocarbonyl, $C_{3-6}$-cycloalkyleneiminocarbonyl, aminosulphonyl, $C_{1-5}$-alkylaminosulphonyl, di-($C_{1-5}$-alkyl)-aminosulphonyl, $C_{3-6}$-cycloalkyleneiminosulphonyl, amino, $C_{1-5}$-alkylamino, di-($C_{1-5}$-alkyl)-amino, $C_{1-5}$-alkylcarbonylamino, $C_{1-5}$-alkylsulphonylamino, N-($C_{1-5}$-alkylsulphonyl)-$C_{1-5}$-alkylamino or $C_{3-6}$-cycloalkylcarbonylamino group, while the 6- to 7-membered cyclic groups of the $C_{3-6}$-cycloalkyleneiminocarbonyl group in the cyclic moiety a methylene group in the 4 position of a 6- or 7-membered cycloalkyleneimino group may be replaced by an oxygen or sulphur atom, by a carbonyl, sulphinyl, sulphonyl or —$NR^{8c}$ group and additionally a methylene group adjacent to an above-mentioned —$NR^{8c}$ group may be replaced by a carbonyl group, a phenyl or heteroaryl group which may optionally be mono- to trisubstituted in the phenyl or heteroaryl moiety by identical or different substituents selected from among halogen atoms, $C_{1-5}$-alkyl, di-($C_{1-5}$-alkyl)-amino, hydroxy, $C_{1-5}$-alkyloxy, mono-, di- or trifluoromethoxy, carboxy- and $C_{1-5}$-alkyloxycarbonyl groups, a phenyl-$C_{1-5}$-alkyl or heteroaryl-$C_{1-5}$-alkyl group, which may optionally be mono- to trisubstituted in the phenyl or heteroaryl moiety by identical or different substituents selected from among halogen atoms, $C_{1-5}$-alkyl, di-($C_{1-5}$-alkyl)-amino, hydroxy, $C_{1-5}$-alkyloxy, mono-, di- or trifluoromethoxy, carboxy- and $C_{1-5}$-alkyloxycarbonyl groups, and which may optionally be substituted in the $C_{1-5}$-alkyl-moiety by a hydroxy, a $C_{1-5}$-alkyloxy group, while the hydrogen atoms of the $C_{1-5}$-alkyloxy group may optionally be wholly or partly replaced by fluorine atoms, an allyloxy, propargyloxy, benzyloxy, $C_{1-5}$-alkylcarbonyloxy, $C_{1-5}$-alkyloxycarbonyloxy, carboxy-$C_{1-5}$-alkyloxy, or a $C_{1-5}$-alkyloxycarbonyl-$C_{1-5}$-alkyloxy group;

a 3- to 7-membered cycloalkyl, cycloalkyleneimino, cycloalkyl-$C_{1-5}$-alkyl or cycloalkyleneimino-$C_{1-3}$-alkyl group, wherein in 4- to 7-membered cyclic groups in the cyclic moiety a methylene group may optionally be replaced by an —N($R^{8c}$) group, an oxygen or sulphur atom or a —S(O) or —S(O)$_2$ group, or wherein in 4- to 7-membered cyclic groups in the cyclic moiety two adjacent methylene groups together may optionally be replaced by a —C(O)N($R^{8b}$) or —S(O)$_2$N($R^{8b}$) group, or wherein in 6- to 7-membered cyclic groups in the cyclic moiety three adjacent methylene groups together may optionally be replaced by a substituted —OC(O)N($R^{8b}$) or —N($R^{8b}$)C(O)N($R^{8b}$) or —N(R $^{8b}$)S(O)$_2$N($R^{8b}$) group, with the proviso that a 3- to 7-membered cycloalkyl, cycloalkyleneimino, cycloalkyl-$C_{1-5}$-alkyl or cycloalkyleneimino-$C_{1-3}$-alkyl group as hereinbefore defined wherein two heteroatoms from the group comprising oxygen and nitrogen are separated from one another by precisely one optionally substituted —$CH_2$ group, is excluded, while a 3- to 7-membered cycloalkyl, cycloalkyleneimino, cycloalkyl-$C_{1-5}$-alkyl or cycloalkyleneimino-$C_{1-3}$-alkyl group as hereinbefore defined may be substituted at one or two —$CH_2$ groups by one or two $C_{1-3}$-alkyl groups in each case, with the proviso that $R^4$ and $R^5$ cannot simultaneously be defined as hydroxy or $OR^9$ groups, or $R^4$ and $R^5$ together with the carbon atom to which they are bound form a $C_{3-8}$-cycloalkyl or $C_{3-8}$-cycloalkenyl group, while one of the methylene groups of a $C_{4-8}$-cycloalkyl group may be replaced by an oxygen or sulphur atom or an —$N(R^{8c})$, or a carbonyl, sulphinyl or sulphonyl group, and/or two directly adjacent methylene groups of a $C_{4-8}$-cycloalkyl group may together be replaced by a —C(O)N$(R^{8b})$ or —S(O)$_2$N$(R^{8b})$ group, and/or three directly adjacent methylene groups of a $C_{6-8}$-cycloalkyl group may together be replaced by a —OC(O)N$(R^{8b})$, —N$(R^{8b})$C(O)N$(R^{8b})$ or —N$(R^{8b})$S(O)$_2$N$(R^{8b})$ group, while 1 to 3 carbon atoms of a $C_{3-8}$-cycloalkyl group may optionally be substituted independently of one another by in each case one or two identical or different halogen atoms or $C_{1-5}$-alkyl, nitrile, hydroxy, $C_{1-5}$-alkyloxy, $C_{1-5}$-alkylcarbonyloxy, carboxy-$C_{1-5}$-alkyl, $C_{1-5}$-alkyloxycarbonyl-$C_{1-5}$-alkyl, $C_{1-5}$-alkylsulphanyl, $C_{1-5}$-alkylsulphonyl, carboxy, $C_{1-5}$-alkyloxycarbonyl, aminocarbonyl, $C_{1-5}$-alkylaminocarbonyl, di-($C_{1-5}$-alkyl)-aminocarbonyl, $C_{3-6}$-cycloalkyleneiminocarbonyl, aminosulphonyl, $C_{1-5}$-alkylaminosulphonyl, di-($C_{1-5}$-alkyl)-aminosulphonyl, $C_{3-6}$-cycloalkyleneiminosulphonyl, amino, $C_{1-5}$-alkylamino, di-($C_{1-5}$-alkyl)-amino, $C_{1-5}$-alkylcarbonylamino, $C_{1-5}$-alkyl-sulphonylamino, N-($C_{1-5}$-alkylsulphonyl)-$C_{1-5}$-alkylamino or $C_{3-6}$-cycloalkylcarbonylamino groups, while 1 to 2 carbon atoms of a $C_{3-8}$-cycloalkenyl group may optionally be substituted independently of one another by in each case a $C_{1-5}$-alkyl, nitrile, carboxy-$C_{1-5}$-alkyl, $C_{1-5}$-alkyloxycarbonyl-$C_{1-5}$-alkyl, carboxy, $C_{1-5}$-alkyloxycarbonyl, aminocarbonyl, $C_{1-5}$-alkylaminocarbonyl, di-($C_{1-5}$-alkyl)-aminocarbonyl, $C_{3-6}$-cycloalkyleneiminocarbonyl, aminosulphonyl, $C_{1-5}$-alkylaminosulphonyl, di-($C_{1-5}$-alkyl)-aminosulphonyl, $C_{3-6}$-cycloalkyleneiminosulphonyl groups, and 1 to 2 carbon atoms of a $C_{4-8}$-cycloalkenyl group which are not bound by a double bond to another carbon atom may optionally be substituted independently of one another by a fluorine atom or a hydroxy, $C_{1-5}$-alkyloxy, $C_{1-5}$-alkylcarbonyloxy, $C_{1-5}$-alkylsulphanyl, $C_{1-5}$-alkylsulphonyl, amino, $C_{1-5}$-alkylamino, di-($C_{1-5}$-alkyl)-amino, $C_{1-5}$-alkylcarbonylamino, $C_{1-5}$-alkylsulphonylamino, N-($C_{1-5}$-alkylsulphonyl)-$C_{1-5}$-alkylamino or $C_{3-6}$-cycloalkylcarbonyl-amino groups, with the proviso that a $C_{3-8}$-cycloalkyl or $C_{3-8}$-cycloalkenyl group of this kind formed from $R^4$ and $R^5$ together, wherein two heteroatoms in the cyclic group selected from among oxygen and nitrogen are separated from one another by precisely one optionally substituted —CH$_2$ group, and/or wherein one or both methylene groups of the cyclic group, which are directly attached to the carbon atom to which the groups $R^4$ and $R^5$ are bound, are replaced by a heteroatom from the group comprising oxygen, nitrogen and sulphur, and/or wherein a substituent bound to the cyclic group, which is characterised in that a heteroatom selected from among oxygen, nitrogen, sulphur and halogen atom is bound directly to the cyclic group, is separated from another heteroatom selected from among oxygen, nitrogen and sulphur, with the exception of the sulphone group, by precisely one, optionally substituted methylene group, and/or wherein two oxygen atoms are joined together directly, is excluded, $R^9$ denotes a straight-chain or branched $C_{1-6}$-alkyl group, while the hydrogen atoms of the straight-chain or branched $C_{1-6}$-alkyl group may optionally be wholly or partly replaced by fluorine atoms, and which may optionally be substituted by a $C_{3-5}$-cycloalkyl group, a hydroxy, a $C_{1-5}$-alkyloxy group, while the hydrogen atoms of the $C_{1-5}$-alkyloxy group may optionally be wholly or partly replaced by fluorine atoms, an allyloxy, propargyloxy, benzyloxy, $C_{1-5}$-alkylcarbonyloxy, $C_{1-5}$-alkyloxycarbonyloxy, carboxy-$C_{1-5}$-alkyloxy, $C_{1-5}$-alkyloxycarbonyl-$C_{1-5}$-alkyloxy, carboxy, $C_{1-5}$-alkyloxycarbonyl, aminocarbonyl, $C_{1-5}$-alkylaminocarbonyl, di-($C_{1-5}$-alkyl)-aminocarbonyl, $C_{3-6}$-cycloalkyleneiminocarbonyl, amino, $C_{1-5}$-alkylamino, di-($C_{1-5}$-alkyl)-amino, $C_{1-5}$-alkylcarbonylamino, $C_{1-5}$-alkylsulphonylamino, N-($C_{1-5}$-alkylsulphonyl)-$C_{1-5}$-alkylamino or $C_{3-6}$-cycloalkylcarbonylamino group, while the 6- to 7-membered cyclic groups of the $C_{3-6}$-cycloalkyleneiminocarbonyl group in the cyclic moiety a methylene group in the 4 position of a 6- or 7-membered cycloalkyleneimino group may be replaced by an oxygen or sulphur atom, by a carbonyl, sulphinyl, sulphonyl or —$NR^{8c}$ group and additionally a methylene group adjacent to an above-mentioned —$NR^{8c}$ group may be replaced by a carbonyl group, with the proviso that the replacement of hydrogen atoms of the first carbon atom of the straight-chain or branched $C_{1-6}$-alkyl group by substituents from the group comprising oxygen, sulphur or nitrogen is excluded, a phenyl, heteroaryl, phenyl-$C_{1-5}$-alkyl or heteroaryl-$C_{1-5}$-alkyl group, which may optionally be mono- to trisubstituted in the phenyl or heteroaryl moiety by identical or different substituents selected from among halogen atoms, $C_{1-5}$-alkyl, di-($C_{1-5}$-alkyl)-amino, hydroxy, $C_{1-5}$-alkyloxy, mono-, di- or trifluoromethoxy, carboxy- and $C_{1-5}$-alkyloxycarbonyl groups, a 3- to 7-membered cycloalkyl, cycloalkyl-$C_{1-5}$-alkyl or cycloalkyleneimino-$C_{2-3}$-alkyl group, wherein in 4- to 7-membered cyclic groups in the cyclic moiety a methylene group may optionally be replaced by an —$N(R^8c)$ group, an oxygen or sulphur atom or a —S(O) or —S(O)$_2$ group, or wherein in 4- to 7-membered cyclic groups in the cyclic moiety two adjacent methylene groups together may optionally be replaced by a —C(O)N$(R^{8b})$ or —S(O)$_2$N$(R^{8b})$ group, or wherein in 6- to 7-membered cyclic groups in the cyclic moiety three adjacent methylene groups together may optionally be replaced by a substituted —OC(O)N$(R^{8b})$ or —N$(R^{8b})$C(O)N$(R^{8b})$ or —N$(R^{8b})$S(O)$_2$N$(R^{8b})$ group, with the proviso that a 3- to 7-membered cycloalkyl, cycloalkyl-$C_{1-5}$-alkyl or cycloalkyleneimino-$C_{2-3}$-alkyl group as hereinbefore defined wherein two heteroatoms from the group comprising oxygen and nitrogen are separated from one another by precisely one optionally substituted —CH$_2$ group, is excluded, while a 3- to 7-membered cycloalkyl, cycloalkyl-$C_{1-5}$-alkyl or cycloalkyleneimino-$C_{2-3}$-alkyl group as hereinbefore defined may be substituted at one or two —CH$_2$ groups by one or two $C_{1-3}$-alkyl groups in each case, B denotes a group of general formula

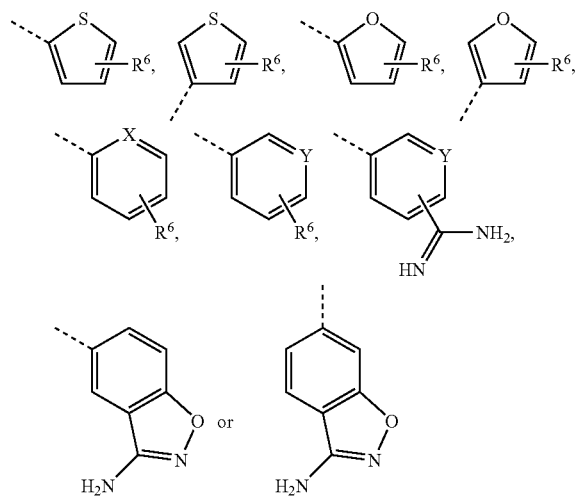

Y denotes a nitrogen atom or a CH group, $R^6$ denotes a hydrogen, a halogen atom, a nitrile group, a $C_{2-3}$-alkenyl, $C_{2-3}$-alkynyl, a $C_{1-3}$-alkyl group, or a $C_{1-3}$-alkoxy group, while the hydrogen atoms of the $C_{1-3}$-alkyl or $C_{1-3}$-alkoxy group may optionally be wholly or partly replaced by fluorine atoms, while, unless otherwise stated, by the term "heteroaryl group" mentioned hereinbefore in the definitions is meant a monocyclic 5- or 6-membered heteroaryl group, while the 6-membered heteroaryl group contains one, two or three nitrogen atoms and the 5-membered heteroaryl group contains an imino group optionally substituted by a $C_{1-3}$-alkyl, phenyl or phenyl-$C_{1-3}$-alkyl group, or an oxygen or sulphur atom or an imino group optionally substituted by a $C_{1-3}$-alkyl, phenyl, amino-$C_{2-3}$-alkyl, $C_{1-3}$-alkylamino-$C_{2-3}$-alkyl, di-($C_{1-3}$-alkyl)-amino-$C_{2-3}$-alkyl, a $C_{3-6}$-cycloalkyleneimino-$C_{1-3}$-alkyl or phenyl-$C_{1-3}$-alkyl group, or an oxygen or sulphur atom and additionally a nitrogen atom or an imino group optionally substituted by a $C_{1-3}$-alkyl or phenyl-$C_{1-3}$-alkyl group and two or three nitrogen atoms, and moreover a phenyl ring optionally substituted by a fluorine, chlorine or bromine atom, a $C_{1-3}$-alkyl, hydroxy, $C_{1-3}$-alkyloxy group, amino, $C_{1-3}$-alkylamino, di-($C_{1-3}$-alkyl)-amino or $C_{3-6}$-cycloalkyleneimino group may be fused to the above-mentioned monocyclic heteroaryl groups via two adjacent carbon atoms and the bond is effected via a nitrogen atom or a carbon atom of the heterocyclic moiety or a fused-on phenyl ring, while, unless otherwise stated, by the term "halogen atom" mentioned hereinbefore in the definitions is meant an atom selected from among fluorine, chlorine, bromine and iodine, while the alkyl, alkenyl, alkynyl and alkoxy groups contained in the above-mentioned definitions which have more than two carbon atoms, unless otherwise stated, may be straight-chain or branched and the alkyl groups in the previously mentioned dialkylated groups, for example the dialkylamino groups, may be identical or different, and the hydrogen atoms of the methyl or ethyl groups contained in the foregoing definitions, unless otherwise stated, may be wholly or partly replaced by fluorine atoms, the tautomers, the enantiomers, the diastereomers, the mixtures thereof and the salts thereof.

A third embodiment of the present invention includes those compounds of general formula I, wherein A denotes a group of general formula

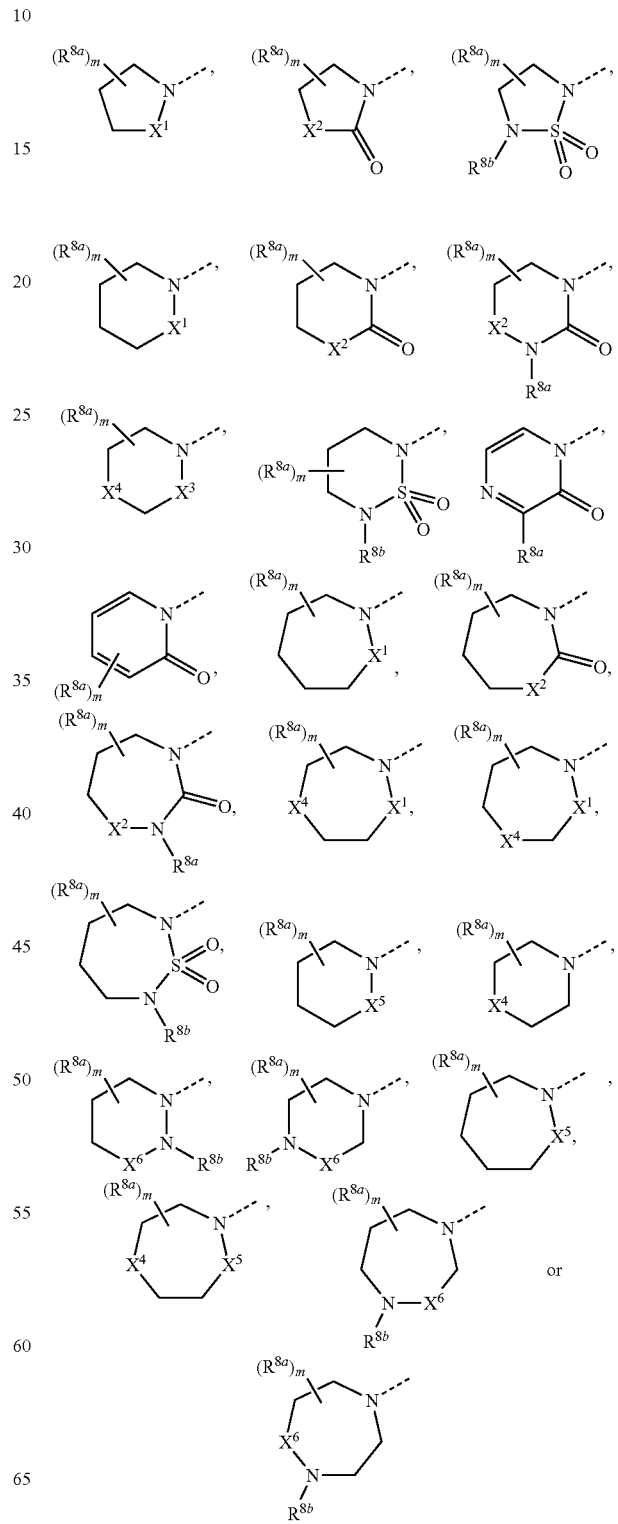

wherein m is the number 1 or 2, $R^{8a}$ each independtnly of one another dneote a hydrogen pr fluorine atom or a $C_{1-3}$-alkyl, hydroxy, hydroxy-$C_{1-3}$-alkyl, $C_{1-3}$-alkoxy, $C_{1-3}$-alkoxy-$C_{1-3}$-alkyl, amino, $C_{1-3}$-alkylamino, di-($C_{1-3}$-alkyl)-amino, amino-$C_{1-3}$-alkyl, $C_{1-3}$-alkylamino-$C_{1-3}$-alkyl, or di-($C_{1-3}$-alkyl)-amino-$C_{1-3}$-alkyl group, while in the previously mentioned substituted 5- to 7-membered groups A the heteroatoms F, O or N optionally introduced with $R^{8a}$ as substituents are not separated by precisely one carbon atom from a heteroatom selected from among N, O and S, $R^{8b}$ each independently of one another denote a hydrogen atom or a $C_{1-3}$-alkyl group, $R^{8c}$ each independently of one another denote a hydrogen atom, a $C_{1-3}$-alkyl, $C_{1-3}$-alkylcarbonyl, $C_{1-3}$-alkyloxycarbonyl or $C_{1-3}$-alkylsulphonyl group, $X^1$ denotes a carbonyl, thiocarbonyl, C=$NR^{8c}$, C=N—$OR^{8c}$, C=N—$NO_2$, C=N—CN or sulphonyl group, $X^2$ denotes an oxygen atom or an —$NR^{8b}$ group, $X^3$ denotes a carbonyl, thiocarbonyl, C=$NR^{8c}$, C=N—$OR^{8c}$, C=N—$NO_2$, C=N—CN or sulphonyl group, $X^4$ denotes an oxygen or sulphur atom or an —$NR^{8c}$ group, $X^5$ denotes an oxygen atom or a —$CH_2$, —$CHR^{8a}$ or —$NR^{8c}$ group, $X^6$ denotes a carbonyl or sulphonyl group, $R^1$ denotes a hydrogen or halogen atom, a $C_{1-3}$-alkyl or $C_{1-3}$-alkoxy group, while the hydrogen atoms of the $C_{1-3}$-alkyl or $C_{1-3}$-alkoxy group may optionally be wholly or partly replaced by fluorine atoms, a $C_{2-3}$-alkenyl, $C_{2-3}$-alkynyl, nitrile, nitro or amino group, $R^2$ denotes a hydrogen or halogen atom or a methyl group, X denotes a nitrogen atom or a CH group, $R^3$ denotes a hydrogen atom or a $C_{1-3}$-alkyl group, $R^4$ and $R^5$ each independently of one another denote a hydrogen atom, a hydroxy group, a $OR^9$ group, a $C_{2-6}$-alkenyl or $C_{2-6}$-alkynyl group, a straight-chain or branched $C_{1-6}$-alkyl group, while the hydrogen atoms of the straight-chain or branched $C_{1-6}$-alkyl group may optionally be wholly or partly replaced by fluorine atoms, and which may optionally be substituted by a $C_{3-5}$-cycloalkyl group, a nitrile, hydroxy, a $C_{1-5}$-alkyloxy group, while the hydrogen atoms of the $C_{1-5}$-alkyloxy group may optionally be wholly or partly replaced by fluorine atoms, an allyloxy, propargyloxy, benzyloxy, $C_{1-5}$-alkylcarbonyloxy, $C_{1-5}$-alkyloxycarbonyloxy, carboxy-$C_{1-5}$-alkyloxy, $C_{1-5}$-alkyloxycarbonyl-$C_{1-5}$-alkyloxy, mercapto, $C_{1-5}$-alkylsulphanyl, $C_{1-5}$-alkylsulphonyl, carboxy, $C_{1-5}$-alkyloxycarbonyl, aminocarbonyl, $C_{1-5}$-alkylaminocarbonyl, di-($C_{1-5}$-alkyl)-aminocarbonyl, $C_{3-6}$-cycloalkyleneiminocarbonyl, aminosulphonyl, $C_{1-5}$-alkylaminosulphonyl, di-($C_{1-5}$-alkyl)-aminosulphonyl, $C_{3-6}$-cycloalkyleneiminosulphonyl, amino, $C_{1-5}$-alkylamino, di-($C_{1-5}$-alkyl)-amino, $C_{1-5}$-alkylcarbonylamino, $C_{1-5}$-alkylsulphonylamino, N-($C_{1-5}$-alkylsulphonyl)-$C_{1-5}$-alkylamino or $C_{3-6}$-cycloalkylcarbonylamino group, while the 6- to 7-membered cyclic groups of the $C_{3-6}$-cycloalkyleneiminocarbonyl group in the cyclic moiety a methylene group in the 4 position of a 6- or 7-membered cycloalkyleneimino group may be replaced by an oxygen or sulphur atom, by a carbonyl, sulphinyl, sulphonyl or —$NR^{8c}$ group and additionally a methylene group adjacent to an above-mentioned —$NR^{8c}$ group may be replaced by a carbonyl group, a phenyl, heteroaryl, phenyl-$C_{1-5}$-alkyl or heteroaryl-$C_{1-5}$-alkyl group, which may optionally be mono- to trisubstituted in the phenyl or heteroaryl moiety by identical or different substituents selected from among halogen atoms, $C_{1-5}$-alkyl, di-($C_{1-5}$-alkyl)-amino, hydroxy, $C_{1-5}$-alkyloxy, mono-, di- or trifluoromethoxy, carboxy- and $C_{1-5}$-alkyloxycarbonyl groups, a 3- to 7-membered cycloalkyl, cycloalkyleneimino, cycloalkyl-$C_{1-5}$-alkyl or cycloalkyleneimino-$C_{1-3}$-alkyl group, wherein in 4- to 7-membered cyclic groups in the cyclic moiety a methylene group may optionally be replaced by an —$N(R^{8c})$ group, an oxygen or sulphur atom or a —S(O) or —$S(O)_2$ group, or wherein in 4- to 7-membered cyclic groups in the cyclic moiety two adjacent methylene groups together may optionally be replaced by a —$C(O)N(R^{8b})$ or —$S(O)_2N(R^{8b})$ group, or wherein in 6- to 7-membered cyclic groups in the cyclic moiety three adjacent methylene groups together may optionally be replaced by a substituted —OC(O)N($R^{8b}$) or —N($R^{8b}$)C(O)N($R^{8b}$) or —N($R^{8b}$)S(O)$_2$N($R^{8b}$) group, with the proviso that a 3- to 7-membered cycloalkyl, cycloalkyleneimino, cycloalkyl-$C_{1-5}$-alkyl or cycloalkyleneimino-$C_{1-3}$-alkyl group as hereinbefore defined wherein two heteroatoms from the group comprising oxygen and nitrogen are separated from one another by precisely one optionally substituted —$CH_2$ group, is excluded, while a 3- to 7-membered cycloalkyl, cycloalkyleneimino, cycloalkyl-$C_{1-5}$-alkyl or cycloalkyleneimino-$C_{1-3}$-alkyl group as hereinbefore defined may be substituted at one or two —$CH_2$ groups by one or two $C_{1-3}$-alkyl groups in each case, with the proviso that $R^4$ and $R^5$ cannot simultaneously be defined as hydroxy or $OR^9$ groups, $R^9$ denotes a straight-chain or branched $C_{1-6}$-alkyl group, while the hydrogen atoms of the straight-chain or branched $C_{1-6}$-alkyl group may optionally be wholly or partly replaced by fluorine atoms, and which may optionally be substituted by a $C_{3-5}$-cycloalkyl group, a hydroxy, a $C_{1-5}$-alkyloxy group, while the hydrogen atoms of the $C_{1-5}$-alkyloxy group may optionally be wholly or partly replaced by fluorine atoms, an allyloxy, propargyloxy, benzyloxy, $C_{1-5}$-alkylcarbonyloxy, $C_{1-5}$-alkyloxycarbonyloxy, carboxy-$C_{1-5}$-alkyloxy, $C_{1-5}$-alkyloxycarbonyl-$C_{1-5}$-alkyloxy, carboxy, $C_{1-5}$-alkyloxycarbonyl, aminocarbonyl, $C_{1-5}$-alkylaminocarbonyl, di-($C_{1-5}$-alkyl)-aminocarbonyl, $C_{3-6}$-cycloalkyleneiminocarbonyl, amino, $C_{1-5}$-alkylamino, di-($C_{1-5}$-alkyl)-amino, $C_{1-5}$-alkylcarbonylamino, $C_{1-5}$-alkylsulphonylamino, N-($C_{1-5}$-alkylsulphonyl)-$C_{1-5}$-alkylamino or $C_{3-6}$-cycloalkylcarbonylamino group, while the 6- to 7-membered cyclic groups of the $C_{3-6}$-cycloalkyleneiminocarbonyl group in the cyclic moiety a methylene group in the 4 position of a 6- or 7-membered cycloalkyleneimino group by an oxygen or sulphur atom may be replaced by a carbonyl, sulphinyl, sulphonyl or —$NR^{8c}$ group and additionally a methylene group adjacent to an above-mentioned —$NR^{8c}$ group may be replaced by a carbonyl group, with the proviso that the replacement of hydrogen atoms of the first carbon atom of the straight-chain or branched $C_{1-6}$-alkyl group by substituents from the group comprising oxygen, sulphur or nitrogen is excluded, a phenyl or heteroaryl group
which may optionally be mono- to trisubstituted in the phenyl or heteroaryl moiety by identical or different substituents selected from among halogen atoms, $C_{1-5}$-alkyl, di-($C_{1-5}$-alkyl)-amino, hydroxy, $C_{1-5}$-alkyloxy, mono-, di- or trifluoromethoxy, carboxy- and $C_{1-5}$-alkyloxycarbonyl groups, a phenyl-$C_{1-5}$-alkyl or heteroaryl-$C_{1-5}$-alkyl group,
which may optionally be mono- to trisubstituted in the phenyl or heteroaryl moiety by identical or different substituents selected from among halogen atoms, $C_{1-5}$-alkyl, di-($C_{1-5}$-alkyl)-amino, hydroxy, $C_{1-5}$-alkyloxy, mono-, di- or trifluoromethoxy, carboxy- and $C_{1-5}$-alkyloxycarbonyl groups, and which may optionally be substituted in the $C_{1-5}$-alkyl-moiety by a hydroxy, a $C_{1-5}$-alkyloxy group, while the hydrogen atoms of the $C_{1-5}$-alkyloxy group may optionally be wholly or partly replaced by fluorine atoms, an allyloxy, propargyloxy, benzyloxy, $C_{1-5}$-alkylcarbonyloxy, $C_{1-5}$-alkyloxycarbonyloxy, carboxy-$C_{1-5}$-alkyloxy, or a $C_{1-5}$-alkyloxycarbonyl-$C_{1-5}$-alkyloxy group;

a 3- to 7-membered cycloalkyl, cycloalkyl-$C_{1-5}$-alkyl or cycloalkyleneimino-$C_{2-3}$-alkyl group,
wherein in 4- to 7-membered cyclic groups in the cyclic moiety a methylene group may optionally be replaced by an —N($R^{8c}$) group, an oxygen or sulphur atom or a —S(O) or —S(O)$_2$ group, or wherein in 4- to 7-membered cyclic groups in the cyclic moiety two adjacent methylene groups together may optionally be replaced by a —C(O)N($R^{8b}$) or —S(O)$_2$N($R^{8b}$) group, or wherein in 6- to 7-membered cyclic groups in the cyclic moiety three adjacent methylene groups together may optionally be replaced by a substituted —OC(O)N($R^{8b}$) or —N($R^{8b}$)C(O)N($R^{8b}$) or —N($R^{8b}$)S(O)$_2$N($R^{8b}$) group, with the proviso that a 3- to 7-membered cycloalkyl, cycloalkyl-$C_{1-5}$-alkyl or cycloalkyleneimino-$C_{2-3}$-alkyl group as hereinbefore defined wherein two heteroatoms from the group comprising oxygen and nitrogen are separated from one another by precisely one optionally substituted —CH$_2$ group, is excluded, while a 3- to 7-membered cycloalkyl, cycloalkyl-$C_{1-5}$-alkyl or cycloalkyleneimino-$C_{2-3}$-alkyl group as hereinbefore defined may be substituted at one or two —CH$_2$ groups by one or two $C_{1-3}$-alkyl groups in each case, B denotes a group of general formula

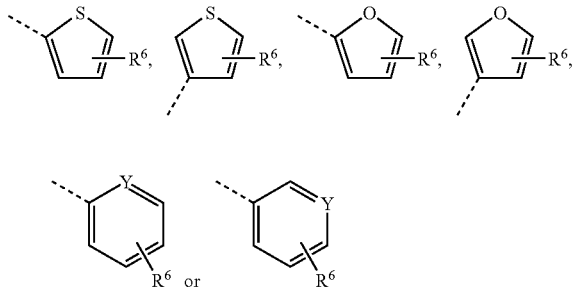

Y denotes a nitrogen atom or a CH group, $R^6$ denotes a hydrogen, a halogen atom, an ethynyl, a methyl group, a methoxy group, while the hydrogen atoms of the methoxy group may optionally be wholly or partly replaced by fluorine atoms, while, unless otherwise stated, by the term "heteroaryl group" mentioned hereinbefore in the definitions is meant a monocyclic 5- or 6-membered heteroaryl group, while the 6-membered heteroaryl group contains one, two or three nitrogen atoms and the 5-membered heteroaryl group contains an imino group optionally substituted by a $C_{1-3}$-alkyl, phenyl or phenyl-$C_{1-3}$-alkyl group, an oxygen or sulphur atom or an imino group optionally substituted by a $C_{1-3}$-alkyl, phenyl, amino-$C_{2-3}$-alkyl, $C_{1-3}$-alkylamino-$C_{2-3}$-alkyl, di-($C_{1-3}$-alkyl)-amino-$C_{2-3}$-alkyl, a $C_{3-6}$-cycloalkyleneimino-$C_{1-3}$-alkyl or phenyl-$C_{1-3}$-alkyl group or an oxygen or sulphur atom and additionally a nitrogen atom or an imino group optionally substituted by a $C_{1-3}$-alkyl or phenyl-$C_{1-3}$-alkyl group and two or three nitrogen atoms, and moreover a phenyl ring optionally substituted by a fluorine, chlorine or bromine atom, a $C_{1-3}$-alkyl, hydroxy, $C_{1-3}$-alkyloxy group, amino, $C_{1-3}$-alkylamino, di-($C_{1-3}$-alkyl)-amino or $C_{3-6}$-cycloalkyleneimino group may be fused to the above-mentioned monocyclic heteroaryl groups via two adjacent carbon atoms and the bond is effected via a nitrogen atom or a carbon atom of the heterocyclic moiety or a fused-on phenyl ring, while, unless otherwise stated, by the term "halogen atom" mentioned hereinbefore in the definitions is meant an atom selected from among fluorine, chlorine, bromine and iodine, while the alkyl, alkenyl, alkynyl and alkoxy groups contained in the above-mentioned definitions which have more than two carbon atoms, unless otherwise stated, may be straight-chain or branched and the alkyl groups in the previously mentioned dialkylated groups, for example the dialkylamino groups, may be identical or different, and the hydrogen atoms of the methyl or ethyl groups contained in the foregoing definitions, unless otherwise stated, may be wholly or partly replaced by fluorine atoms, the tautomers, the enantiomers, the diastereomers, the mixtures thereof and the salts thereof.

A fourth embodiment of the present invention includes those compounds of general formula I, wherein A denotes a group of general formula

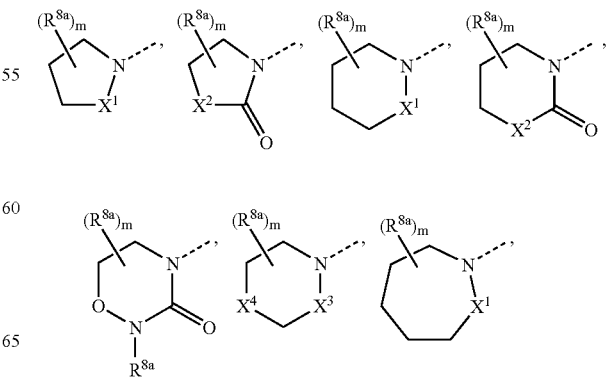

-continued

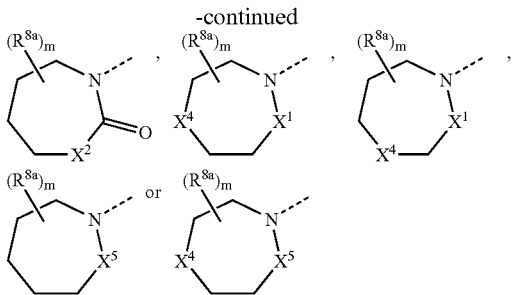

wherein m is the number 1 or 2, $R^{8a}$ each independently of one another denote a hydrogen or fluorine atom or a $C_{1-3}$-alkyl, hydroxy, hydroxy-$C_{1-3}$-alkyl, $C_{1-3}$-alkoxy, $C_{1-3}$-alkoxy-$C_{1-3}$-alkyl, amino, $C_{1-3}$-alkylamino, di-($C_{1-3}$-alkyl)-amino, amino-$C_{1-3}$-alkyl, $C_{1-3}$-alkylamino-$C_{1-3}$-alkyl, or di-($C_{1-3}$-alkyl)-amino-$C_{1-3}$-alkyl group, while in the previously mentioned substituted 5- to 7-membered groups A the heteroatoms F, O or N optionally introduced with $R^{8a}$ as substituents are not separated by precisely one carbon atom from a heteroatom selected from among N, O and S, $R^{8b}$ each independently of one another denote a hydrogen atom or a $C_{1-3}$-alkyl group, $R^{8c}$ each independently of one another denote a hydrogen atom, a $C_{1-3}$-alkyl, $C_{1-3}$-alkylcarbonyl, $C_{1-3}$-alkyloxycarbonyl or $C_{1-3}$-alkylsulphonyl group, $X^1$ denotes a carbonyl, or sulphonyl group, $X^2$ denotes an oxygen atom or an —$NR^{8b}$ group, $X^3$ denotes a carbonyl, thiocarbonyl, C=$NR^{8c}$, C=N—$OR^{8c}$, C=N—$NO_2$, C=N—CN or sulphonyl group, $X^4$ denotes an oxygen or sulphur atom or an —$NR^{8c}$ group, $X^5$ denotes an oxygen atom or a —$CH_2$, —$CHR^{8a}$ or —$NR^{8c}$ group, $R^1$ denotes a hydrogen or halogen atom, a $C_{1-3}$-alkyl or $C_{1-3}$-alkoxy group, while the hydrogen atoms of the $C_{1-3}$-alkyl or $C_{1-3}$-alkoxy group may optionally be wholly or partly replaced by fluorine atoms, a $C_{2-3}$-alkenyl, $C_{2-3}$-alkynyl, nitrile, nitro or amino group, $R^2$ denotes a hydrogen or fluorine atom or a methyl group, X denotes a nitrogen atom or a CH group, $R^3$ denotes a hydrogen atom or a $C_{1-3}$-alkyl group, $R^4$ denotes a hydrogen atom, a straight-chain or branched $C_{1-4}$-alkyl group, while the hydrogen atoms of the straight-chain or branched $C_{1-4}$-alkyl group may optionally be wholly or partly replaced by fluorine atoms, and which may optionally be substituted by a $C_{1-3}$-alkyloxy group, while the hydrogen atoms of the $C_{1-3}$-alkyloxy group may optionally be wholly or partly replaced by fluorine atoms, $R^5$ denotes a hydrogen atom, a hydroxy group, a $OR^9$ group, a $C_{2-4}$-alkenyl or $C_{2-4}$-alkynyl group, a straight-chain or branched $C_{1-4}$-alkyl group, while the hydrogen atoms of the straight-chain or branched $C_{1-4}$-alkyl group may optionally be wholly or partly replaced by fluorine atoms, and which may optionally be substituted by a $C_{3-5}$-cycloalkyl group, a nitrile, hydroxy, a $C_{1-5}$-alkyloxy group, while the hydrogen atoms of the $C_{1-5}$-alkyloxy group may optionally be wholly or partly replaced by fluorine atoms, an allyloxy, propargyloxy, benzyloxy, $C_{1-5}$-alkylcarbonyloxy, $C_{1-5}$-alkyloxycarbonyloxy, carboxy-$C_{1-5}$-alkyloxy, $C_{1-5}$-alkyloxycarbonyl-$C_{1-5}$-alkyloxy, mercapto, $C_{1-5}$-alkylsulphanyl, $C_{1-5}$-alkylsulphonyl, carboxy, $C_{1-5}$-alkyloxycarbonyl, aminocarbonyl, $C_{1-5}$-alkylaminocarbonyl, di-($C_{1-5}$-alkyl)-aminocarbonyl, $C_{3-6}$-cycloalkyleneiminocarbonyl, aminosulphonyl, $C_{1-5}$-alkylaminosulphonyl, di-($C_{1-5}$-alkyl)-aminosulphonyl, $C_{3-6}$-cycloalkyleneiminosulphonyl, amino, $C_{1-5}$-alkylamino, di-($C_{1-5}$-alkyl)-amino, $C_{1-5}$-alkylcarbonylamino, $C_{1-5}$-alkylsulphonylamino, N-($C_{1-5}$-alkylsulphonyl)-$C_{1-5}$-alkylamino or $C_{3-6}$-cycloalkylcarbonylamino group, while the 6- to 7-membered cyclic groups of the $C_{3-6}$-cycloalkyleneiminocarbonyl group in the cyclic moiety a methylene group in the 4 position of a 6- or 7-membered cycloalkyleneimino group may be replaced by an oxygen or sulphur atom, by a carbonyl, sulphinyl, sulphonyl or —$NR^{8c}$ group and additionally a methylene group adjacent to an above-mentioned —$NR^{8c}$ group may be replaced by a carbonyl group, a phenyl, heteroaryl, phenyl-$C_{1-5}$-alkyl or heteroaryl-$C_{1-5}$-alkyl group, which may optionally be mono- to trisubstituted in the phenyl or heteroaryl moiety may be substituted by identical or different substituents selected from among halogen atoms, $C_{1-5}$-alkyl, di-($C_{1-5}$-alkyl)-amino, hydroxy, $C_{1-5}$-alkyloxy, mono-, di- or trifluoromethoxy, carboxy- and $C_{1-5}$-alkyloxycarbonyl groups, $R^9$ denotes a straight-chain or branched $C_{1-4}$-alkyl group, while the hydrogen atoms of the straight-chain or branched $C_{1-4}$-alkyl group may optionally be wholly or partly replaced by fluorine atoms, and which may optionally be substituted by a $C_{3-5}$-cycloalkyl group, a hydroxy, a $C_{1-5}$-alkyloxy group, while the hydrogen atoms of the $C_{1-5}$-alkyloxy group may optionally be wholly or partly replaced by fluorine atoms, an allyloxy, propargyloxy, benzyloxy, $C_{1-5}$-alkylcarbonyloxy, $C_{1-5}$-alkyloxycarbonyloxy, carboxy-$C_{1-5}$-alkyloxy, $C_{1-5}$-alkyloxycarbonyl-$C_{1-5}$-alkyloxy, carboxy, $C_{1-5}$-alkyloxycarbonyl, aminocarbonyl, $C_{1-5}$-alkylaminocarbonyl, di-($C_{1-5}$-alkyl)-aminocarbonyl, $C_{3-6}$-cycloalkyleneiminocarbonyl, amino, $C_{1-5}$-alkylamino, di-($C_{1-5}$-alkyl)-amino, $C_{1-5}$-alkylcarbonylamino, $C_{1-5}$-alkylsulphonylamino, N-($C_{1-5}$-alkylsulphonyl)-$C_{1-5}$-alkylamino or $C_{3-6}$-cycloalkylcarbonylamino group, while the 6- to 7-membered cyclic groups of the $C_{3-6}$-cycloalkyleneiminocarbonyl group in the cyclic moiety a methylene group in the 4 position of a 6- or 7-membered cycloalkyleneimino group may be replaced by an oxygen or sulphur atom, by a carbonyl, sulphinyl, sulphonyl or —$NR^{8c}$ group and additionally a methylene group adjacent to an above-mentioned —$NR^{8c}$ group may be replaced by a carbonyl group, with the proviso that the replacement of hydrogen atoms of the first carbon atom of the straight-chain or branched $C_{1-4}$-alkyl group by substituents from the group comprising oxygen, sulphur or nitrogen is excluded, a phenyl or heteroaryl group which may optionally be mono- to trisubstituted in the phenyl or heteroaryl moiety by identical or different substituents selected from among halogen atoms, $C_{1-5}$-alkyl, di-($C_{1-5}$-alkyl)-amino, hydroxy, $C_{1-5}$- alkyloxy, mono-, di- or trifluoromethoxy, carboxy- and $C_{1-5}$-alkyloxycarbonyl groups, a phenyl-$C_{1-5}$-alkyl or heteroaryl-$C_{1-5}$-alkyl group,
which may optionally be mono- to trisubstituted in the phenyl or heteroaryl moiety by identical or different substituents selected from among halogen atoms, $C_{1-5}$-alkyl, di-($C_{1-5}$-alkyl)-amino, hydroxy, $C_{1-5}$-alkyloxy, mono-, di- or trifluoromethoxy, carboxy- and $C_{1-5}$-alkyloxycarbonyl groups, and which may optionally be substituted in the $C_{1-5}$-alkyl-moiety by a hydroxy, a $C_{1-5}$-alkyloxy group, while the hydrogen atoms of the $C_{1-5}$-alkyloxy group may optionally be wholly or partly replaced by fluorine atoms, an allyloxy, propargyloxy, benzyloxy, $C_{1-5}$-alkylcarbonyloxy, $C_{1-5}$-alkyloxycarbonyloxy, carboxy-$C_{1-5}$-alkyloxy, or a $C_{1-5}$-alkyloxycarbonyl-$C_{1-5}$-alkyloxy group;

B denotes a group of general formula

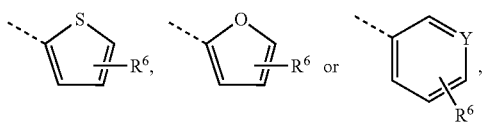

Y denotes a nitrogen atom or a CH group, $R^6$ denotes a hydrogen, a halogen atom, an ethynyl, a methyl group, a methoxy group, while the hydrogen atoms of the methoxy group may optionally be wholly or partly replaced by fluorine atoms, while, unless otherwise stated, by the term "heteroaryl group" mentioned hereinbefore in the definitions is meant a monocyclic 5- or 6-membered heteroaryl group, while the 6-membered heteroaryl group contains one, two or three nitrogen atoms and the 5-membered heteroaryl group contains an imino group optionally substituted by a $C_{1-3}$-alkyl, phenyl or phenyl-$C_{1-3}$-alkyl group, or an oxygen or sulphur atom or an imino group optionally substituted by a $C_{1-3}$-alkyl, phenyl, amino-$C_{2-3}$-alkyl, $C_{1-3}$-alkylamino-$C_{2-3}$-alkyl, di-($C_{1-3}$-alkyl)-amino-$C_{2-3}$-alkyl, a $C_{3-6}$-cycloalkyleneimino-$C_{1-3}$-alkyl or phenyl-$C_{1-3}$-alkyl group, or an oxygen or sulphur atom and additionally a nitrogen atom or an imino group optionally substituted by a $C_{1-3}$-alkyl or phenyl-$C_{1-3}$-alkyl group and two or three nitrogen atoms, and moreover a phenyl ring optionally substituted by a fluorine, chlorine or bromine atom, a $C_{1-3}$-alkyl, hydroxy, $C_{1-3}$-alkyloxy group, amino, $C_{1-3}$-alkylamino, di-($C_{1-3}$-alkyl)-amino or $C_{3-6}$-cycloalkyleneimino group may be fused to the above-mentioned monocyclic heteroaryl groups via two adjacent carbon atoms and the bond is effected via a nitrogen atom or a carbon atom of the heterocyclic moiety or a fused-on phenyl ring, while, unless otherwise stated, by the term "halogen atom" mentioned hereinbefore in the definitions is meant an atom selected from among fluorine, chlorine, bromine and iodine, while the alkyl, alkenyl, alkynyl and alkoxy groups contained in the above-mentioned definitions which have more than two carbon atoms, unless otherwise stated, may be straight-chain or branched and the alkyl groups in the previously mentioned dialkylated groups, for example the dialkylamino groups, may be identical or different, and the hydrogen atoms of the methyl or ethyl groups contained in the foregoing definitions, unless otherwise stated, may be wholly or partly replaced by fluorine atoms, the tautomers, the enantiomers, the diastereomers, the mixtures thereof and the salts thereof.

A fifth embodiment of the present invention includes those compounds of general formula I, wherein A denotes a group of general formula

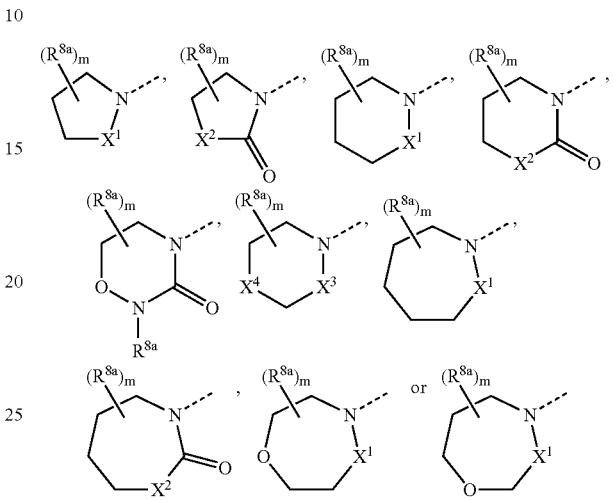

wherein m is the number 1 or 2, $R^{8a}$ each independently of one another denote a hydrogen or fluorine atom or a $C_{1-3}$-alkyl, hydroxy, hydroxy-$C_{1-3}$-alkyl, $C_{1-3}$-alkoxy, $C_{1-3}$-alkoxy-$C_{1-3}$-alkyl, amino, $C_{1-3}$-alkylamino, di-($C_{1-3}$-alkyl)-amino, amino-$C_{1-3}$-alkyl, $C_{1-3}$-alkylamino-$C_{1-3}$-alkyl, or di-($C_{1-3}$-alkyl)-amino-$C_{1-3}$-alkyl group, while in the previously mentioned substituted 5- to 7-membered groups A the heteroatoms F, O or N optionally introduced with $R^{8a}$ as substituents are not separated by precisely one carbon atom from a heteroatom selected from among N, O and S, $R^{8b}$ each independently of one another denote a hydrogen atom or a $C_{1-3}$-alkyl group, $R^{8c}$ each independently of one another denote a hydrogen atom, a $C_{1-3}$-alkyl, $C_{1-3}$-alkylcarbonyl, $C_{1-3}$-alkyloxycarbonyl or $C_{1-3}$-alkylsulphonyl group, $X^1$ denotes a carbonyl or sulphonyl group, $X^2$ denotes an oxygen atom or an —$NR^{8b}$ group, $X^3$ denotes a carbonyl, thiocarbonyl, C=$NR^{8c}$, C=N—$OR^{8c}$, C=N—$NO_2$, C=N—CN or sulphonyl group, $X^4$ denotes an oxygen or sulphur atom or an —$NR^{8c}$ group, $R^1$ denotes a hydrogen, fluorine, chlorine or bromine atom, a methyl or methoxy group, while the hydrogen atoms of the methyl or methoxy group may optionally be wholly or partly replaced by fluorine atoms, $R^2$ denotes a hydrogen or fluorine atom, X denotes a nitrogen atom or a CH group, $R^3$ denotes a hydrogen atom or a $C_{1-3}$-alkyl group, $R^4$ denotes a hydrogen atom, $R^5$ denotes a hydrogen atom, a hydroxy group, a $OR^9$ group, a $C_{2-4}$-alkenyl or $C_{2-4}$-alkynyl group, a straight-chain or branched $C_{1-4}$-alkyl group,
while the hydrogen atoms may optionally be wholly or partly replaced by fluorine atoms, and which may optionally be substituted by a hydroxy, a $C_{1-3}$-alkyloxy group, while the hydrogen atoms of the $C_{1-3}$- alkyloxy group may be wholly or partly replaced by fluorine atoms, a benzyloxy, $C_{1-3}$-alkylcarbonyloxy, $C_{1-3}$-alkyloxycarbonyl, aminocarbonyl, $C_{1-3}$-alkylaminocarbonyl, di-($C_{1-3}$-alkyl)-aminocarbonyl, $C_{3-6}$-cycloalkyleneiminocarbonyl, amino, $C_{1-3}$-alkylamino, di-($C_{1-3}$-alkyl)-amino, $C_{1-3}$-alkylcarbonylamino, or $C_{1-3}$-alkylsulphonylamino group, a phenyl, or C-linked heteroaryl group while the heteroaryl group is selected from among pyrrolyl, oxazolyl, imidazolyl, furanyl, thiophenyl, thiazolyl, 1,2,3-triazolyl, 1,2,4-triazolyl, tetrazolyl, pyridinyl, pyrimidinyl and pyrazinyl, and which may optionally be mono- to disubstituted in the heteroaryl moiety by identical or different substituents selected from among halogen atoms, $C_{1-3}$-alkyl, hydroxy, $C_{1-3}$-alkyloxy, mono-, di- and trifluoromethoxy groups, a phenyl-$C_{1-3}$-alkyl, heteroaryl-$C_{1-3}$-alkyl- group, while the heteroaryl group is selected from among pyrrolyl, oxazolyl, imidazolyl, furanyl, thiophenyl, thiazolyl, 1,2,3-triazolyl, 1,2,4-triazolyl, tetrazolyl, pyridinyl, pyrimidinyl and pyrazinyl, and which may optionally be mono- to disubstituted in the heteroaryl moiety by identical or different substituents selected from among halogen atoms, $C_{1-3}$-alkyl, hydroxy, $C_{1-3}$-alkyloxy, mono-, di- and trifluoromethoxy groups, and which may optionally be substituted in the $C_{1-3}$-alkyl moiety by a hydroxy, a $C_{1-3}$-alkyloxy group, while the hydrogen atoms of the $C_{1-3}$-alkyloxy group may optionally be wholly or partly replaced by fluorine atoms, a $C_{1-5}$-alkylcarbonyloxy, or a $C_{1-5}$-alkyloxycarbonyloxy group;

$R^9$ denotes a straight-chain or branched $C_{1-4}$-alkyl group, while the hydrogen atoms of the straight-chain or branched $C_{1-4}$-alkyl group may optionally be wholly or partly replaced by fluorine atoms, and which may optionally be substituted by a hydroxy, a $C_{1-3}$-alkyloxy group, while the hydrogen atoms of the $C_{1-3}$-alkyloxy group may optionally be wholly or partly replaced by fluorine atoms, a benzyloxy, $C_{1-3}$-alkyloxycarbonyl, aminocarbonyl, $C_{1-3}$-alkylaminocarbonyl, di-($C_{1-3}$-alkyl)-aminocarbonyl, $C_{3-6}$-cycloalkyleneiminocarbonyl, amino, $C_{1-3}$-alkylamino, di-($C_{1-3}$-alkyl)-amino, $C_{1-3}$-alkylcarbonylamino, $C_{1-3}$-alkyl-sulphonylamino group, with the proviso that the replacement of hydrogen atoms of the first carbon atom of the straight-chain or branched $C_{1-4}$-alkyl group by substituents from the group comprising oxygen, sulphur or nitrogen is excluded, a phenyl, phenyl-$C_{1-2}$-alkyl, heteroaryl-$C_{1-2}$-alkyl or C-linked heteroaryl group while the heteroaryl group is selected from among pyrrolyl, oxazolyl, imidazolyl, furanyl, thiophenyl, thiazolyl, 1,2,3-triazolyl, 1,2,4-triazolyl, tetrazolyl, pyridinyl, pyrimidinyl and pyrazinyl, and which may optionally be mono- to disubstituted in the heteroaryl moiety by identical or different substituents selected from among halogen atoms, $C_{1-3}$-alkyl, hydroxy, $C_{1-3}$-alkyloxy, mono-, di- and trifluoromethoxy groups, B denotes a group of general formula

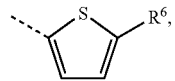

$R^6$ denotes a hydrogen, a chlorine or bromine atom, an ethynyl, a methyl or a methoxy group, while, unless otherwise stated, by the term "halogen atom" mentioned hereinbefore in the definitions is meant an atom selected from among fluorine, chlorine, bromine and iodine, while the alkyl, alkenyl, alkynyl and alkoxy groups contained in the above-mentioned definitions which have more than two carbon atoms, unless otherwise stated, may be straight-chain or branched and the alkyl groups in the previously mentioned dialkylated groups, for example the dialkylamino groups, may be identical or different, and the hydrogen atoms of the methyl or ethyl groups contained in the foregoing definitions, unless otherwise stated, may be wholly or partly replaced by fluorine atoms, the tautomers, the enantiomers, the diastereomers, the mixtures thereof and the salts thereof.

A sixth embodiment of the present invention includes those compounds of general formula I wherein A denotes a group of general formula

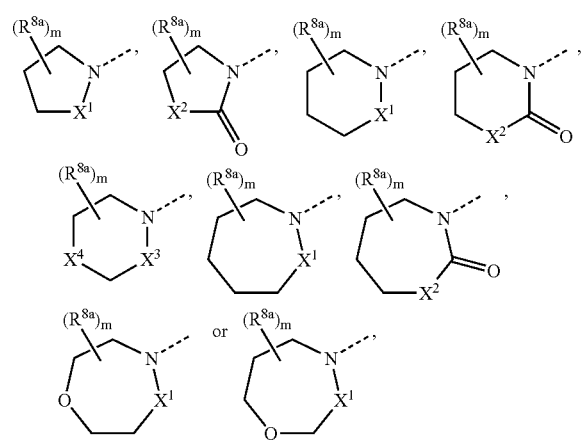

wherein m is the number 1 or 2, $R^{8a}$ each independently of one another denote a hydrogen or fluorine atom or a $C_{1-3}$-alkyl, hydroxy, hydroxy-$C_{1-3}$-alkyl, $C_{1-3}$-alkoxy, $C_{1-3}$-alkoxy-$C_{1-3}$-alkyl, amino, $C_{1-3}$-alkylamino, di-($C_{1-3}$-alkyl)-amino, amino-$C_{1-3}$-alkyl, $C_{1-3}$-alkylamino-$C_{1-3}$-alkyl, or di-($C_{1-3}$-alkyl)-amino-$C_{1-3}$-alkyl group, while in the previously mentioned substituted 5- to 7-membered groups A the heteroatoms F, O or N optionally introduced with $R^{8a}$ as substituents are not separated by precisely one carbon atom from a heteroatom selected from among N, O and S, $R^{8b}$ each independently of one another denote a hydrogen atom or a $C_{1-3}$-alkyl group, $R^{8c}$ each independently of one another denote a hydrogen atom, a $C_{1-3}$-alkyl, $C_{1-3}$-alkylcarbonyl, $C_{1-3}$-alkyloxycarbonyl or $C_{1-3}$-alkylsulphonyl group, $X^1$ denotes a carbonyl or sulphonyl group, $X^2$ denotes an oxygen atom or an —$NR^{8b}$ group, $X^3$ denotes a carbonyl or sulphonyl group, $X^4$ denotes an oxygen atom or an —$NR^{8c}$ group, $R^1$ denotes a hydrogen, fluorine, chlorine or bromine atom, a methyl, trifluoromethyl or methoxy group, $R^2$ denotes a hydrogen atom, X denotes a nitrogen atom or a CH group, $R^3$ denotes a hydrogen atom or a methyl group, $R^4$ denotes a hydrogen atom, $R^5$ denotes a hydrogen atom, a hydroxy group, a $OR^9$ group, an allyl or methallyl group, a methyl group which may optionally be substituted independently of one another by a $C_{1-3}$-alkyl, hydroxy, $OR^9$ group, aminocarbonyl, pyridin-4-yl, pyridin-3-yl, pyridin-2-yl, pyrazin-2-yl, pyrazin-3-yl or phenyl group, a phenyl group, $R^9$ a straight-chain or branched $C_{1-4}$-alkyl group, which may optionally be substituted by a hydroxy, a $C_{1-3}$-alkoxy group, a benzyloxy or a di-($C_{1-3}$-alkyl)-amino group, with the proviso that the replacement of hydrogen atoms of the first carbon atom of the straight-chain or branched $C_{1-4}$-alkyl group by substituents from the group comprising oxygen or nitrogen is excluded, B denotes a group of general formula

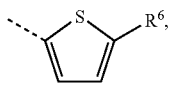

$R^6$ denotes a chlorine or bromine atom or an ethynyl group, while, unless otherwise stated, by the term "halogen atom" mentioned hereinbefore in the definitions is meant an atom selected from among fluorine, chlorine, bromine and iodine, while the alkyl, alkenyl, alkynyl and alkoxy groups contained in the above-mentioned definitions which have more than two carbon atoms, unless otherwise stated, may be straight-chain or branched and the alkyl groups in the previously mentioned dialkylated groups, for example the dialkylamino groups, may be identical or different, and the hydrogen atoms of the methyl or ethyl groups contained in the foregoing definitions, unless otherwise stated, may be wholly or partly replaced by fluorine atoms, the tautomers, the enantiomers, the diastereomers, the mixtures thereof and the salts thereof.

A seventh embodiment of the present invention includes those compounds of general formula I, wherein the group B denotes the group

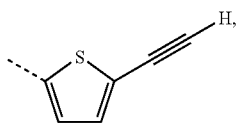

the tautomers, the enantiomers, the diastereomers, the mixtures thereof and the salts thereof.

An eighth embodiment of the present invention includes those compounds of general formula I, wherein the group B denotes the group

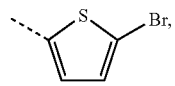

the tautomers, the enantiomers, the diastereomers, the mixtures thereof and the salts thereof.

A ninth embodiment of the present invention includes those compounds of general formula I, wherein the group A denotes the group

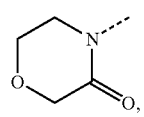

the tautomers, the enantiomers, the diastereomers, the mixtures thereof and the salts thereof.

Within the scope of the present application, unless otherwise defined, the following general expressions used in the definitions are defined more specifically as shown below or are represented by examples.

Examples of the monocyclic heteroaryl groups mentioned hereinbefore in the definitions are the pyridyl, N-oxy-pyridyl, pyrazolyl, pyridazinyl, pyrimidinyl, pyrazinyl, [1,2,3]triazinyl, [1,3,5]triazinyl, [1,2,4]triazinyl, pyrrolyl, imidazolyl, [1,2,4]triazolyl, [1,2,3]triazolyl, tetrazolyl, furanyl, isoxazolyl, oxazolyl, [1,2,3]oxadiazolyl, [1,2,4]oxadiazolyl, furazanyl, thiophenyl, thiazolyl, isothiazolyl, [1,2,3]thiadiazolyl, [1,2,4]thiadiazolyl or [1,2,5]thiadiazolyl group.

Examples of the bicyclic heteroaryl groups mentioned hereinbefore in the definitions are the benzimidazolyl, benzofuranyl, benzo[c]furanyl, benzothiophenyl, benzo[c]thiophenyl, benzothiazolyl, benzo[c]isothiazolyl, benzo[d]isothiazolyl, benzooxazolyl, benzo[c]isoxazolyl, benzo[d]isoxazolyl, benzo[1,2,5]oxadiazolyl, benzo[1,2,5]thiadiazolyl, benzo[1,2,3]thiadiazolyl, benzo[d][1,2,3]triazinyl, benzo[1,2,4]triazinyl, benzotriazolyl, cinnolinyl, quinolinyl, N-oxy-quinolinyl, isoquinolinyl, quinazolinyl, N-oxy-quinazolinyl, quinoxalinyl, phthalazinyl, indolyl, isoindolyl or 1-oxa-2,3-diaza-indenyl group.

Examples of the $C_{1-6}$-alkyl groups mentioned hereinbefore in the definitions are the methyl, ethyl, 1-propyl, 2-propyl, n-butyl, sec-butyl, tert-butyl, 1-pentyl, 2-pentyl, 3-pentyl, neo-pentyl, 3-methyl-2-butyl, 1-hexyl, 2-hexyl, 3-hexyl, 3-methyl-2-pentyl, 4-methyl-2-pentyl, 3-methyl-3-pentyl, 2-methyl-3-pentyl, 2,2-dimethyl-3-butyl or 2,3-dimethyl-2-butyl group.

Examples of the $C_{1-5}$-alkyloxy groups mentioned hereinbefore in the definitions are the methyloxy, ethyloxy, 1-propyloxy, 2-propyloxy, n-butyloxy, sec-butyloxy, tert-butyloxy, 1-pentyloxy, 2-pentyloxy, 3-pentyloxy or neo-pentyloxy group.

Examples of the $C_{2-6}$-alkenyl groups mentioned hereinbefore in the definitions are the ethenyl, 1-propen-1-yl, 2-propen-1-yl, 1-buten-1-yl, 2-buten-1-yl, 3-buten-1-yl, 1-penten-1-yl, 2-penten-1-yl, 3-penten-1-yl, 4-penten-1-yl, 1-hexen-1-yl, 2-hexen-1-yl, 3-hexen-1-yl, 4-hexen-1-yl, 5-hexen-1-yl, but-1-en-2-yl, but-2-en-2-yl, but-1-en-3-yl, 2-methyl-prop-2-en-1-yl, pent-1-en-2-yl, pent-2-en-2-yl, pent-3-en-2-yl, pent-4-en-2-yl, pent-1-en-3-yl, pent-2-en-3-yl, 2-methyl-but-1-en-1-yl, 2-methyl-but-2-en-1-yl, 2-methyl-but-3-en-1-yl, 2-ethyl-prop-2-en-1-yl, hex-1-en-2-yl, hex-2-en-2-yl, hex-3-en-2-yl, hex-4-en-2-yl, hex-5-en-2-yl, hex-1-en-3-yl, hex-2-en-3-yl, hex-3-en-3-yl, hex-4-en-3-yl, hex-5-en-3-yl, hex-1-en-4-yl, hex-2-en-4-yl, hex-3-en-4-yl, hex-4-en-4-yl, hex-5-en-4-yl, 4-methyl-pent-1-en-3-yl, 3-methyl-pent-1-en-3-yl, 2-methyl-pent-1-en-3-yl, 2,3-di methyl-but-1-en-3-yl, 3,3-dimethyl-but-1-en-2-yl or 2-ethyl-but-1-en-3-yl group, Examples of the $C_{2-6}$-alkynyl groups mentioned hereinbefore in the definitions are the ethynyl, 1-propynyl, 2-propynyl, 1-butyn-1-yl, 1-butyn-3-yl, 2-butyn-1-yl, 3-butyn-1-yl, 1-pentyn-1-yl, 1-pentyn-3-yl, 1-pentyn-4-yl, 2-pentyn-1-yl, 2-pentyn-3-yl, 3-pentyn-1-yl, 4-pentyn-1-yl, 2-methyl-1-butyn-4-yl, 3-methyl-1-butyn-1-yl, 3-methyl-1-butyn-3-yl, 1-hexyn-1-yl, 2-hexyn-1-yl, 3-hexyn-1-yl, 4-hexyn-1-yl, 5-hexyn-1-yl, 1-hexyn-3-yl, 1-hexyn-4-yl, 1-hexyn-5-yl, 2-hexyn-4-yl, 2-hexyn-5-yl, 3-hexyn-5-yl, 3-methyl-1-pentyn-3-yl, 4-methyl-1-pentyn-3-yl, 3-methyl-1-pentyn-4-yl, 4-methyl-1-pentyn-4-yl, 4-methyl-2-pentyn-4-yl, 4-methyl-2-pentyn-1-yl, 2,2-dimethyl-3-butyn-1-yl or 2-ethyl-3-butyn-1-yl group.

By a group which can be converted in vivo into a carboxy group is meant for example a carboxy group esterified with an alcohol wherein the alcoholic moiety is preferably a $C_{1-6}$-alkanol, a phenyl-$C_{1-3}$-alkanol, a $C_{3-9}$-cycloalkanol, a $C_{5-7}$-cycloalkenol, a $C_{3-5}$-alkenol, a phenyl-$C_{3-5}$-alkenol, a $C_{3-5}$-alkynol or phenyl-$C_{3-5}$-alkynol with the proviso that no bond to the oxygen atom starts from a carbon atom that carries a double or triple bond, a $C_{3-8}$-cycloalkyl-$C_{1-3}$-alkanol or an alcohol of formula

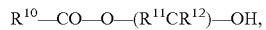

$R^{10}$—CO—O—($R^{11}CR^{12}$)—OH, wherein $R^{10}$ denotes a $C_{1-8}$-alkyl, $C_{5-7}$-cycloalkyl, phenyl or phenyl-$C_{1-3}$-alkyl group, $R^{11}$ denotes a hydrogen atom, a $C_{1-3}$-alkyl, $C_{5-7}$-cycloalkyl or phenyl group and $R^{12}$ denotes a hydrogen atom or a $C_{1-3}$-alkyl group.

Preferred groups which may be cleaved from a carboxy group in vivo include a $C_{1-6}$-alkoxy group such as the methoxy, ethoxy, n-propyloxy, isopropyloxy, n-butyloxy, n-pentyloxy, n-hexyloxy or cyclohexyloxy group or a phenyl-$C_{1-3}$-alkoxy group such as the benzyloxy group.

By a group which may be converted in vivo into a hydroxyl group is meant for example a hydroxyl group esterified with a carboxylic acid wherein the carboxylic acid moiety is preferably a $C_{1-7}$-alkanoic acid, a phenyl-$C_{1-3}$-alkanoic acid, a $C_{3-9}$-cycloalkylcarboxylic acid, a $C_{5-7}$-cycloalkenecarboxylic acid, a $C_{3-7}$-alkenoic acid, a phenyl-$C_{3-5}$-alkenoic acid, a $C_{3-7}$-alkynoic acid or phenyl-$C_{3-5}$-alkynoic acid, while individual methylene groups of the carboxylic acid group may be replaced by oxygen atoms, with the proviso that no bond to the oxygen atom starts from a carbon atom which carries a double or triple bond.

Preferred groups which may be cleaved from a hydroxyl group in vivo include a $C_{1-7}$-acyl group such as the formyl, acetyl, n-propionyl, isopropionyl, n-propanoyl, n-butanoyl, n-pentanoyl, n-hexanoyl or cyclohexylcarbonyl group or a benzoyl group as well as a methoxyacetyl, 1-methoxypropionyl, 2-methoxypropionyl or 2-methoxy-ethoxyacetyl group.

Those compounds of general formula I wherein A, $R^4$ and/or $R^5$ contains a group which can be converted in vivo into a carboxy or hydroxyl group are prodrugs for those compounds of general formula I wherein A, $R^4$ and/or $R^5$ contains a carboxy or hydroxyl group.

The following preferred compounds of general formula I will now be mentioned by way of example:

(1) 5-bromo-thiophene-2-carboxylic acid-{1-[3-chloro-4-(2-oxo-[1,3]oxazinan-3-yl)-phenyl]-5-oxo-pyrrolidin-3-yl}-amide (2) (R)-5-bromo-thiophene-2-carboxylic acid-{1-[2-fluoro-4-(3-oxo-morpholin-4-yl)-phenyl]-5-oxo-pyrrolidin-3-yl}-amide (3) 5-chloro-thiophene-2-carboxylic acid-{1-[3-methyl-4-(3-oxo-morpholin-4-yl)-phenyl]-5-oxo-pyrrolidin-3-yl}-amide (4) 5-bromo-thiophene-2-carboxylic acid-{1-[3-methyl-4-(3-oxo-morpholin-4-yl)-phenyl]-5-oxo-pyrrolidin-3-yl}-amide (5) 5-chloro-pyridine-2-carboxylic acid-{1-[3-methyl-4-(3-oxo-morpholin-4-yl)-phenyl]-5-oxo-pyrrolidin-3-yl}-amide (6) 5-methyl-thiophene-2-carboxylic acid-{1-[3-methyl-4-(3-oxo-morpholin-4-yl)-phenyl]-5-oxo-pyrrolidin-3-yl}-amide (7) 5-bromo-thiazole-2-carboxylic acid-{1-[3-methyl-4-(3-oxo-morpholin-4-yl)-phenyl]-5-oxo-pyrrolidin-3-yl}-amide (8) 5-chloro-thiophene-2-carboxylic acid-{1-[3-chloro-4-(2-oxo-[1,3]oxazinan-3-yl)-phenyl]-5-oxo-pyrrolidin-3-yl}-amide (9) (R)-5-bromo-thiophene-2-carboxylic acid-{1-[3-methyl-4-(3-oxo-morpholin-4-yl)-phenyl]-5-oxo-pyrrolidin-3-yl}-amide

(10) (R)-5-bromo-thiophene-2-carboxylic acid-{5-oxo-1-[5-(3-oxo-morpholin-4-yl)-pyridin-2-yl]-pyrrolidin-3-yl}-amide

(11) (S)-5-bromo-thiophene-2-carboxylic acid-{1-[3-methyl-4-(3-oxo-morpholin-4-yl)-phenyl]-5-oxo-pyrrolidin-3-yl}-amide

(12) (R)-5-chloro-thiophene-2-carboxylic acid-{1-[2-fluoro-4-(3-oxo-morpholin-4-yl)-phenyl]-5-oxo-pyrrolidin-3-yl}-amide

(13) 5-bromo-thiophene-2-carboxylic acid-{1-[2-fluoro-4-(2-oxo-2H-pyridin-1-yl)-phenyl]-5-oxo-pyrrolidin-3-yl}-amide

(14) 5-chloro-thiophene-2-carboxylic acid-{1-[2-fluoro-4-(2-oxo-2H-pyridin-1-yl)-phenyl]-5-oxo-pyrrolidin-3-yl}-amide

(15) 2-bromo-thiazole-5-carboxylic acid-{1-[3-chloro-4-(2-oxo-[1,3]-oxazinan-3-yl)-phenyl]-5-oxo-pyrrolidin-3-yl}-amide

(16) 5-bromo-thiophene-2-carboxylic acid-{(3R,4R)-4-methyl-1-[3-methyl-4-(3-oxo-morpholin-4-yl)-phenyl]-5-oxo-pyrrolidin-3-yl}-amide

(17) (R)-5-bromo-thiophene-2-carboxylic acid-{1-[2.5-difluoro-4-(3-oxo-morpholin-4-yl)-phenyl]-5-oxo-pyrrolidin-3-yl}-amide

(18) 5-bromo-thiophene-2-carboxylic acid-{1-[3-methyl-4-(5-oxo-[1,4]oxazepan-4-yl)-phenyl]-5-oxo-pyrrolidin-3-yl}-amide

(19) (R)-5-ethynyl-thiophene-2-carboxylic acid-{1-[3-methyl-4-(3-oxo-morpholin-4-yl)-phenyl]-5-oxo-pyrrolidin-3-yl}-amide

(20) 5-ethynyl-thiophene-2-carboxylic acid-{1-[3-methyl-4-(5-oxo-[1,4]oxazepan-4-yl)-phenyl]-5-oxo-pyrrolidin-3-yl}-amide

(21) 5-bromo-thiophene-2-carboxylic acid-{1-[3-methyl-4-(2-oxo-[1,3]oxazepan-3-yl)-phenyl]-5-oxo-pyrrolidin-3-yl}-amide

(22) 5-ethynyl-thiophene-2-carboxylic acid-{(3R,4R)-4-methyl-1-[3-methyl-4-(3-oxo-morpholin-4-yl)-phenyl]-5-oxo-pyrrolidin-3-yl}-amide
(23) (R)-5-bromo-thiophene-2-carboxylic acid-{1-[6-methyl-5-(3-oxo-morpholin-4-yl)-pyridin-2-yl]-5-oxo-pyrrolidin-3-yl}-amide
(24) (R)-5-bromo-thiophene-2-carboxylic acid-{1-[4-(3-oxo-morpholin-4-yl)-phenyl]-5-oxo-pyrrolidin-3-yl}-amide
(25) (R)-5-ethynyl-thiophene-2-carboxylic acid-{5-oxo-1-[6-methyl-5-(3-oxo-morpholin-4-yl)-pyridin-2-yl]-pyrrolidin-3-yl}-amide
(26) (R)-5-chloro-thiophene-2-carboxylic acid-{1-[6-methyl-5-(3-oxo-morpholin-4-yl)-pyridin-2-yl]-5-oxo-pyrrolidin-3-yl}-amide
(27) (R)-5-ethynyl-thiophene-2-carboxylic acid-{5-oxo-1-[4-(3-oxo-morpholin-4-yl)-phenyl]-pyrrolidin-3-yl}-amide
(28) (R)-5-chloro-thiophene-2-carboxylic acid-{5-oxo-1-[4-(3-oxo-morpholin-4-yl)-phenyl]-pyrrolidin-3-yl}-amide
(29) (R)-4-bromo-thiophene-2-carboxylic acid-{1-[5-oxo-4-(3-oxo-morpholin-4-yl)-phenyl]-pyrrolidin-3-yl}-amide
(30) (R)-5-bromo-thiophene-2-carboxylic acid-{5-oxo-1-[4-(2-oxo-piperidin-1-yl)-phenyl]-pyrrolidin-3-yl}-amide
(31) (R)-5-ethynyl-thiophene-2-carboxylic acid-{5-oxo-1-[4-(2-oxo-piperidin-1-yl)-phenyl]-pyrrolidin-3-yl}-amide
(32) (R)-5-ethynyl-thiophene-2-carboxylic acid-{5-oxo-1-[4-(3-oxo-morpholin-4-yl)-3-trifluoromethyl-phenyl]-pyrrolidin-3-yl}-amide
(33) (R)-5-bromo-thiophene-2-carboxylic acid-{5-oxo-1-[4-(3-oxo-morpholin-4-yl)-3-trifluoromethyl-phenyl]-pyrrolidin-3-yl}-amide
(34) (R)-5-chloro-thiophene-2-carboxylic acid-{5-oxo-1-[4-(3-oxo-morpholin-4-yl)-3-trifluoromethyl-phenyl]-pyrrolidin-3-yl}-amide
(35) (R)-5-chloro-thiophene-2-carboxylic acid-{1-[4-(1,1-dioxo-1$\square^6$-[1,2]thiazinan-2-yl)-phenyl]-5-oxo-pyrrolidin-3-yl}-amide
(36) (R)-5-bromo-thiophene-2-carboxylic acid-{1-[4-(1,1-dioxo-1$\square^6$-[1,2]thiazinan-2-yl)-phenyl]-5-oxo-pyrrolidin-3-yl}-amide
(37) (R)-5-ethynyl-thiophene-2-carboxylic acid-{1-[4-(1,1-dioxo-1$\square^6$-[1,2]thiazinan-2-yl)-phenyl]-5-oxo-pyrrolidin-3-yl}-amide
(38) (R)-5-bromo-thiophene-2-carboxylic acid-{1-[3-chloro-4-(2-oxo-tetrahydro-pyrimidin-1-yl)-phenyl]-5-oxo-pyrrolidin-3-yl}-amide
(39) (R)-4-bromo-thiophene-2-carboxylic acid-{1-[4-(1,1-dioxo-1$\square^6$-[1,2,6]thiadiazinan-2-yl)-3-methyl-phenyl]-5-oxo-pyrrolidin-3-yl}-amide
(40) (R)-4-bromo-thiophene-2-carboxylic acid-{1-[3-methyl-4-(3-oxo-[1,4]oxazepan-4-yl)-phenyl]-5-oxo-pyrrolidin-3-yl}-amide
(41) 5-bromo-thiophene-2-carboxylic acid-{1-[3-chloro-4-(4-methyl-[1,4]diazepam-1-yl)-phenyl]-5-oxo-pyrrolidin-3-yl}-amide
(42) 5-chloro-thiophene-2-carboxylic acid-[1-(4-azepan-1-yl-3-chloro-phenyl]-5-oxo-pyrrolidin-3-yl]-amide
(43) 5-ethynyl-thiophene-2-carboxylic acid-{1-[3-methyl-4-(5-oxo-[1,4]oxazepan-4-yl)-phenyl]-5-oxo-pyrrolidin-3-yl}-amide
(44) 5-ethynyl-thiophene-2-carboxylic acid-{1-[3-chloro-4-(2-oxo-azepan-1-yl )-phenyl]-5-oxo-pyrrolidin-3-yl}-amide
(45) 5-chloro-thiophene-2-carboxylic acid-{1-[3-chloro-4-(2-oxo-azepan-1-yl)-phenyl]-5-oxo-pyrrolidin-3-yl}-amide
(46) 5-bromo-thiophene-2-carboxylic acid-{(3R,4S)-4-hydroxy-1-[3-methyl-4-(3-oxo-morpholin-4-yl)-phenyl]-5-oxo-pyrrolidin-3-yl}-amide
(47) (R)-5-bromo-thiophene-2-carboxylic acid-{1-[3-chloro-4-(3-oxo-morpholin-4-yl)-phenyl]-5-oxo-pyrrolidin-3-yl}-amide,
(48) (R)-5-bromo-furan-2-carboxylic acid-{1-[3-methyl-4-(3-oxo-morpholin-4-yl)-phenyl]-5-oxo-pyrrolidin-3-yl}-amide,
(49) (R)-5-chloro-thiophene-2-carboxylic acid-{1-[3-chloro-4-(3-oxo-morpholin-4-yl)-phenyl]-5-oxo-pyrrolidin-3-yl}-amide,
(50) (R)-5-bromo-thiophene-2-carboxylic acid-{1-[3-bromo-4-(3-oxo-morpholin-4-yl)-phenyl]-5-oxo-pyrrolidin-3-yl}-amide,
(51) (R)-5-bromo-thiophene-2-carboxylic acid-{1-[3-fluoro-4-(3-oxo-morpholin-4-yl)-phenyl]-5-oxo-pyrrolidin-3-yl}-amide,
(52) (R)-5-chloro-1H-indole-6-carboxylic acid-{1-[3-methyl-4-(3-oxo-morpholin-4-yl)-phenyl]-5-oxo-pyrrolidin-3-yl}-amide,
(53) (R)-5-bromo-thiophene-2-carboxylic acid-{1-[2-methyl-4-(3-oxo-morpholin-4-yl)-phenyl]-5-oxo-pyrrolidin-3-yl}-amide,
(54) (R)-5-chloro-naphthalene-2-carboxylic acid-{1-[3-methyl-4-(3-oxo-morpholin-4-yl)-phenyl]-5-oxo-pyrrolidin-3-yl}-amide,
(55) (R)-5-bromo-thiophene-2-carboxylic acid-{1-[4-(3-oxo-morpholin-4-yl)-3-trifluoromethoxy-phenyl]-5-oxo-pyrrolidin-3-yl}-amide,
(56) (R)-5-chloro-1H-indole-2-carboxylic acid-{1-[3-methyl-4-(3-oxo-morpholin-4-yl)-phenyl]-5-oxo-pyrrolidin-3-yl}-amide,
(57) (R)-5-bromo-thiophene-2-carboxylic acid-{1-[3-methoxy-4-(3-oxo-morpholin-4-yl)-phenyl]-5-oxo-pyrrolidin-3-yl}-amide,
(58) (R)-5-chloro-benzo[b]thiophene-2-carboxylic acid-{1-[3-methyl-4-(3-oxo-morpholin-4-yl)-phenyl]-5-oxo-pyrrolidin-3-yl}-amide,
(59) (R)-5-bromo-thiophene-2-carboxylic acid-{1-[3-nitro-4-(3-oxo-morpholin-4-yl)-phenyl]-5-oxo-pyrrolidin-3-yl}-amide,
(60) (R)-5-bromo-thiophene-2-carboxylic acid-{1-[3-amino-4-(3-oxo-morpholin-4-yl)-phenyl]-5-oxo-pyrrolidin-3-yl}-amide,
(61) (R)-5-chloro-1H-benzimidazole-2-carboxylic acid-{1-[3-methyl-4-(3-oxo-morpholin-4-yl)-phenyl]-5-oxo-pyrrolidin-3-yl}-amide,
(62) 5-bromo-thiophene-2-carboxylic acid-{4-methoxy-1-[3-methyl-4-(3-oxo-morpholin-4-yl)-phenyl]-5-oxo-pyrrolidin-3-yl}-amide,
(63) 5-ethynyl-thiophene-2-carboxylic acid-{4-methoxy-1-[3-methyl-4-(3-oxo-morpholin-4-yl)-phenyl]-5-oxo-pyrrolidin-3-yl}-amide,
(64) 5-bromo-thiophene-2-carboxylic acid-{4-methoxy-1-[3-chloro-4-(3-oxo-morpholin-4-yl)-phenyl]-5-oxo-pyrrolidin-3-yl}-amide,
(65) 5-bromo-thiophene-2-carboxylic acid-{4-methoxy-1-[4-(3-oxo-morpholin-4-yl)-phenyl]-5-oxo-pyrrolidin-3-yl}-amide,
(66) 5-bromo-thiophene-2-carboxylic acid-{4-benzyl-1-[3-methyl-4-(3-oxo-morpholin-4-yl)-phenyl]-5-oxo-pyrrolidin-3-yl}-amide

(67) 5-bromo-thiophene-2-carboxylic acid-{1-[3-chloro-4-(3-oxo-morpholin-4-yl)-phenyl]-5-oxo-4-pyridin-4-ylmethyl-pyrrolidin-3-yl}-amide
(68) 5-bromo-thiophene-2-carboxylic acid-{1-[3-chloro-4-(3-oxo-morpholin-4-yl)-phenyl]-5-oxo-4-pyridin-3-ylmethyl-pyrrolidin-3-yl}-amide
(69) 5-bromo-thiophene-2-carboxylic acid-{1-[3-chloro-4-(3-oxo-morpholin-4-yl)-phenyl]-5-oxo-4-pyridin-2-ylmethyl-pyrrolidin-3-yl}-amide
(70) 5-bromo-thiophene-2-carboxylic acid-{1-[3-chloro-4-(3-oxo-morpholin-4-yl)-phenyl]-4-methyl-5-oxo-pyrrolidin-3-yl}-amide
(71) 5-bromo-thiophene-2-carboxylic acid-{4-isobutyl-1-[3-methyl-4-(3-oxo-morpholin-4-yl)-phenyl]-5-oxo-pyrrolidin-3-yl}-amide
(72) 5-bromo-thiophene-2-carboxylic acid-{4-carbamoylmethyl-5-oxo-1-[3-methyl-4-(3-oxo-morpholin-4-yl)-phenyl]-pyrrolidin-3-yl}-amide
(73) 5-bromo-thiophene-2-carboxylic acid-{4-methyl-5-oxo-1-[4-(3-oxo-morpholin-4-yl)-phenyl]-pyrrolidin-3-yl}-amide
(74) 5-bromo-thiophene-2-carboxylic acid-{4-methyl-1-[6-methyl-5-(3-oxo-morpholin-4-yl)-pyridin-2-yl]-5-oxo-pyrrolidin-3-yl}-amide
(75) 5-bromo-thiophene-2-carboxylic acid-{5-oxo-1-[4-(3-oxo-morpholin-4-yl)-3-trifluoromethoxy-phenyl]-4-prop-2-ynyl-pyrrolidin-3-yl}-amide
(76) 5-bromo-thiophene-2-carboxylic acid-{4-allyl-1-[3-chloro-4-(3-oxo-morpholin-4-yl)-phenyl]-5-oxo-pyrrolidin-3-yl}-amide
(77) 5-bromo-thiophene-2-carboxylic acid-{5-[3-methyl-4-(3-oxo-morpholin-4-yl)-phenyl]-4-oxo-5-aza-spiro[2.4]hept-7-yl}-amide
(78) 5-ethynyl-thiophene-2-carboxylic acid-{3-methyl-1-[3-methyl-4-(3-oxo-morpholin-4-yl)-phenyl]-5-oxo-pyrrolidin-3-yl}-amide,
(79) 5-bromo-thiophene-2-carboxylic acid-{3-methyl-1-[3-methyl-4-(3-oxo-morpholin-4-yl)-phenyl]-5-oxo-pyrrolidin-3-yl}-amide,
(80) 5-bromo-thiophene-2-carboxylic acid-{3,4-dimethyl-1-[3-methyl-4-(3-oxo-morpholin-4-yl)-phenyl]-5-oxo-pyrrolidin-3-yl}-amide,
(81) 5-bromo-thiophene-2-carboxylic acid-{3-propyl-1-[3-methyl-4-(3-oxo-morpholin-4-yl)-phenyl]-5-oxo-pyrrolidin-3-yl}-amide,
(82) 5-bromo-thiophene-2-carboxylic acid-{3-methyl-5-oxo-1-[4-(3-oxo-morpholin-4-yl)-phenyl]-pyrrolidin-3-yl}-amide,
(83) 5-ethynyl-thiophene-2-carboxylic acid-{3-methyl-5-oxo-1-[5-(3-oxo-morpholin-4-yl)-pyridin-2-yl]-pyrrolidin-3-yl}-amide,
(84) 5-ethynyl-thiophene-2-carboxylic acid-{3-methyl-1-[6-methyl-5-(3-oxo-morpholin-4-yl)-pyridin-2-yl]-5-oxo-pyrrolidin-3-yl}-amide,
(85) 5-bromo-thiophene-2-carboxylic acid-{4-dimethylaminocarbamoylmethyl-3-methyl-1-[3-methyl-4-(3-oxo-morpholin-4-yl)-phenyl]-5-oxo-pyrrolidin-3-yl}-amide,
(86) (R)-5-bromo-thiophene-2-carboxylic acid-{1-[3-chloro-4-(5-oxo-[1,4]oxazepan-4-yl)-phenyl]-5-oxo-pyrrolidin-3-yl}-amide
(87) (R)-5-chloro-thiophene-2-carboxylic acid-{1-[3-methyl-4-(5-oxo-[1,4]oxazepan-4-yl)-phenyl]-5-oxo-pyrrolidin-3-yl}-amide
(88) (R)-5-bromo-thiophene-2-carboxylic acid-{1-[6-methyl-5-(5-oxo-[1,4]oxazepan-4-yl)-pyridin-2-yl]-5-oxo-pyrrolidin-3-yl}-amide
(89) (R)-5-ethynyl-thiophene-2-carboxylic acid-{1-[6-methyl-5-(5-oxo-[1,4]oxazepan-4-yl)-pyridin-2-yl]-5-oxo-pyrrolidin-3-yl}-amide
(90) (R)-5-bromo-thiophene-2-carboxylic acid-{5-oxo-1-[4-(5-oxo-[1,4]oxazepan-4-yl)-phenyl]-pyrrolidin-3-yl}-amide
(91) (R)-5-bromo-thiophene-2-carboxylic acid-{4-methyl-1-[3-methyl-4-(5-oxo-[1,4]oxazepan-4-yl)-phenyl]-5-oxo-pyrrolidin-3-yl}-amide
(92) (R)-5-bromo-thiophene-2-carboxylic acid-{4-methoxy-1-[3-methyl-4-(5-oxo-[1,4]oxazepan-4-yl)-phenyl]-5-oxo-pyrrolidin-3-yl}-amide
(93) (R)-5-bromo-thiophene-2-carboxylic acid-{4-hydroxy-1-[3-methyl-4-(5-oxo-[1,4]oxazepan-4-yl)-phenyl]-5-oxo-pyrrolidin-3-yl}-amide
(94) 5-bromo-thiophene-2-carboxylic acid-{4-ethoxy-1-[3-methyl-4-(5-oxo-[1,4]oxazepan-4-yl)-phenyl]-5-oxo-pyrrolidin-3-yl}-amide
(95) 5-bromo-thiophene-2-carboxylic acid-{3-methyl-5-oxo-1-[4-(5-oxo-[1,4]oxazepan-4-yl)-phenyl]-pyrrolidin-3-yl}-amide
(96) 5-bromo-thiophene-2-carboxylic acid-{3-methyl-1-[3-methyl-4-(5-oxo-[1,4]oxazepan-4-yl)-phenyl]-5-oxo-pyrrolidin-3-yl}-amide
(97) 5-ethynyl-thiophene-2-carboxylic acid-{3-methyl-1-[3-methyl-4-(5-oxo-[1,4]oxazepan-4-yl)-phenyl]-5-oxo-pyrrolidin-3-yl}-amide
(98) 5-ethynyl-thiophene-2-carboxylic acid-{4-methoxy-1-[3-methyl-4-(5-oxo-[1,4]oxazepan-4-yl)-phenyl]-5-oxo-pyrrolidin-3-yl}-amide
(99) 5-bromo-thiophene-2-carboxylic acid-{4-(2-methoxy-ethoxy)-1-[3-methyl-4-(5-oxo-[1,4]oxazepan-4-yl)-phenyl]-5-oxo-pyrrolidin-3-yl}-amide
(100) 5-ethynyl-thiophene-2-carboxylic acid-{1-[3-methyl-4-(2-oxo-tetrahydropyrimidin-1-yl)-phenyl]-5-oxo-pyrrolidin-3-yl}-amide
(101) (R)-5-bromo-thiophene-2-carboxylic acid-{1-[4-(1,1-dioxo-1λ$^6$-[1,2]thiazinan-2-yl)-3-methyl-phenyl]-5-oxo-pyrrolidin-3-yl}-amide
(102) 5-bromo-thiophene-2-carboxylic acid-{1-[4-(1-dioxo-1λ$^6$-[1,2,6]thiadiazinan-2-yl)-3-methyl-phenyl]-5-oxo-pyrrolidin-3-yl}-amide
(103) (R)-5-bromo-thiophene-2-carboxylic acid-{1-[3-methyl-4-(4-methyl-2-oxo-piperazin-1-yl)-phenyl]-5-oxo-pyrrolidin-3-yl}-amide
(104) (R)-5-bromo-thiophene-2-carboxylic acid-{1-[3-chloro-4-(2-oxo-pyrrolidin-1-yl)-phenyl]-5-oxo-pyrrolidin-3-yl}-amide
(105) 5-bromo-thiophene-2-carboxylic acid-{1-[3-bromo-4-(4-methyl-2-oxo-oxazolidin-3-yl)-phenyl]-4-methyl-5-oxo-pyrrolidin-3-yl}-amide
(106) (R)-5-bromo-thiophene-2-carboxylic acid-{1-[4-(1,1-dioxo-1λ$^6$-isothiazolidin-2-yl)-3-methyl-phenyl]-5-oxo-pyrrolidin-3-yl}-amide
(107) 5-bromo-thiophene-2-carboxylic acid-{1-[4-(1,1-dioxo-1λ$^6$-[1,2,5]thiadiazolidin-2-yl)-3-methoxy-phenyl]-5-oxo-pyrrolidin-3-yl}-amide
(108) 5-bromo-thiophene-2-carboxylic acid-{1-[4-(3-methyl-2-oxo-tetrahydropyrimidin-1-yl)-phenyl]-5-oxo-pyrrolidin-3-yl}-amide
(109) 5-bromo-thiophene-2-carboxylic acid-{1-[3-methyl-4-(3-oxo-thiomorpholin-4-yl)-phenyl]-5-oxo-pyrrolidin-3-yl}-amide
(110) 5-bromo-thiophene-2-carboxylic acid-{1-[3-methyl-4-(3-methyl-5-oxo-thiomorpholin-4-yl)-phenyl]-5-oxo-pyrrolidin-3-yl}-amide (111) (R)-5-bromo-thiophene-2-carboxylic acid-{1-[4-(1,1-dioxo-1☐⁶-[1,2]thiazepan-2-yl)-3-methyl-phenyl]-5-oxo-pyrrolidin-3-yl}-amide
(112) 5-bromo-thiophene-2-carboxylic acid-{3,4-dimethyl-1-[3-methyl-4-(2-oxo-azepan-1-yl)-phenyl]-5-oxo-pyrrolidin-3-yl}-amide
(113) 5-bromo-thiophene-2-carboxylic acid-{1-[3-chloro-4-(2-oxo-[1,3]oxazepan-3-yl)-phenyl]-5-oxo-pyrrolidin-3-yl}-amide
(114) 5-bromo-thiophene-2-carboxylic acid-{1-[3-methyl-4-(4-methyl-7-oxo-[1,4]diazepan-1-yl)-phenyl]-5-oxo-pyrrolidin-3-yl}-amide
(115) 5-bromo-thiophene-2-carboxylic acid-{1-[3-chloro-4-(2-methyl-2-oxo-pyrrolidin-1-yl)-phenyl]-5-oxo-pyrrolidin-3-yl}-amide
(116) 5-bromo-thiophene-2-carboxylic acid-{1-[3-chloro-4-(2-methyl-2-oxo-pyrrolidin-1-yl)-phenyl]-5-oxo-pyrrolidin-3-yl}-amide
(117) 5-bromo-thiophene-2-carboxylic acid-{1-[4-(2-dimethylaminomethyl-5-oxo-pyrrolidin-1-yl)-phenyl]-5-oxo-pyrrolidin-3-yl}-amide
(118) (R)-5-bromo-thiophene-2-carboxylic acid-{1-[3-ethyl-4-(3-oxo-morpholin-4-yl)-phenyl]-5-oxo-pyrrolidin-3-yl}-amide
(119) 5-bromo-thiophene-2-carboxylic acid-{1-[4-(2-imino-piperidin-1-yl)-phenyl]-5-oxo-pyrrolidin-3-yl}-amide
(120) 5-bromo-thiophene-2-carboxylic acid-{1-[4-(2-methoxyimino-piperidin-1-yl)-phenyl]-5-oxo-pyrrolidin-3-yl}-amide
(121) 5-bromo-thiophene-2-carboxylic acid-{1-[3-methyl-4-(3-thioxo-morpholin-4-yl)-phenyl]-5-oxo-pyrrolidin-3-yl}-amide
(122) 5-bromo-thiophene-2-carboxylic acid-{4-hydroxymethyl-1-[3-methyl-4-(3-oxo-morpholin-4-yl)-phenyl]-5-oxo-pyrrolidin-3-yl}-amide
(123) 5-bromo-thiophene-2-carboxylic acid-{4-methoxymethyl-1-[3-methyl-4-(3-oxo-morpholin-4-yl)-phenyl]-5-oxo-pyrrolidin-3-yl}-amide
(124) 5-bromo-thiophene-2-carboxylic acid-{4-(2-hydroxyethyl)-1-[3-methyl-4-(3-oxo-morpholin-4-yl)-phenyl]-5-oxo-pyrrolidin-3-yl}-amide
(125) 5-bromo-thiophene-2-carboxylic acid-{(3R,4R)-1-[3-methyl-4-(3-oxo-morpholin-4-yl)-phenyl]-5-oxo-4-propyl-pyrrolidin-3-yl}-amide
(126) 5-bromo-thiophene-2-carboxylic acid-{(3R,4R)-4-methoxymethyl-1-[3-methyl-4-(3-oxo-morpholin-4-yl)-phenyl]-5-oxo-pyrrolidin-3-yl}-amide
(127) 5-chloro-thiophene-2-carboxylic acid-{(3R,4R)-4-benzyl-1-[3-methyl-4-(3-oxo-morpholin-4-yl)-phenyl]-5-oxo-pyrrolidin-3-yl}-amide
(128) 5-ethynyl-thiophene-2-carboxylic acid-{(3R,4R)-4-benzyl-1-[3-methyl-4-(3-oxo-morpholin-4-yl)-phenyl]-5-oxo-pyrrolidin-3-yl}-amide
(129) 5-chloro-thiophene-2-carboxylic acid-{(3R,4R)-4-methoxymethyl-5-oxo-1-[4-(3-oxo-morpholin-4-yl)-phenyl]-pyrrolidin-3-yl}-amide
(130) 5-chloro-thiophene-2-carboxylic acid-{(3R,4R)-4-allyl-1-[3-methyl-4-(3-oxo-morpholin-4-yl)-phenyl]-5-oxo-pyrrolidin-3-yl}-amide
(131) 5-bromo-thiophene-2-carboxylic acid-{(3R,4R)-4-allyl-1-[3-methyl-4-(3-oxo-morpholin-4-yl)-phenyl]-5-oxo-pyrrolidin-3-yl}-amide
(132) 5-chloro-thiophene-2-carboxylic acid-{(3R,4R)-4-methoxymethyl-1-[3-methyl-4-(3-oxo-morpholin-4-yl)-phenyl]-5-oxo-pyrrolidin-3-yl}-amide
(133) 5-chloro-thiophene-2-carboxylic acid-{3-methyl-1-[3-methyl-4-(3-oxo-morpholin-4-yl)-phenyl]-5-oxo-pyrrolidin-3-yl}-amide
(134) (R)-5-chloro-thiophene-2-carboxylic acid-{1-[3-fluoro-4-(3-oxo-morpholin-4-yl)-phenyl]-5-oxo-pyrrolidin-3-yl}-amide
(135) 5-chloro-thiophene-2-carboxylic acid-(1-{3-chloro-4-[2-(2-diethylamino-ethyl)-piperidin-1-yl]-phenyl}-5-oxo-pyrrolidin-3-yl)-amide
(136) 5-bromo-thiophene-2-carboxylic acid-[1-(3-chloro-4-[1,4]diazepan-1-yl-phenyl)-5-oxo-pyrrolidin-3-yl]-amide
(137) (R)-5-bromo-thiophene-2-carboxylic acid-{1-[4-(1,1-dioxo-1☐⁶-[1,2,6]thiadiazinan-2-yl)-3-methyl-phenyl]-5-oxo-pyrrolidin-3-yl}-amide
(138) (R)-5-bromo-thiophene-2-carboxylic acid-{1-[3-methyl-4-(3-oxo-[1,4]oxazepan-4-yl)-phenyl]-5-oxo-pyrrolidin-3-yl}-amide the tautomers, the enantiomers, the diastereomers, the mixtures thereof and the salts thereof, while the compounds For example the following particularly preferred compounds of general formula I may be mentioned:

(1), (2), (3), (4), (6), (8), (9), (10), (12), (16), (17), (18), (19), (20), (21), (22), (23), (24), (25), (26), (27), (28), (30), (31), (32), (33), (34), (35), (36), (37), (38), (39), (40), (41), (42), (43), (44), (45), (46), (47), (49), (57), (59), (60), (62), (63), (64), (65), (66), (67), (68), (69), (70), (71), (72), (74), (76), (78), (82), (84), (85), (86), (87), (90), (92), (93), (94), (98), (99), (103), (104), (108), (109), (112), (114), (117), (122), (123), (124), (125), (126), (127), (128), (129), (130), (131), (132), (134), (135), (136), (137), (138), the tautomers, the enantiomers, the diastereomers, the mixtures and the salts of which are particularly preferred.

For example the following most particularly preferred compounds of general formula I may be mentioned:

(1), (2), (3), (8), (9), (10), (16), (17), (18), (19), (20), (21), (22), (23), (24), (25), (26), (27), (28), (30), (31), (33), (40), (44), (45), (46), (62), (63), (64), (65), (68), (72), (73), (74), (85), (86), (87), (92), (93), (94), (98), (99), (122), (123), (124), (125), (126), (127), (128), (129), (130), (131), (132), (134), (135), (136), the tautomers, the enantiomers, the diastereomers, the mixtures and the salts of which are particularly preferred.

Within the scope of the present application, if applicable, by the terms "isomer", "stereoisomer", "diastereomer", "enantiomer", "chiral", "racemate" or "racemic mixture" are meant the following. Compounds of the same empirical formula which differ in the nature or arrangement of the bonds of their atoms or their connectivity or the spatial arrangement of the atoms in the molecule, are referred to as "isomers". Isomers which while having the same nature and type of connectivity of their atoms differ in the spatial arrangement of the atoms in the molecule and are not congruent are known as "stereoisomers".

Stereoisomers which do not behave towards one another as image and mirror image are referred to as "diastereomers", and stereoisomers which do behave towards one another as image and mirror image are referred to as "enantiomers". When an asymmetrical centre or atom is present (also referred to as stereocentre or chiral centre), for example in a carbon atom substituted by four different substituents, the molecule is "chiral" in nature and a pair of enantiomers are possible. An enantiomer may be characterised by the absolute configuration of its stereocentre. The absolute configuration is described using the descriptors (R) and (S), which are determined by applying the sequence rules according to Cahn, Ingold and Prelog, or by describing the rotation of the plane of polarised light on interaction with the molecule, which is referred to as dextrorotatory or laevorotatory (i.e. with (+) or (−) as descriptor, accordingly). A chiral compound may occur both as an individual enantiomer or as a mixture of the corresponding enantiomers. A mixture which contains equal amounts of the two enantiomers of a compound is referred to as a "racemate" or "racemic mixture".

According to the invention the compounds of general formula (I) are obtained by methods known per se, for example by the following methods:

(a) In order to prepare a compound of general formula

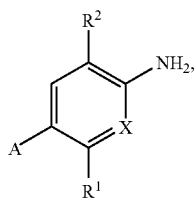

(II)

wherein A, $R^1$ and $R^2$ are defined above:

1) preparing a compound of general formula (II), wherein X, A, $R^1$ and $R^2$ are defined above:

i) reducing the nitro group of a compound of general formula (III)

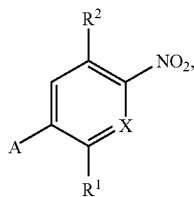

(III)

wherein X, A, $R^1$ and $R^2$ are as defined above.

The reduction of the nitro group is conveniently carried out for example in a solvent or mixture of solvents such as water, aqueous ammonium chloride solution, hydrochloric acid, sulphuric acid, phosphoric acid, formic acid, acetic acid, acetic anhydride with base metals such as iron, zinc, tin or sulphur compounds such as ammonium sulphide, sodium sulphide or sodium dithionite or by catalytic hydrogenation with hydrogen, for example under a pressure of between 0.5 and 100 bar, but preferably between 1and 50 bar, or with hydrazine as reducing agent, conveniently in the presence of a catalyst such as for example Raney nickel, palladium charcoal, platinum oxide, platinum on mineral fibres or rhodium, or with complex hydrides such as lithium aluminium hydride, sodium borohydride, sodium cyanoborohydride, diisobutylaluminium hydride, conveniently in a solvent or mixture of solvents such as water, methanol, ethanol, isopropanol, pentane, hexane, cyclohexane, heptane, benzene, toluene, xylene, ethyl acetate, methylpropionate, glycol, glycoldimethylether, diethyleneglycoldimethylether, dioxane, tetrahydrofuran, N-methylpyrrolidinone, or N-ethyl-diisopropylamine, N-$C_{1-5}$-alkylmorpholine, N-$C_{1-5}$-alkylpiperidine, N-$C_{1-5}$-alkylpyrrolidine, triethylamine, pyridine, for example at temperatures between −30 and 250° C., but preferably between 0 and 150° C.

The compounds of general formula (III) wherein X denotes a CH group may be obtained as follows:

a) Selective oxidation of compounds of general formula (IV):

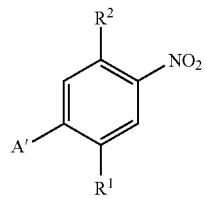

(IV)

wherein A' denotes a substituted cycloalkyleneimino group optionally containing other heteroatoms, and $R^1$ and $R^2$ are as defined above.

The oxidation of a methylene group adjacent to the nitrogen is carried out for example with oxidising agents such as potassium permanganate, potassium chromate, potassium dichromate, chromium(VI)oxide, mercury(II)chloride, selenium(IV)oxide, lead(IV)oxide, lead(II,IV)oxide, potassium peroxomonosulphate, hydrogen peroxide, sodium hypochlorite, optionally in the presence of a suitable catalyst such as nickel(II)chloride, cobalt(II)chloride, ruthenium(III)chloride, osmium(VIII)oxide, vanadium(IV)oxide and/or in the presence of a crown ether such as 18-crown-6, in a solvent or mixture of solvents such as water, formic acid, acetic acid, ethyl acetate, benzene, pyridine, dichloromethane, chloroform, tetrachloromethane, optionally under 2-phase conditions in the presence of a suitable phase transfer catalyst such as for example tetrabutylammonium chloride, tetrabutylammonium bromide, benzyl-triethyl-ammonium chloride or methyl-trioctyl-ammonium chloride, optionally in the presence of an acid such as acetic acid, hydrochloric acid, hydrobromic acid, sulphuric acid, phosphoric acid, sodium hydrogen sulphate, sodium dihydrogen phosphate and/or a base such as sodium hydroxide, potassium hydroxide, ammonia, pyridine, potassium phosphate, dipotassium hydrogen phosphate or sodium acetate at temperatures between −30 and 250° C., but preferably between 0 and 150° C. For example this reaction may be carried out as described in J. H. Markgraf, C. A. Stickney, *J. Heterocycl. Chem.* 2000, 37(1), 109.

The compounds of general formula (IV) may be obtained as follows:

a)i) Nucleophilic substitution with a compound of general formula

A'-H (V), wherein A' denotes a cycloalkyleneimino group optionally containing further heteroatoms, at the aromatic group of general formula

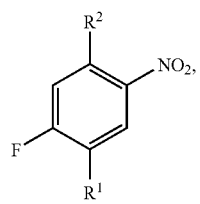

(VI)

wherein $R^1$ and $R^2$ are as defined above.

The nucleophilic substitution is conveniently carried out in a solvent or mixture of solvents such as ethanol, isopropanol, benzene, chlorobenzene, toluene, xylene, glycol, glycoldimethylether, diethyleneglycoldimethylether, dimethylformamide, N-methylpyrrolidinone, tetralin, dimethylsulphoxide, sulpholane, methylene chloride, chloroform, tetrachloromethane or N-ethyl-diisopropylamine, N-$C_{1-5}$-alkylmorpholine, N-$C_{1-5}$-alkylpiperidine, N-$C_{1-5}$-alkylpyrrolidine, triethylamine, pyridine, for example at temperatures between −30 and 250° C., but preferably between 0 and 150° C., if desired conveniently in the presence of bases such as potassium carbonate, sodium carbonate, potassium-tert.-butoxide, sodium ethoxide, potassium hexamethyldisilazane, sodium hydride or lithium diisopropylamide.

a)ii) Transition metal-catalysed coupling reaction of a compound of general formula

A'-H     (V)

wherein A' denotes a cycloalkyleneimino group optionally containing further heteroatoms, at the aromatic group of general formula

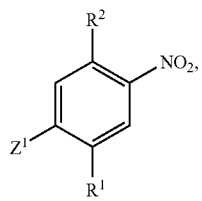

(VII)

wherein $R^1$ and $R^2$ are as defined above and $Z^1$ denotes a chlorine, bromine or iodine atom or a triflate group.

The reaction is expediently carried out in a solvent or mixture of solvents such as benzene, toluene, xylene, tetrahydrofuran, dioxane, diethyl ether, tert.-butyl-methyl-ether, ethyleneglycoldimethylether, diethyleneglycoldimethylether, sulpholane, dimethylformamide, N-methylpyrrolidinone, tetralin, dimethylsulphoxide, methylene chloride, chloroform or tetrachloromethane, for example at temperatures between −30 and 250° C., but preferably between 0 and 150° C., conveniently in the presence of transition metal catalysts such as nickel on activated charcoal, palladium charcoal, tetrakis-(triphenylphosphine)-palladium(0), tris-(dibenzylideneacetone)-dipalladium(0), palladium(II)acetate, palladium(II)chloride, bis-(triphenylphosphine)-palladium(II)-chloride, bis-(tricyclohexylphosphine)-palladium(II)-chloride, bis-(triethylphosphine)-palladium(II)-chloride, bis-(tri-o-tolylphosphine)-palladium(II)-chloride, optionally in the presence of ligands such as triphenylphosphine, tri-o-tolylphosphine, tri-tert.-butylphosphine, 1,3-bis-(diphenylphosphino)-propane, 2,2'-bis-(diphenyl-phosphino)-1,1'-dinaphthyl, 1,1'-bis-(diphenylphosphino)-ferrocene, Xantphos, and conveniently in the presence of a base such as sodium methoxide, sodium ethoxide, sodium-tert.-butoxide, potassium-tert.-butoxide, sodium-tert.-butyldimethyl-silanoate, potassium hexamethyldisilazane, lithium diisopropylamide, potassium carbonate, rubidium carbonate, caesium carbonate, potassium phosphate, sodium hydride, optionally in the presence of a complexing agent such as 18-crown-6-ether as well as conveniently using an inert gas atmosphere (for example nitrogen or argon) and optionally under pressure.

b) Acylation/sulphonylation and alkylation of a compound of general formula

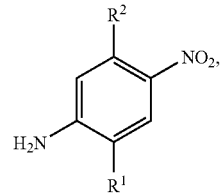

(VIII)

wherein $R^1$ and $R^2$ are as defined above, with a compound of general formula

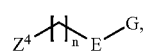

(IX)

wherein E denotes a carbonyl, oxycarbonyl, sulphonyl or a sulphamoyl group optionally substituted at the nitrogen atom as mentioned above, G denotes a chlorine, bromine or iodine atom or an anhydride, $C_{1-5}$-alkoxy or benzotriazoloxy group or E and G together denote an isocyanato or cyano group and $Z^4$ denotes a nucleofugic leaving group, for example a chlorine, bromine or iodine atom, a tosylate, triflate or mesylate group, and n is a number between 2 and 5, while individual methylene groups as described above may additionally be substituted or replaced by heteroatoms, and subsequent intramolecular cyclisation by alkylation of the anilidic nitrogen, thereby cleaving the nucleofugic leaving group $Z^4$.

The acylation/sulphonylation is conveniently carried out in a solvent or mixture of solvents such as benzene, chlorobenzene, toluene, xylene, glycoldimethylether, diethyleneglycoldimethylether, dimethylformamide, N-methylpyrrolidinone, tetralin, dimethylsulphoxide, sulpholane, methylene chloride, chloroform, tetrachloromethane, N-ethyl-diisopropylamine, N-$C_{1-5}$-alkylmorpholine, N-$C_{1-5}$-alkylpiperidine, N-$C_{1-5}$-alkylpyrrolidine, triethylamine, pyridine, for example at temperatures between −30 and 250° C., but preferably between 0 and 150° C., conveniently in the presence of bases such as pyridine, triethylamine, p-dimethylaminopyridine, potassium carbonate, sodium carbonate, potassium-tert.-butoxide, sodium methoxide, sodium ethoxide or basic ion exchanger.

The subsequent intramolecular alkylation is conveniently carried out in a solvent or mixture of solvents such as benzene, chlorobenzene, toluene, xylene, glycoldimethylether, diethyleneglycoldimethylether, dimethylformamide, dimethylsulphoxide, sulpholane, methylene chloride, tetrachloromethane, N-ethyl-diisopropylamine, N-$C_{1-5}$-alkylmorpholine, N-$C_{1-5}$-alkylpiperidine, N-$C_{1-5}$-alkylpyrrolidine, triethylamine, pyridine, for example at temperatures between −30 and 250° C., but preferably between 0 and 150° C., conveniently in the presence of bases such as pyridine, triethylamine, potassium carbonate, sodium carbonate, potassium-tert.-butoxide, sodium methoxide, sodium ethoxide, sodium hydride, potassium hexamethyldisilazane or lithium diisopropylamide.

c) Nucleophilic substitution with a compound of general formula

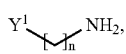 (X)

wherein $Y^1$ denotes a hydroxyl, amino or thiol function optionally blocked by a corresponding protective group and n is a number between 2 and 4, at the aromatic group of general formula

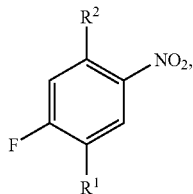 (VI)

wherein $R^1$ and $R^2$ are as defined above, and subsequent cyclisation by reaction with a compound of general formula

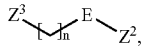 (XI)

wherein $Z^2$ and $Z^3$ denote nucleofugic leaving groups such as chlorine, bromine or iodine atoms or triflate, mesylate or tosylate groups, E denotes the carbonyl or sulphonyl group and n is a number between 0 and 4, while individual methylene groups may be substituted as described above or may be replaced by optionally substituted heteroatoms or other groupings.

The initial nucleophilic aromatic substitution is carried out for example as described under (a) 1) i) a)i). It is optionally followed by the unblocking of the nucleophilic group $Y^1$ by methods known from the literature or as generally described hereinafter.

The reaction of the resulting compound with the compound of general formula (X) is conveniently carried out in a solvent or mixture of solvents such as benzene, chlorobenzene, toluene, xylene, glycoldimethylether, diethyleneglycoldimethylether, dimethylformamide, N-methylpyrrolidinone, tetralin, dimethylsulphoxide, sulpholane, methylene chloride, chloroform, tetrachloromethane, N-ethyl-diisopropylamine, N-$C_{1-5}$-alkylmorpholine, N-$C_{1-5}$-alkylpiperidine, N-$C_{1-5}$-alkylpyrrolidine, triethylamine, pyridine, for example at temperatures between −30 and 250° C., but preferably between 0 and 150° C., conveniently in the presence of bases such as pyridine, triethylamine, p-dimethylaminopyridine, potassium carbonate, sodium carbonate, potassium-tert.-butoxide, sodium methoxide, sodium ethoxide or basic ion exchanger.

d) Alkylation and subsequent acylation/sulphonylation of a compound of general formula

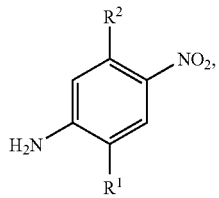 (VIII)

wherein $R^1$ and $R^2$ are as defined above, with a compound of general formula

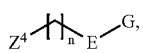 (IX)

wherein E denotes a carbonyl, oxycarbonyl, sulphonyl or a sulphamoyl group optionally substituted at the nitrogen atom of a as mentioned above, G denotes a chlorine, bromine or iodine atom or an anhydride, $C_{1-5}$-alkoxy or benzotriazoloxy group or E and G together denote an isocyano group and $Z^4$ denotes a nucleofugic leaving group, for example a chlorine, bromine or iodine atom, a tosylate, triflate or mesylate group, and n is a number between 2 and 5, while individual methylene groups according to the description given above may additionally be substituted or replaced by heteroatoms, and subsequent intramolecular cyclisation by alkylation of the anilide nitrogen, thereby cleaving the nucleofugic leaving group $Z^4$.

The alkylation is conveniently carried out in a solvent or mixture of solvents such as benzene, chlorobenzene, toluene, xylene, glycoldimethylether, diethyleneglycoldimethylether, dimethylformamide, dimethylsulphoxide, sulpholane, methylene chloride, tetrachloromethane, N-ethyl-diisopropylamine, N-$C_{1-5}$-alkylmorpholine, N-$C_{1-5}$-alkylpiperidine, N-$C_{1-5}$-alkylpyrrolidine, triethylamine, pyridine, for example at temperatures between −30 and 250° C., but preferably between 0 and 150° C., conveniently in the presence of bases such as pyridine, triethylamine, potassium carbonate, sodium carbonate, potassium-tert.-butoxide, sodium methoxide, sodium ethoxide, sodium hydride, lithium, sodium, potassium hexamethyldisilazane or lithium diisopropylamide. The subsequent intramolecular acylation/sulphonylation is conveniently carried out in a solvent or mixture of solvents such as benzene, chlorobenzene, toluene, xylene, glycoldimethylether, diethyleneglycoldimethylether, dimethylformamide, N-methylpyrrolidinone, tetralin, dimethylsulphoxide, sulpholane, methylene chloride, chloroform, tetrachloromethane, N-ethyl-diisopropylamine, N-$C_{1-5}$-alkylmorpholine, N-$C_{1-5}$-alkylpiperidine, N-$C_{1-5}$-alkylpyrrolidine, triethylamine, pyridine, for example at temperatures between −30 and 250° C., but preferably between 0 and 150° C., conveniently in the presence of bases such as pyridine, triethylamine, p-dimethylaminopyridine, potassium carbonate, sodium carbonate, potassium-tert.-butoxide, sodium methoxide, sodium ethoxide or basic ion exchanger.

e) Sequential alkylation of a compound of general formula

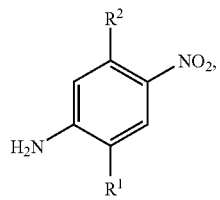
(VIII)

wherein $R^1$ and $R^2$ are as defined above, with a compound of general formula

(XII)

wherein $Z^5$ denotes a nucleofugic leaving group such as for example a bromine or chlorine atom or a tosylate, triflate or mesylate group, $Y^1$ denotes a nucleophilic group, optionally blocked by a suitable protective group, such as a hydroxy group or an amino group optionally substituted as described hereinbefore and m is a number between 2 and 5, while individual methylene groups as described above may additionally be substituted or replaced by heteroatoms, with subsequent acylation/sulphonylation with a compound of general formula

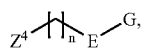
(IX)

wherein E denotes a carbonyl, oxycarbonyl, sulphonyl or a sulphamoyl group optionally substituted at the nitrogen atom of a as mentioned above, G denotes a chlorine, bromine or iodine atom or an anhydride, $C_{1-5}$-alkoxy or benzotriazoloxy group or E and G together denote an isocyanato or cyano group and $Z^4$ denotes a nucleofugic group, for example a bromine or chlorine atom or a tosylate, triflate or mesylate group, and n is a number between 2 and 5, while individual methylene groups according to the description given above may additionally be substituted or replaced by heteroatoms, and subsequent intramolecular cyclisation by alkylation of the optionally previously unblocked nucleophilic group $Y^1$, thereby cleaving the nucleofugic leaving group $Z^4$.

Both the necessary alkylations and the acylation/sulphonylation may be carried out analogously to the conditions described under (a)1)i)b) or (a)1)i) d).

f) Carbamoylation/urea formation with a compound of general formula

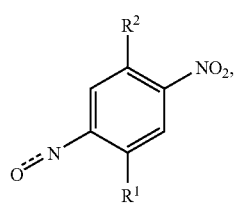
(XIII)

wherein $R^1$ and $R^2$ are as defined above, and which may be obtained by methods known from the literature from compounds of general formula (VIII), for example by reacting with phosgene in toluene, with a compound of general formula

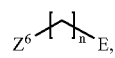
(XIV)

wherein $Z^6$ denotes a nucleofugic leaving group, for example a chlorine, bromine or iodine atom, a tosylate, triflate or mesylate group, and E denotes a hydroxyl, amino or $C_{1-3}$-alkylamino function and n is a number between 2 and 4, while individual methylene groups may additionally be substituted as described above, and subsequent intramolecular cyclisation by alkylation of the anilidic nitrogen, thereby cleaving the nucleofugic leaving group $Z^6$.

The carbamoylation is conveniently carried out in a solvent or mixture of solvents such as benzene, chlorobenzene, toluene, xylene, glycoldimethylether, diethyleneglycoldimethylether, dimethylformamide, N-methylpyrrolidinone, tetralin, dimethylsulphoxide, sulpholane, methylene chloride, chloroform, tetrachloromethane, N-ethyl-diisopropylamine, N-$C_{1-5}$-alkylmorpholine, N-$C_{1-5}$-alkylpiperidine, N-$C_{1-5}$-alkylpyrrolidine, triethylamine, pyridine, for example at temperatures between −30 and 250° C., but preferably between 0 and 150° C. The subsequent intramolecular alkylation is carried out for example analogously to the description in (a)1)i)b).

ii) Transition metal-catalysed coupling reaction of a compound of general formula

A-H (XV), wherein A is as defined above, at the aromatic group of general formula

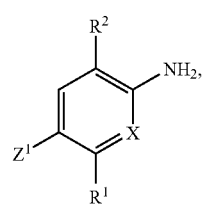
(XVI)

wherein X, $R^1$ and $R^2$ are as defined above and $Z^1$ denotes a chlorine, bromine or iodine atom or a triflate group.

The reaction is expediently carried out in a solvent or mixture of solvents such as benzene, toluene, xylene, tetrahydrofuran, dioxane, diethyl ether, tert.-butyl-methyl-ether, ethyleneglycoldimethylether, diethyleneglycoldimethylether, sulpholane, dimethylformamide, N-methylpyrrolidinone, tetralin, dimethylsulphoxide, methylene chloride, chloroform or tetrachloromethane, for example at temperatures between −30 and 250° C., but preferably between 0 and 200° C., conveniently in the presence of transition metal catalysts such as tetrakis-(triphenylphosphine)-palladium(0), tris-(dibenzylideneacetone)-dipalladium(0), palladium(II)acetate, palladium(II)chloride, bis-(triphenylphosphine)-palladium(II)-chloride, bis-(tricyclohexylphosphine)-palladium (II)-chloride, bis-(triethylphosphine)-palladium(II)-chloride, bis-(tri-o-tolylphosphine)-palladium(II)-chloride, optionally in the presence of ligands such as triphenylphosphine, tri-o-tolylphosphine, tri-tert.-butylphosphine, 1,3-bis-(diphenylphosphino)-propane, 2,2'-bis-(diphenylphosphino)-1,1'-dinaphthyl, 1,1'-bis-(diphenylphosphino)-ferrocene, Xantphos, or for example in the presence of a transition metal catalyst such as copper(I)-iodide, copper(I)-bromide or copper(I)-acetate and conveniently in the presence of a base such as tetramethylguanidine, tetramethylethylenediamine or N,N'-dimethylethylenediamine and conveniently in the presence of a base such as sodium methoxide, sodium ethoxide, sodium-tert.-butoxide, potassium-tert.-butoxide, sodium-tert.-butyldimethyl-silanoate, potassium hexamethyldisilazane, lithium diisopropylamide, potassium carbonate, rubidium carbonate, caesium carbonate, potassium phosphate, sodium hydride, optionally in the presence of a complexing agent such as 18-crown-6-ether as well as conveniently using an inert gas atmosphere (for example nitrogen or argon) and optionally under pressure.

iii) Ring-closing metathesis of a compound of general formula

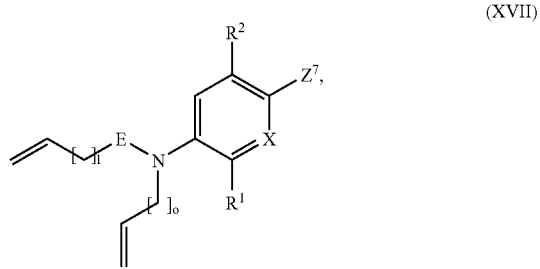

(XVII)

wherein X, R$^1$ and R$^2$ are as defined above, Z$^7$ denotes an optionally substituted amino group or the nitro group, E denotes an aminocarbonyl, aminosulphonyl group or a carbonyl or sulphonyl group optionally substituted as described above, while l and o independently of one another denote identical or different numbers between 1 and 3 which may be obtained by a sequence of alkylation and acylation/sulphonylation/carbamoylation/sulphamoylation with corresponding reagents using the methods already described in (a)1)i)c), for example, or by other methods known from the literature, optionally followed by reduction, if Z$^7$ denotes a nitro group, using the procedure described under (a)1)i)

The ring closing metathesis reaction is conveniently carried out in a solvent or mixture of solvents such as benzene, chlorobenzene, toluene, xylene, methanol, ethanol, propanol, diethyl ether, tert.-butyl-methyl-ether, tetrahydrofuran, dioxane, glycoldimethylether, diethyleneglycoldimethylether, dimethylformamide, N-methylpyrrolidinone, tetralin, dimethylsulphoxide, sulpholane, methylene chloride, chloroform, tetrachloromethane, pyridine, in the presence of a catalyst such as benzylidene-bis-(tricyclohexylphosphine)-dichloro-ruthenium (1st generation Grubbs catalyst) or benzylidene-[1,3-bis(2,4,6-trimethylphenyl)-2-imidazolidinylidene]-dichloro-(tricyclo-hexylphosphine)-ruthenium (2nd generation Grubbs catalyst) for example at temperatures between −30 and 250° C., but preferably between 0 and 150° C., conveniently under an inert gas atmosphere, for example argon.

2) Preparation of a compound of general formula (II), wherein X, R$^1$ and R$^2$ are as defined above and which contain, according to the definition of A, thiocarbonyl or optionally correspondingly substituted imino groups in the ring:

i) thionylation of the corresponding carbonyl-analogous compound of general formula (XV), optionally followed by alkylation of the sulphur and reaction with a correspondingly substituted amine (for example methylamine, hydroxylamine, acetoxyamine, methoxyamine, cyanamide or corresponding analogous compounds), and subsequent coupling of the compound obtained with a compound of general formula (XVI) according to the description of (a)1)ii)

The thionation is conveniently carried out, for example, in a solvent or mixture of solvents such as pentane, hexane, cyclohexane, heptane, benzene, toluene, xylene, glycoldimethylether, diethyleneglycoldimethylether, dioxane, tetrahydrofuran, dichloromethane, chloroform, tetrachloromethane, 1,2-dichloroethane, N-methylpyrrolidinone, or N-ethyl-diisopropylamine, N-C$_{1-5}$-alkylmorpholine, N-C$_{1-5}$-alkylpiperidine, N-C$_{1-5}$-alkylpyrrolidine, triethylamine, pyridine, with reagents such as for example phosphorus pentasulphide, 2,2-bis-(4-methoxy-phenyl)-1,3,2,4-dithiadiphosphetane-2,4-disulphide (Lawesson's reagent) or mixtures of reagents such as for example phosphorus oxychloride followed by 1,1,1,3,3,3-hexamethyldisilathiane, trifluorosulphonic anhydride followed by hydrogen sulphide, or the mixture of hydrogen sulphide, chlorotrimethylsilane and lithium-diisopropylamide, optionally in the presence of a base such as potassium carbonate, sodium carbonate, sodium hydrogen carbonate, pyridine, triethylamine, for example at temperatures between −30 and 250° C., but preferably between −10 and 150° C. Any subsequent alkylation of the corresponding thiocarbonyl compounds is conveniently carried out for example in a solvent or mixture of solvents such as pentane, hexane, cyclohexane, heptane, benzene, toluene, xylene, glycoldimethylether, diethyleneglycoldimethylether, dioxane, tetrahydrofuran, dichloromethane, chloroform, tetrachloromethane, 1,2-dichloroethane, chlorobenzene, pyridine, water, methanol, ethanol, n-propanol, iso-propanol, n-butanol, acetone, butanone, acetonitrile or nitromethane, optionally under 2-phase conditions with the addition of a phase transfer catalyst such as tetrabutyl-ammonium-chloride, tetrabutyl-ammonium-bromide, methyl-trioctyl-ammonium-chloride or Aliquat 336 with reagents such as for example methyl iodide, ethylbromide, dimethylsulphate, diethylsulphate or trimethyloxonium-tetrafluoroborate, conveniently optionally in the presence of a base such as potassium carbonate, sodium carbonate, sodium hydrogen carbonate, pyridine, triethylamine, N-ethyl-diisopropylamine, N-C$_{1-5}$-alkylmorpholine, N-C$_{1-5}$-alkylpiperidine, N-C$_{1-5}$-alkylpyrrolidine, for example at temperatures between −30 and 250° C., but preferably between −10 and 150° C. The reaction with an amino compound to prepare the corresponding imine, following an alkylation, is conveniently carried out for example in a solvent or mixture of solvents such as pentane, hexane, cyclohexane, heptane, benzene, toluene, xylene, glycoldimethylether, diethyleneglycoldimethylether, dioxane, tetrahydrofuran, dichloromethane, chloroform, tetrachloromethane, 1,2-dichloroethane, chlorobenzene, pyridine, water, methanol, ethanol, n-propanol, iso-propanol, n-butanol, acetone, butanone, acetonitrile or nitromethane, with corresponding reagents depending on the substitution of the imine, such as for example ammonia, sodium amide, hydroxylamine, methoxyamine, ethoxyamine, propoxyamine acetoxyamine or cyanamide, optionally in the presence of a base such as sodium hydride, potassium hydride, potassium carbonate, sodium carbonate, sodium hydrogen carbonate, pyridine, triethylamine and optionally under pressure, at temperatures between −30 and 250° C., but preferably between −20 and 120° C., for example.

ii) Thionylation of the corresponding carbonyl-analogous compound of general formula (III), which may be obtained by the methods described under (a)1)ii)a), b), c), d) and e), optionally followed by alkylation of the sulphur and reaction with a correspondingly substituted amine (for example methylamine, hydroxylamine, acetoxyamine, methoxyamine, cyanamide or corresponding analogous compounds), and subsequent reduction of the nitro group by the methods described in (a)1)i), optionally followed by reductive amination according to the methods described under (a)2).

The thionylation and the reaction of alkylation and imine formation which optionally follows may be carried out analogously to the methods described under (a)3)i).

iii) thionylation of the corresponding carbonyl-analogous compound of general formula (II), which may be obtained according to the processes described in (a)1)i), ii), iii) and (a)2), optionally followed by alkylation of the sulphur and reaction with a correspondingly substituted amine (for example methylamine, hydroxylamine, acetoxyamine, methoxyamine, cyanamide or corresponding analogous compounds), while during any subsequent alkylation the aniline amino group present is conveniently blocked by suitable protective groups which are cleaved after the reaction to form the imine.

The thionylation and the reaction of alkylation and imine formation which optionally follows may be carried out analogously to the methods described under (a)3)i).

3) Preparation of a compound of general formula (II), wherein X, $R^1$ and $R^2$ are as defined above and contain the imino groups optionally substituted according to the definition for A in the ring:

i) alkylation of the carbonyl-analogous compounds of general formula (XV) and subsequent reaction with a correspondingly substituted amine (for example methylamine, hydroxylamine, acetoxyamine, methoxyamine, cyanamide or corresponding analogous compounds), and subsequent coupling of the resulting compound with a compound of general formula (XVI) according to description (a)1)ii)

The alkylation and the subsequent reaction with an amino compound in order to prepare the corresponding imine may be carried out as described under (a)3) i).

ii) alkylation of the carbonyl-analogous compounds of general formula (III), which may be obtained according to the processes described in (a)1)i) a), b), c), d) and e), and subsequent reaction with a correspondingly substituted amine (for example methylamine, hydroxylamine, acetoxyamine, methoxyamine, cyanamide or corresponding analogous compounds), and subsequent reduction of the nitro group by the methods described in (a)1)i), optionally with subsequent reductive amination by the methods described in (a)2).

The alkylation and the subsequent reaction with an amino compound in order to prepare the corresponding imine may be carried out as described under (a)3) i).

(b) In order to prepare a compound of general formula

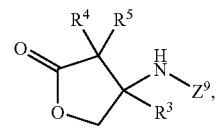

(XVIII)

wherein $Z^9$ denotes a protective group of the amino function which may subsequently be cleaved by methods known from the literature, and $R^3$ to $R^5$ are as defined above:

1) reduction and subsequent lactonisation of a compound of general formula

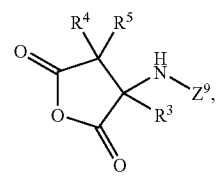

(XIX)

wherein $Z^9$ denotes a protective group for the amino function which may subsequently be cleaved by methods known from the literature, and $R^3$ to $R^5$ are as defined above:

The reduction to the intermediate hydroxy acid is for example conveniently carried out in a solvent or mixture of solvents such as tetrahydrofuran, dioxane, glycoldimethylether, diethyleneglycoldimethylether, pentane, hexane, cyclohexane, heptane, benzene, toluene or xylene with complex hydrides such as sodium borohydride, lithium borohydride, sodium cyanoborohydride, for example, at temperatures between −80 and 250° C., but preferably between −30 and 150° C.

The subsequent lactonisation of the intermediate is conveniently carried out for example in a solvent or mixture of solvents such as benzene, chlorobenzene, toluene, xylene, dichloromethane, chloroform, tetrachloromethane, 1,2-dichloroethane in the presence of a catalyst such as para-toluenesulphonic acid, camphorsulphonic acid or acidic ion exchanger, optionally in the presence of a drying agent such as sodium sulphate, magnesium sulphate or molecular sieves, for example at temperatures between −30 and 250° C., but preferably at temperatures between 0 and 200° C. This reaction may, for example, be carried out as described by G. J. McGarvey, J. M. Williams, R. N. Hiner, Y. Matsubara, T. Oh J. Am. Chem. Soc. 1986, 108, 4943-4952.

2) (Sequential) alkyation of a compound of general formula

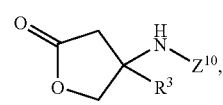

(XX)

wherein $R^3$ is as defined above and $Z^{10}$ denotes a protective group for the amino function which may subsequently be cleaved by methods known from the literature, but also an acyl group of formula

wherein B is as defined above, with a compound of general formula $$T-Z^{11} \quad (XXI),$$

wherein the group T denotes the groups $R^4$ or $R^5$ as defined above, with the proviso that T may not represent the group $OR^9$, and $Z^{11}$ denotes a nucleofugic group, for example an iodine, bromine or chlorine atom or a tosylate, triflate or mesylate group:

The alkyation may be repeated with a similar or different alkylating agent of formula (XXI), so as to obtain □,□-disubstituted lactones of the compound (XVIII).

The alkylations may be carried out analogously to the conditions described under (a)1)i) b) or as described in A. El Hadri, A. Ahbouabdellah, U. Thomet, R. Baur, R. Furtmüller, E. Sigel, W. Sieghart, R. H. Dodd, *J. Med. Chem.* 2002, 45, 2824-2831.

3) Nucleophilic Substitution of a Compound of General Formula

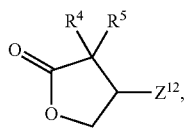

wherein $Z^{12}$ denotes a nucleofugic group, for example an iodine, bromine or chlorine atom or a tosylate, triflate or mesylate group, and $R^4$ and $R^5$ are as defined above, with a compound selected for example from among lithium, sodium, potassium azide, sodium, potassium phthalimide, 4-methoxybenzylamine, benzylamine, 2,4-dimethoxybenzylamine, dibenzylamine, potassium or sodium cyanide, and subsequent reduction of the group thus introduced and treatment of the protective group The nucleophilic substitution is conveniently carried out in a solvent or mixture of solvents such as ethanol, isopropanol, benzene, chlorobenzene, toluene, xylene, glycol, glycoldimethylether, diethyleneglycoldimethylether, dimethylformamide, N-methylpyrrolidinone, tetralin, dimethylsulphoxide, sulpholane, methylene chloride, chloroform, tetrachloromethane or N-ethyl-diisopropylamine, N-$C_{1-5}$-alkylmorpholine, N-$C_{1-5}$-alkylpiperidine, N-$C_{1-5}$-alkylpyrrolidine, triethylamine, pyridine, for example at temperatures between −30 and 250° C., but preferably between 0 and 150° C., optionally conveniently in the presence of bases such as lithium, sodium, potassium, caesium carbonate, potassium-tert.-butoxide, sodium ethoxide, potassium hexamethyldisilazane, sodium hydride or lithium diisopropylamide. For example this reaction may be carried out as described by R. N. Salvatore, A. S. Nagle, K. W. Jung, *J. Org. Chem.* 2002, 67, 674-683.

The subsequent reduction of the nitrogen nucleophil thus introduced is carried out for example analogously to the description under (a)1).

The aminolactone thus obtained is provided with a protective group, for example, by methods known from the literature.

Compounds of formula (XXII) may be prepared, for example, from malonic acids as described by J.-L. Canet, A. Fadel, J. Salaun, *J. Org. Chem.* 1992, 57, 3463-3473.

(c) In order to prepare a compound of general formula

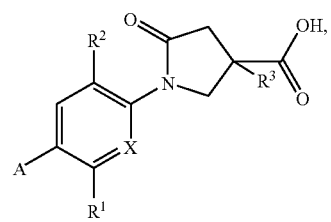

wherein A, X and $R^1$ to $R^3$ are as defined above:

tandem Michael addition/lactamisation of a compound of general formula

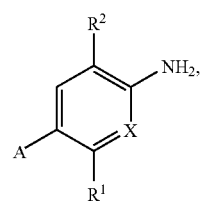

wherein A, X, $R^1$ and $R^2$ are as defined above, with itaconic acid and optionally a subsequent sequence of esterification, □-alkylation with a compound of general formula $$T^1-Z^{11} \quad (XXIV),$$

wherein $T^1$ denotes a $C_{1-3}$-alkyl group and $Z^{11}$ denotes a nucleofugic group, for example an iodine, bromine or chlorine atom or a tosylate, triflate or mesylate group, and unblocking of the carboxylic acid:

The tandem Michael addition/lactamisation is conveniently carried out with itaconic acid at a temperature of 50-250° C., but preferably at 80-200° C., in the presence or absence of a solvent or mixture of solvents such as water, ethanol, propanol, butanol, toluene, xylene, chlorobenzene, tetralin, diphenylether. This reaction makes it possible to synthesise compounds of general formula (XXIII) with the proviso that $R^3$ denotes a hydrogen atom. Optional subsequent substitution is prepared for by blocking the carboxylic acid function by esterification using methods known from the literature.

The alkylation may be carried out analogously to the conditions described under (a)1)i) b) or as described by X.-H. Jiang, Y.-L. Song, Y.-Q. Long, *Bioorg. Med. Chem. Lett.* 2004, 14, 3675-3678.

The unblocking of the esterified carboxylic acid by methods known from the literature makes it possible to prepare □-substituted carboxylic acids of general formula (XXIII), wherein $R^3$ then also denotes a $C_{1-3}$-alkyl group.

(d) In order to prepare a compound of general formula

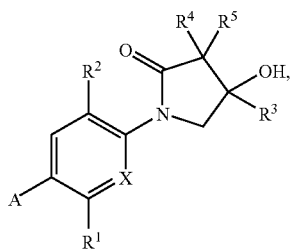 (XXV)

wherein A, X and $R^1$ to $R^5$ are as defined above:
1) Transition metal-catalysed coupling reaction of a compound of general formula

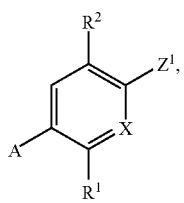 (XXVI)

wherein A, X, $R^1$ and $R^2$ are as defined above and $Z^1$ denotes a chlorine, bromine or iodine atom or a triflate group, with
a compound of general formula

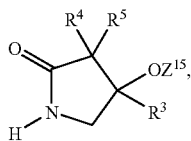 (XXVII)

wherein $R^3$ to $R^5$ are as defined above and $Z^{15}$ denotes a protective group for the hydroxy function, and
subsequent unblocking of the hydroxy function:

The coupling reaction may for example be carried out analogously to the conditions described under (a)1)a)ii).

The unblocking of the hydroxy function may be carried out using methods known from the literature.

The compounds of general formula (XXVI) may be prepared from the corresponding amines of general formula (II) by methods known from the literature such as for example the Sandmeyer reaction.

(e) In order to prepare a compound of general formula

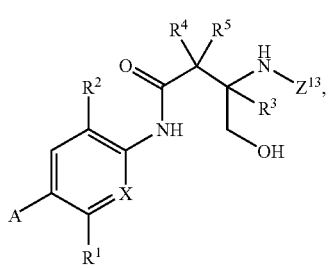 (XXVIII)

wherein A, X and $R^1$ to $R^5$ are as defined above and $Z^{13}$ denotes a protective group for the amino function, which may subsequently be cleaved using methods known from the literature, but may also denote an acyl group of formula

wherein B is as defined above:
Lewis acid-assisted lactone opening of a compound of general formula

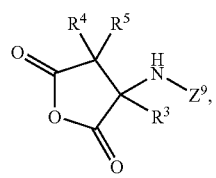 (XXIX)

wherein $R^3$ to $R^5$ are as defined above and $Z^{13}$ denotes a protective group for the amino function, which may subsequently be cleaved using methods known from the literature, but may also denote an acyl group of formula

wherein B is as defined above,
with a compound of general formula

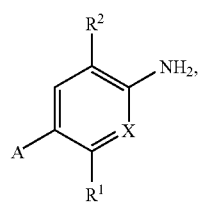 (II)

wherein A, X, $R^1$ and $R^2$ are as defined above:

The compound of general formula (II) is activated with an organoaluminium compound such as for example trimethylaluminium, triethylaluminium, tripropylaluminium, triisobutylaluminium, tributylaluminium, triphenylaluminium in a solvent or mixture of solvents such as dichloromethane, toluene, xylene, benzene, hexane, cyclohexane, heptane, tetrahydrofuran, at a temperature of −100 to 100° C., but preferably between −80 and 80° C., and reacted with the lactone of general formula (XXIX).

(f) In order to prepare a compound of general formula

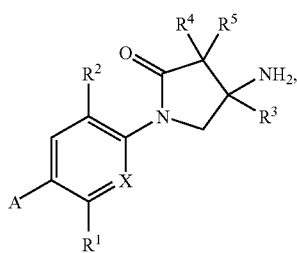

(XXX)

wherein A, X and $R^1$ to $R^5$ are as defined above:
1) Nucleophilic Ring Opening of a Compound of General Formula

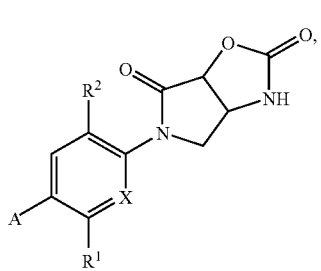

(XXXI)

wherein A, X, $R^1$ and $R^2$ are as defined above,
with an alkali metal salt of the compound $R^9OH$,
wherein $R^9$ is as defined above:

The nucleophilic ring opening of the carbamate to form the free amine is conveniently carried out in a solvent or mixture of solvents such as water, methanol, ethanol, isopropanol, pentane, hexane, cyclohexane, heptane, benzene, toluene, xylene, glycol, glycoldimethylether, diethyleneglycol dimethylether, dioxane, tetrahydrofuran, N-methylpyrrolidinone, dimethylformamide with the lithium, sodium or potassium salt of the compound $R^9OH$, for example at temperatures between −30 and 250° C., but preferably between 0 and 150° C.

The compounds of formula (XXXI) may for example be prepared as described by T. Kametani, Y. Kigawa, M. Ihara, *tetrahedron.* 1979, 35, 313-316.
2) Acid breakdown reaction of a compound of general formula

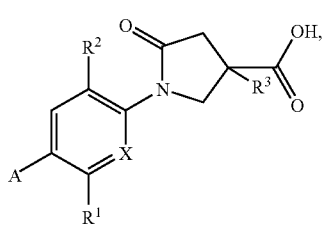

(XXIII)

wherein A, X, $R^1$ to $R^3$ are as defined above:

The carboxylic acids are converted into, for example, activated carbonylamides or carbonylazides by methods known from the literature. By a rearrangement reaction (for example Hofmann, Lossen or Curtius rearrangement) these intermediates are converted into isocyanates.

The isocyanates thus formed are converted by reaction with an alcohol into the carbamates conventionally used as protective groups for the amine function. These carbamate protective groups are subsequently cleaved using methods known from the literature and free the amine of formula (XXX).

The isocyanates may optionally also be converted directly into the amine of formula (XXX) under the effect of aqueous acid are.

The preparation of the activated carboxylic acid derivatives may for example be carried out by activation of the above-mentioned carboxylic acids of formula (XXIII) as carbonylhalides or as asymmetric anhydrides with subsequent reaction with lithium, sodium, potassium azide or hydrazine or hydroxylamine in a solvent or mixture of solvents such as acetone, butanone, water, dimethylformamide, benzene, toluene, xylene, chlorobenzene, acetonitrile, nitromethane, tetrahydrofuran, dioxane, glycoldimethylether, diethyleneglycol dimethylether, dimethylformamide, N-methylpyrrolidinone, dimethylsulphoxide, sulpholane, methylene chloride, chloroform, tetrachloromethane, optionally in the presence of a base such as for example N-ethyl-diisopropylamine, N-$C_{1-5}$-alkylmorpholine, N-$C_{1-5}$-alkylpiperidine, N-$C_{1-5}$-alkylpyrrolidine, triethylamine, pyridine at temperatures between −80 and 250° C., but preferably between −30 and 150° C.

The acid breakdown reaction (i.e. rearrangement to form the isocyanate and carbamate formation) starting from the carboxylic acid of formula (XXIII) is conveniently carried out with diphenylphosphorylazide and a base such as for example N-ethyl-diisopropylamine, N-$C_{1-5}$-alkylmorpholine, N-$C_{1-5}$-alkylpiperidine, N-$C_{1-5}$-alkylpyrrolidine, triethylamine, pyridine, in a solvent or mixture of solvents such as benzene, toluene, chlorobenzene, xylene, tetrahydrofuran, dioxane, glycol dimethylether, diethyleneglycol dimethylether, dimethylformamide, N-methylpyrrolidinone, dimethylsulphoxide, sulpholane, methylene chloride, chloroform or tetrachloromethane at temperatures between −30 and 250° C., but preferably between 0 and 200° C., in the presence of an alcohol such as for example tert.-butanol, benzylalcohol, para-methoxybenzylalcohol, fluorenylmethanol.

These carbamate protective groups are subsequently cleaved using methods known from the literature and free the amine of formula (XXX).
3) Mitsunobu cyclodehydration and subsequent cleaving of the protective groups from a compound of general formula

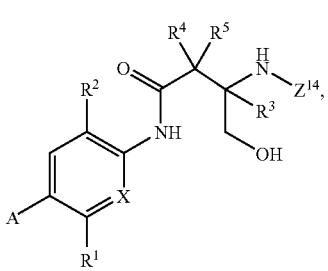

(XXXII)

wherein A, X and $R^1$ to $R^5$ are as defined above and $Z^{14}$ denotes a protective group for the amino function:

The lactamisation under Mitsunubo conditions is conveniently carried out in an inert solvent or mixture of solvents such as for example tetrahydrofuran, dioxane, benzene, toluene, xylene, acetonitrile in the presence of phosphines such as for example triphenylphosphine, tributylphosphine with dialkylazodicarboxylates such as for example diethyl azodicarboxylate, diisopropyl azodicarboxylate, di(tert.-butyl) azodicarboxylate, for example at a temperature of −50 to 200° C., but preferably between −20 and 150° C. The subsequent unblocking of the amino function may be carried out using methods described in the literature.

4) reduction of the aromatic nitro group, subsequent conversion of the amino group thus freed into the group A as defined above and cleaving of the protective group from a compound of general formula

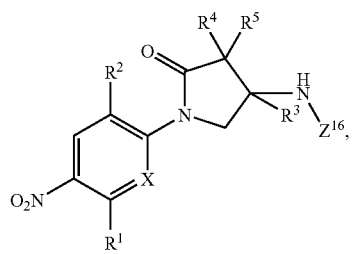

(XXXIII)

wherein X and $R^1$ to $R^5$ are as defined above and $Z^{16}$ denotes a protective group for the amino function:

The reduction of the nitro group may be carried out analogously to the conditions described in (a)1)i).

The subsequent conversion of the amino group thus freed into the group A as defined above may for example be carried out analogously to the conditions described in (a)1)i)b)-f).

The subsequent unblocking of the amino function may be carried out using methods described in the literature.

The compounds of general formula (XXXIII) may be prepared analogously to the conditions described in (e) or (f) 3) from compounds of general formula

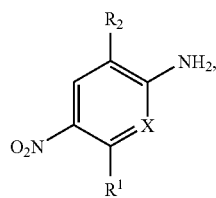

(XXXIV)

wherein X, $R^1$ and $R^2$ are as defined above,
or
from compounds of general formula

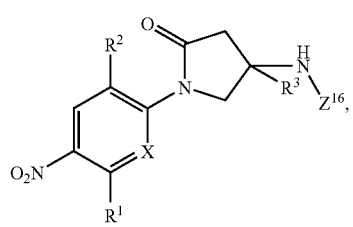

(XXXV)

wherein X and $R^1$ to $R^3$ are as defined above and $Z^{16}$ denotes a protective group for the amino function, by (sequential) alkylation analogously to the conditions described in (a) 1)i)b), by mono-hydroxylation with oxaziridines of the Davis type and optionally subsequent etherification or by aldol reaction with aldehydes of general formula

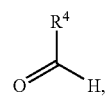

(XXXVI)

wherein $R^4$ is as defined above, while excluding the hydroxy group as the group $R^4$.

The alkyation may be repeated with the same or a different alkylating agent, so as to obtain □,□-disubstituted lactams of the compound (XXXIII). In the alkylation, mono-hydroxylation and the aldol reaction the lactam of general formula (XXXV) may in each case be deprotonated analogously to the conditions described under (a)1)i)b) and reacted with an electrophil such as e.g. an oxaziridine (for example phenylsulphonyloxaziridine or camphorsulphonyloxaziridine) or an aldehyde of general formula (XXXVI).

5) Activation, nucleophilic substitution and reduction of the thus introduced group of a compound of general formula

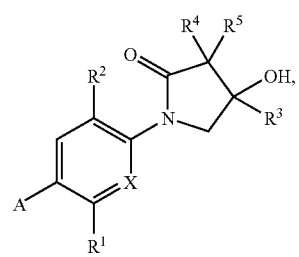

(XXV)

wherein A, X and $R^1$ to $R^5$ are as defined above, and nucleophilic substitution with a compound selected for example from among lithium, sodium, potassium azide, sodium, potassium phthalimide, 4-methoxybenzylamine, benzylamine, 2,4-dimethoxybenzylamine, dibenzylamine, potassium or sodium cyanide, and subsequent reduction of the nitrogen-containing group thus introduced:

The activation of the alcohol function of a compound of formula (XXV) is carried out using methods known from the literature such as for example transformation into a chlorine, bromine or iodine group or conversion into a nucleofugic group such as for example mesylate, triflate or tosylate.

The nucleophilic substitution with a nitrogen nucleophil and the subsequent reduction of the nitrogen nucleophil thus introduced is carried out for example analogously to the method described in (f)3).

6) Reduction of the aliphatic nitro group of a compound of general formula

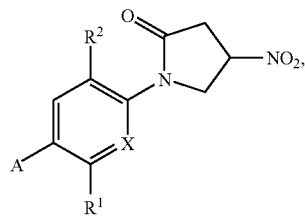
(XXXVII)

wherein A, X, $R^1$ and $R^2$ are as defined above:

The reduction of the nitro group is conveniently carried out in a solvent or mixture of solvents such as for example methanol, ethanol, isopropanol, propanol, butanol, water in the presence of transition metal salts such as for example nickel (II)chloride or cobalt(II)chloride with a reducing agent such as for example lithium borohydride, sodium borohydride, for example at a temperature of −80° C. to 150° C., but preferably between −20 and 100° C.

Compounds of general formula (XXXVII) may be prepared analogously to the conditions described in (c) by a tandem Michael addition/lactamisation from compounds of general formula (II) by reaction with for example methyl 3-nitro-but-3-enoate.

(g) In order to prepare a compound of general formula

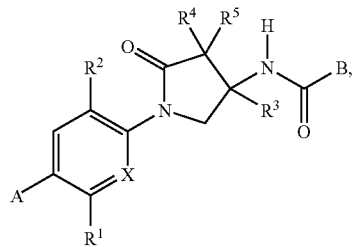
(I)

wherein A, X, B and $R^1$ to $R^5$ are as defined above:

1) Mitsunobu cyclodehydration of a compound of general formula

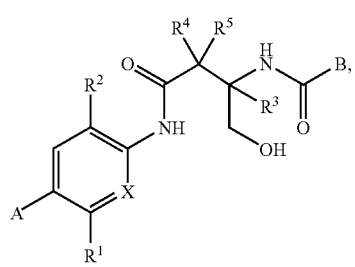
(XXXVIII)

wherein A, X, B and $R^1$ to $R^5$ are as defined above:

The lactamisation under Mitsunobu conditions is carried out for example analogously to the method described in (e)3).

2) Acylation of a compound of general formula

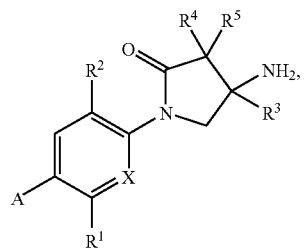
(XXX)

wherein A, X and $R^1$ and $R^5$ are as defined above, with a carboxylic acid or a reactive carboxylic acid derivative of general formula

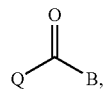
(XXXIX)

wherein B is as defined above and Q denotes a hydroxy or $C_{1-4}$-alkoxy group, a halogen atom or an acyloxy group.

The acylation is conveniently carried out with a corresponding halide or anhydride in a solvent such as methylene chloride, chloroform, carbon tetrachloride, ether, tetrahydrofuran, dioxane, benzene, toluene, acetonitrile, dimethylformamide, sodium hydroxide solution or sulpholane, optionally in the presence of an inorganic or organic base at temperatures between −20 and 200° C., but preferably at temperatures between −10 and 160° C.

The acylation may however also be carried out with the free acid, optionally in the presence of an acid-activating agent or a dehydrating agent, for example in the presence of isobutyl chloroformate, thionyl chloride, trimethylchlorosilane, hydrogen chloride, sulphuric acid, methanesulphonic acid, p-toluenesulphonic acid, phosphorus trichloride, phosphorus pentoxide, N,N'-dicyclohexylcarbodiimide, N,N'-dicyclohexylcarbodiimide/N-hydroxysuccinimide or 1-hydroxybenzotriazole, N,N'-carbonyldiimidazole, N,N'-carbonyldiitriazole, O-(benzotriazol-1-yl)-N,N,N',N'-tetramethyl-uroniumtetrafluoroborate/N-methylmorpholine, O-(benzotriazol-1-yl)-N,N,N',N'-tetramethyl-uroniumtetrafluoroborate/N-ethyldiisopropylamine, O-pentafluorophenyl-N,N,N',N'-tetramethyluronium-hexafluoro-phosphate/triethylamine, N,N'-thionyldiimidazole or triphenylphosphine/carbon tetrachloride, at temperatures between −20 and 200° C., but preferably at temperatures between −10 and 160° C.

Other methods of amide coupling are described for example in P. D. Bailey, I. D. Collier, K. M. Morgan in "Comprehensive Functional Group Interconversions", Vol. 5, page 257ff., Pergamon 1995.

In the reactions described hereinbefore any reactive groups present such as hydroxy, carboxy, amino, alkylamino or imino groups may be protected during the reaction by conventional protective groups which are cleaved again after the reaction.

For example a protecting group for a hydroxy group might be the methoxy, benzyloxy, trimethylsilyl, acetyl, benzoyl, tert.-butyl, trityl, benzyl or tetrahydropyranyl group, protecting groups for a carboxyl group might be the trimethylsilyl, methyl, ethyl, tert.-butyl, benzyl or tetrahydropyranyl group and a protecting group for an amino, alkylamino or imino group might be the acetyl, trifluoroacetyl, benzoyl, ethoxycarbonyl, tert.-butoxycarbonyl, benzyloxycarbonyl, benzyl, methoxybenzyl or 2,4-dimethoxybenzyl group and additionally, for the amino group, the phthalyl group.

Other protective groups and their removal are described in T. W. Greene, P. G. M. Wuts, "Protective Groups in Organic Synthesis", Wiley, 1991 and 1999.

Any protective group used is optionally subsequently cleaved for example by hydrolysis in an aqueous solvent, e.g. in water, isopropanol/water, tetrahydrofuran/water or dioxane/water, in the presence of an acid such as trifluoroacetic acid, hydrochloric acid or sulphuric acid or in the presence of an alkali metal base such as lithium hydroxide, sodium hydroxide or potassium hydroxide or by means of ether splitting, e.g. in the presence of iodotrimethylsilane, at temperatures between 0 and 100° C., preferably at temperatures between 10 and 50° C.

A benzyl, methoxybenzyl or benzyloxycarbonyl group, however, is cleaved by hydrogenolysis, for example, e.g. with hydrogen in the presence of a catalyst such as palladium/charcoal in a solvent such as methanol, ethanol, ethyl acetate, dimethylformamide, dimethylformamide/acetone or glacial acetic acid, optionally with the addition of an acid such as hydrochloric acid at temperatures between 0 and 50° C., but preferably at ambient temperature, and under a hydrogen pressure of 1 to 7 bar, but preferably 1 to 5 bar.

A methoxybenzyl group may also be cleaved in the presence of an oxidising agent such as cerium(IV)ammonium nitrate in a solvent such as methylene chloride, acetonitrile or acetonitrile/water at temperatures between 0 and 50° C., but preferably at ambient temperature.

A methoxy group is conveniently cleaved in the presence of boron tribromide in a solvent such as methylene chloride at temperatures between −35 and −25° C.

A 2,4-dimethoxybenzyl group, however, is preferably cleaved in trifluoroacetic acid in the presence of anisol.

A tert.-butyl or tert.-butyloxycarbonyl group is preferably cleaved by treatment with an acid such as trifluoroacetic acid or hydrochloric acid, optionally using a solvent such as methylene chloride, dioxane or ether.

A phthalyl group is preferably cleaved in the presence of hydrazine or a primary amine such as methylamine, ethylamine or n-butylamine in a solvent such as methanol, ethanol, isopropanol, toluene/water or dioxane at temperatures between 20 and 50° C.

An allyloxycarbonyl group is cleaved by treatment with a catalytic amount of tetrakis-(triphenylphosphine)-palladium (0), preferably in a solvent such as tetrahydrofuran and preferably in the presence of an excess of a base such as morpholine or 1,3-dimedone at temperatures between 0 and 100° C., preferably at ambient temperature and under inert gas, or by treatment with a catalytic amount of tris-(triphenylphosphine)-rhodium(I)chloride in a solvent such as aqueous ethanol and optionally in the presence of a base such as 1,4-diazabicyclo[2.2.2]octane at temperatures between 20 and 70° C.

Moreover, the compounds of general formula I obtained may be resolved into their enantiomers and/or diastereomers.

Thus, for example, the compounds of general formula I obtained which occur as racemates may be separated by methods known per se (cf. Allinger N. L. and Eliel E. L. in "Topics in Stereochemistry", Vol. 6, Wiley Interscience, 1971) into their optical enantiomers and compounds of general formula I with at least 2 asymmetric carbon atoms may be resolved into their diastereomers on the basis of their physical-chemical differences using methods known per se, e.g. by chromatography and/or fractional crystallisation, and, if these compounds are obtained in racemic form, they may subsequently be resolved into the enantiomers as mentioned above.

The enantiomers are preferably separated by column separation on chiral phases or by recrystallisation from an optically active solvent or by reacting with an optically active substance which forms salts or derivatives such as e.g. esters or amides with the racemic compound, particularly acids and the activated derivatives or alcohols thereof, and separating the diastereomeric mixture of salts or derivatives thus obtained, e.g. on the basis of their differences in solubility, whilst the free antipodes may be released from the pure diastereomeric salts or derivatives by the action of suitable agents. Optically active acids in common use are e.g. the D- and L-forms of tartaric acid or dibenzoyltartaric acid, di-o-tolyltartaric acid, malic acid, mandelic acid, camphorsulphonic acid, glutamic acid, aspartic acid or quinic acid. An optically active alcohol may be, for example, (+) or (−)-menthol and an optically active acyl group in amides, for example, may be a (+)- or (−)-menthyloxycarbonyl.

Furthermore, the compounds of formula I may be converted into the salts thereof, particularly for pharmaceutical use into the physiologically acceptable salts with inorganic or organic acids. Acids which may be used for this purpose include for example hydrochloric acid, hydrobromic acid, sulphuric acid, methanesulphonic acid, phosphoric acid, fumaric acid, succinic acid, lactic acid, citric acid, tartaric acid or maleic acid.

Moreover, if the new compounds of formula I contain a carboxy group, they may subsequently, if desired, be converted into the salts thereof with inorganic or organic bases, particularly for pharmaceutical use into the physiologically acceptable salts thereof. Suitable bases for this purpose include for example sodium hydroxide, potassium hydroxide, cyclohexylamine, ethanolamine, diethanolamine and triethanolamine.

As already mentioned hereinbefore, the compounds of general formula I and the tautomers, enantiomers, diastereomers and physiologically acceptable salts thereof have valuable pharmacological properties, particularly an antithrombotic activity which is preferably based on an effect on thrombin or factor Xa, for example on a thrombin-inhibiting or factor Xa-inhibiting activity, on a prolonging effect on the aPTT time and/or on an inhibitory effect on related serine proteases such as e.g. urokinase, factor VIIa, factor IX, factor XI and factor XII.

The compounds listed in the Experimental Section were investigated for their effect on the inhibition of factor Xa as follows:

Method:

Enzyme-kinetic measurement with chromogenic substrate. The quantity of p-nitroaniline (pNA) released from the colourless chromogenic substrate by human factor Xa is determined photometrically at 405 nm. It is proportional to the activity of the enzyme used. The inhibition of the enzyme activity by the test substance (in relation to the solvent control) is determined at various concentrations of test substance and from this the $IC_{50}$ is calculated, as the concentration which inhibits the factor Xa used by 50%.

Material:
Tris(hydroxymethyl)-aminomethane buffer (100 mMol) and sodium chloride (150 mMol), pH 8.0 plus 1mg/ml Human Albumin Fraction V, protease-free
Factor Xa (Calbiochem), spec. activity: 217 IU/mg, final concentration: 7 IU/ml for each reaction mixture
Substrate S 2765 (Chromogenix), final concentration: 0.3 mM/l (1 KM) for each reaction mixture
Test substance: final concentration 100, 30, 10, 3, 1, 0.3, 0.1, 0.03, 0.01, 0.003, 0.001 µMol/l Procedure:
10 µl of a 23.5-times concentrated starting solution of the test substance or solvent (control), 175 µl of TRIS/HSA buffer and 25 µl of a 65.8 U/L Factor Xa working solution are incubated for 10 minutes at 37° C. After the addition of 25 µl of S 2765 working solution (2.82 mMol/l) the sample is measured in a photometer (SpectraMax 250) at 405 nm for 600 seconds at 37° C.

Evaluation:
1. Determining the maximum increase (deltaOD/minutes) over 21 measuring points.
2. Determining the % inhibition based on the solvent control.
3. Plotting a dosage/activity curve (% inhibition vs substance concentration).
4. Determining the $IC_{50}$ by interpolating the X-value (substance concentration) of the dosage/activity curve at Y=50% inhibition.

All the compounds tested had an $IC_{50}$ value of less than 100 µmol/L.

The compounds prepared according to the invention are generally well tolerated.

In view of their pharmacological properties the new compounds and the physiologically acceptable salts thereof are suitable for the prevention and treatment of venous and arterial thrombotic diseases, such as for example the prevention and treatment of deep leg vein thrombosis, for preventing reocclusions after bypass operations or angioplasty (PT(C)A), and occlusion in peripheral arterial diseases, and for preventing and treating pulmonary embolism, disseminated intravascular coagulation and severe sepsis, for preventing and treating DVT in patients with exacerbated COPD, for treating ulcerative colitis, for preventing and treating coronary thrombosis, for preventing stroke and the occlusion of shunts. In addition, the compounds according to the invention are suitable for antithrombotic support in thrombolytic treatment, such as for example with alteplase, reteplase, tenecteplase, staphylokinase or streptokinase, for preventing long-term restenosis after PT(C)A, for the prevention and treatment of ischaemic events in patients with all forms of coronary heart disease, for preventing metastasis and the growth of tumours and inflammatory processes, e.g. in the treatment of pulmonary fibrosis, for preventing and treating rheumatoid arthritis, for preventing and treating fibrin-dependent tissue adhesions and/or the formation of scar tissue and for promoting wound healing processes. The new compounds and the physiologically acceptable salts thereof may be used therapeutically in conjunction with acetylsalicylic acid, with inhibitors of platelet aggregation such as fibrinogen receptor antagonists (e.g. abciximab, eptifibatide, tirofiban, roxifiban), with physiological activators and inhibitors of the clotting system and the recombinant analogues thereof (e.g. Protein C, TFPI, antithrombin), with inhibitors of ADP-induced aggregation (e.g. clopidogrel, ticlopidine), with $P_2T$ receptor antagonists (e.g. cangrelor) or with combined thromboxane receptor antagonists/synthetase inhibitors (e.g. terbogrel).

The dosage required to achieve such an effect is appropriately 0.01 to 3 mg/kg, preferably 0.03 to 1.0 mg/kg by intravenous route, and 0.03 to 30 mg/kg, preferably 0.1 to 10 mg/kg by oral route, in each case administered 1 to 4 times a day.

For this purpose, the compounds of formula I prepared according to the invention may be formulated, optionally together with other active substances, with one or more inert conventional carriers and/or diluents, e.g. with corn starch, lactose, glucose, microcrystalline cellulose, magnesium stearate, polyvinylpyrrolidone, citric acid, tartaric acid, water, water/ethanol, water/glycerol, water/sorbitol, water/polyethylene glycol, propylene glycol, cetylstearyl alcohol, carboxymethylcellulose or fatty substances such as hard fat or suitable mixtures thereof, to produce conventional galenic preparations such as plain or coated tablets, capsules, powders, suspensions or suppositories.

The Examples that follow are intended to illustrate the invention, without restricting its scope:

Experimental Section

As a rule, melting points, IR, UV, $^1$H-NMR and/or mass spectra have been obtained for the compounds prepared. Unless otherwise stated, $R_f$ values were determined using ready-made silica gel 60 $F_{254}$ TLC plates (E. Merck, Darmstadt, Item no. 1.05714) without chamber saturation. The $R_f$ values given under the heading Alox were determined using ready-made aluminium oxide 60 $F_{254}$ TLC plates (E. Merck, Darmstadt, Item no. 1.05713) without chamber saturation. The $R_f$ values given under the heading Reversed-phase-8 (RP-8) were determined using ready-made RP-8 $F_{254s}$ TLC plates (E. Merck, Darmstadt, Item no. 1.15684) without chamber saturation. The ratios given for the eluants refer to units by volume of the solvents in question. For chromatographic purification silica gel made by Messrs Millipore (MATREX™, 35-70 my) was used. Unless more detailed information is provided as to the configuration, it is not clear whether the products are pure stereoisomers or mixtures of enantiomers and diastereomers.

The following abbreviations are used in the descriptions of the experiments:

| | |
|---|---|
| Boc | tert.-butoxycarbonyl |
| DCC | N,N'-dicyclohexylcarbodiimide |
| DIPEA | N-ethyl-diisopropylamine |
| DMSO | dimethylsulphoxide |
| DMF | N,N-dimethylformamide |
| DPPA | diphenylphosphorylazide |
| sat. | saturated |
| i. vac. | in vacuo |
| conc. | concentrated |
| NMM | N-methyl-morpholine |
| NMP | N-methyl-pyrrolidin-2-one |
| o | ortho |
| PfTU | O-pentafluorophenyl-N,N,N',N'-tetramethyluronium-hexafluorophosphate |
| PPA | propanephosphonic acid cycloanhydride |
| quant. | quantitative |
| $R_f$ | retention factor |
| $R_t$ | retention time |
| rac. | racemic |
| TBTU | O-(benzotriazol-1-yl)-N,N,N',N'-tetramethyluronium tetrafluoroborate |
| TEA | triethylamine |
| TFA | trifluoroacetic acid |
| THF | tetrahydrofuran |
| tert. | tertiary |
| Σ | yield over all the steps described, carried out analogously |

The HPLC data were obtained under the following conditions:

Waters ZMD, Alliance 2695 HPLC, Waters 2700 Autosampler, Waters 996
Diode array detector
The mobile phase used was:
A: water with 0.13% TFA
B: acetonitrile with 0.10% TFA

| time in min | % A | % B | flow rate in ml/min |
|---|---|---|---|
| 0.0 | 95 | 5 | 1.00 |
| 0.7 | 95 | 5 | 1.00 |
| 5.2 | 2 | 98 | 1.00 |
| 5.7 | 2 | 98 | 1.00 |
| 6.0 | 95 | 5 | 1.00 |
| 6.5 | 95 | 5 | 1.00 |

The stationary phase used was a Varian column, Microsorb 100 $C_{18}$ 3 µm, 4.6 mm×50 mm, batch no. 2231108 (column temperature: constant at 25° C.).

The diode array detection was carried out at a wavelength range of 210-300 nm.

EXAMPLE 1

5-bromo-thiophene-2-carboxylic acid-{1-[3-chloro-4-(2-oxo-[1,3]oxazinan-3-yl)-phenyl]-5-oxo-pyrrolidin-3-yl}-amide

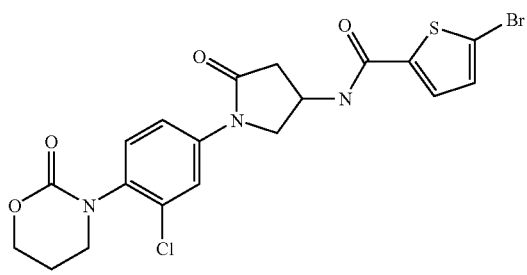

(a) 3-chloropropyl (2-chloro-4-nitro-phenyl)-carbamate 2.0 g (11.59 mmol) 2-chloro-4-nitro-aniline are suspended in 10 ml of toluene and refluxed for two hours with the addition of 1.41 ml (11.59 mmol) diphosgene. Then the mixture is evaporated to dryness in vacuo. The crude product thus obtained is suspended in 50 ml of toluene and combined with 0.97 ml (11.59 mmol) 3-chloro-propan-1-ol. The mixture is stirred for three hours at 60° C. and the mixture is then evaporated to dryness. The residue is purified by chromatography on silica gel (petroleum ether/ethyl acetate 98:2).

Yield: 38% $R_f$ value: 0.22 (silica gel, petroleum ether/ethyl acetate 9:1) $C_{10}H_{10}Cl_2N_2O_4$ (293.10) Mass spectrum: $(M+H)^+$=291/293/295 (chlorine isotopes)

(b) 3-(2-chloro-4-nitro-phenyl)-[1,3]oxazinan-2-one 1.2 g (4.1 mmol) 3-chloropropyl (2-chloro-4-nitro-phenyl)-carbamate are dissolved in 36 ml acetonitrile, combined with 960 mg (6.9 mmol) potassium carbonate and refluxed for 1.5 hours. The reaction mixture is cooled to ambient temperature, filtered to remove undissolved matter and the filtrate is evaporated to dryness.

Yield: quantitative $R_f$ value: 0.17 (silica gel, petroleum ether/ethyl acetate 1:1) $C_{10}H_9ClN_2O_4$ (256.64) Mass spectrum: $(M+H)^+$=257/259 (chlorine isotopes)

(c) 3-(4-amino-2-chloro-phenyl)-[1,3]oxazinan-2-one 200 mg (0.78 mmol) of 3-(2-chloro-4-nitro-phenyl)-[1,3]oxazinan-2-one are dissolved in 10 ml of tetrahydrofuran and combined with 135 mg Raney nickel. The mixture is hydrogenated in a Parr apparatus at ambient temperature at 1 atm hydrogen pressure for three hours. Then the Raney nickel is filtered off and the filtrate is evaporated down i. vac. Yield: 150 mg (85%)

$R_f$ value: 0.16 (silica gel; petroleum ether/ethyl acetate 1:1) $C_{10}H_{11}ClN_2O_2$ (226.66) Mass spectrum: $(M+H)^+$=227/229 (chlorine isotopes)

(d) 1-[3-chloro-4-(2-oxo-[1,3]oxazinan-3-yl)-phenyl]-5-oxo-pyrrolidine-3-carboxylic acid 670 mg (2.96 mmol) 3-(4-amino-2-chloro-phenyl)-[1,3]oxazinan-2-one and 385 mg (2.96 mmol) itaconic acid are melted together under an argon atmosphere at 150° C. for one hour. The mixture is allowed to cool and the crude product is purified by trituration in dichloromethane.

Yield: 356 mg (36%) $R_f$ value: 0.27 (silica gel; dichloromethane/methanol 9:1) $C_{10}H_{11}ClN_2O_2$ (338.74) Mass spectrum: $(M+H)^+$=339/341 (chlorine isotopes)

(e) tert. butyl {1-[3-chloro-4-(2-oxo-[1 3]oxazinan-2-on-3-yl)-phenyl]-5-oxo-pyrrolidin-3-yl}-carbamate 260 mg (0.77 mmol) 1-[3-chloro-4-(2-oxo-[1,3]oxazinan-3-yl)-phenyl]-5-oxo-pyrrolidine-3-carboxylic acid are suspended in 5 ml tert.-butanol and combined with 106 µl (0.77 mmol) triethylamine at ambient temperature. After 15 min stirring 170 µl (0.77 mmol) DPPA are added and the mixture is refluxed for 5 hours. It is left to cool and the volatile constituents are eliminated using the rotary evaporator. The solid residue is purified by chromatography on silica gel (eluant-gradient: dichloromethane/isopropanol 97:3 to 95:5).

Yield: 154 mg (49%) $R_t$ value: 2.63 min $C_{19}H_{24}ClN_3O_5$ (409.86) Mass spectrum: $(M+H)^+$=410/412 (chlorine isotopes)

(f) 3-[4-(4-amino-2-oxo-pyrrolidin-1-yl)-2-chloro-phenyl]-[1,3]oxazinan-2-one-trifluoroacetate 40 mg (98pmol) tert. butyl {1-[3-chloro-4-(2-oxo-[1,3]oxazinan-2-on-3-yl)-phenyl]-5-oxo-pyrrolidin-3-yl}-carbamate are dissolved in 3 ml dichloromethane, combined with 70 µl trifluoroacetic acid and stirred for 16 hours at ambient temperature. The mixture is evaporated to dryness and combined again with dichloromethane and trifluoroacetic acid. After one hour it is evaporated to dryness.

Yield: quantitative $R_t$ value: 2.63 min $C_{14}H_{16}ClN_3O_3$ (309.75) Mass spectrum: $(M+H)^+$=310/312 (chlorine isotopes)

(g) 5-bromo-thiophene-2-carboxylic acid-{1-[3-chloro-4-(2-oxo-[1,3]oxazinan-3-yl)-phenyl]-5-oxo-pyrrolidin-3-yl}-amide 21 mg (100 µmol) 5-bromo-thiophene-2-carboxylic acid are combined in 3 ml DMF with 66 µl (100 µmol) NMM and 32 mg (74 µmol) TBTU and then stirred for 10 min under a nitrogen atmosphere at ambient temperature. Then 42 mg (99 µmol) 3-[4-(4-amino-2-oxo-pyrrolidin-1-yl)-2-chloro-phenyl]-[1,3]oxazinan-2-one-trifluoroacetate dissolved in 1 ml DMF are added and the mixture is stirred for two hours at ambient temperature. Then the reaction mixture is combined with sat. sodium hydrogen carbonate solution and water and extracted with ethyl acetate. The aqueous phase is extracted twice with ethyl acetate. The combined organic phases are dried over sodium sulphate and totally evaporated down i. vac. The residue is chromatographed on silica gel (eluant: dichloromethane/ethanol 95:5).

Yield: 24 mg (49%) $R_f$ value: 0.09 (silica gel; dichloromethane/ethanol 95:5) $C_{19}H_{17}BrClN_3O_4S$ (498.78) Mass spectrum: $(M+H)^+=498/500/502$ (bromine/chlorine isotopes)

The following compounds were prepared analogously:

| No. | Structural formula Name | Yield | Mass peak(s) | $R_f$ value or $R_t$ |
|---|---|---|---|---|
| 3 | 5-chloro-thiophene-2-carboxylic acid-N-{1-[3-methyl-4-(3-oxo-morpholin-4-yl)-phenyl]-5-oxo-pyrrolidin-3-yl}-amide | Σ: 17.3% | $(M - H)^-$ = 432/434 (chlorine isotopes) | 0.17 (silica gel, dichloromethane /isopropanol = 95:5) |
| 4 | 5-bromo-thiophene-2-carboxylic acid-N-{1-[3-methyl-4-(3-oxo-morpholin-4-yl)-phenyl]-5-oxo-pyrrolidin-3-yl}-amide | Σ: 21.0% | $(M + H)^+$ = 478/480 (bromine isotope) | 0.17 (silica gel, dichloromethane /isopropanol = 95:5) |
| 5 | 5-chloro-pyridine-2-carboxylic acid-{1-[3-methyl-4-(3-oxo-morpholin-4-yl)-phenyl]-5-oxo-pyrrolidin-3-yl}-amide | Σ: 14.5% | $(M + H)^+$ = 429/431 (chlorine isotopes) | 0.20 (silica gel, dichloromethane /isopropanol = 95:5) |
| 6 | 5-methyl-thiophene-2-carboxylic acid-{1-[3-methyl-4-(3-oxo-morpholin-4-yl)-phenyl]-5-oxo-pyrrolidin-3-yl}-amide | Σ: 15.7% | $(M - H)^-$ = 412 | 0.20 (silica gel, dichloromethane /isopropanol = 95:5) |

-continued

| No. | Structural formula | Yield | Mass peak(s) | R_f value or R_t |
|---|---|---|---|---|
| 7 | 5-bromo-thiazole-2-carboxylic acid-{1-[3-methyl-4-(3-oxo-morpholin-4-yl)-phenyl]-5-oxo-pyrrolidin-3-yl}-amide | Σ: 14.3% | (M + H)⁺ = 479/481 (bromine isotope) | 0.20 (silica gel, dichloromethane /isopropanol = 95:5) |
| 8 | 5-chloro-thiophene-2-carboxylic acid-{1-[3-chloro-4-(2-oxo-[1,3]oxazinan-3-yl)-phenyl]-5-oxo-pyrrolidin-3-yl}-amide | Σ: 2.5% | (M + H)⁺ = 454/456/458 (chlorine isotopes) | 0.09 (silica gel, dichloromethane /ethanol = 95:5) |
| 17 | 2-bromo-thiazole-5-carboxylic acid-{1-[3-chloro-4-(2-oxo-[1,3]-oxazinan-3-yl)-phenyl]-5-oxo-pyrrolidin-3-yl}-amide | Σ: 1.0% | (M + H)⁺ = 499/501/503 (bromine, chlorine isotopes) | 4.05 min |
| 20 | 5-bromo-thiophene-2-carboxylic acid-{1-[3-methyl-4-(5-oxo-[1,4]oxazepan-4-yl)-phenyl]-5-oxo-pyrrolidin-3-yl}-amide | Σ: 0.2% | (M + H)⁺ = 492/494 (bromine isotope) | 4.19 min |

| No. | Structural formula | Yield | Mass peak(s) | R_f value or R_t |
|---|---|---|---|---|
| 22 | 5-ethynyl-thiophene-2-carboxylic acid-{1-[3-methyl-4-(5-oxo-[1,4]oxazepan-4-yl)-phenyl]-5-oxo-pyrrolidin-3-yl}-amide | Σ: 0.2% | (M + H)+ = 438 | 2.54 min |
| 44 | 5-bromo-thiophene-2-carboxylic acid-{1-[3-chloro-4-(4-methyl-[1,4]diazepam-1-yl)-phenyl]-5-oxo-pyrrolidin-3-yl}-amide | Σ: 0.7% | (M + H)+ = 511/513/515 (bromine, chlorine isotopes) | 2.51 min |
| 45 | 5-chloro-thiophene-2-carboxylic acid-[1-(4-azepan-1-yl-3-chloro-phenyl]-5-oxo-pyrrolidin-3-yl}-amide | Σ: 1.9% | (M − H)− = 450/452/454 (chlorine isotopes) | 0.63 (silica gel, dichloromethane /methanol/ conc. ammonia 90:10:1) |
| 46 | 5-ethynyl-thiophene-2-carboxylic acid-{1-[3-methyl-4-(5-oxo-[1,4]oxazepan-4-yl)-phenyl]-5-oxo-pyrrolidin-3-yl}-amide | Σ: 4.7% | (M − H)− = 440/442 (chlorine isotopes) | 0.55 (silica gel, dichloromethane /methanol/ conc. ammonia 90:10:1) |

| No. | Structural formula | Yield | Mass peak(s) | $R_f$ value or $R_t$ |
|---|---|---|---|---|
| 47 | 5-ethynyl-thiophene-2-carboxylic acid-{1-[3-chloro-4-(2-oxo-azepan-1-yl)-phenyl]-5-oxo-pyrrolidin-3-yl}-amide | Σ: 3.6% | $(M + H)^+$ = 456/458 (chlorine isotopes) | 0.44 (silica gel, dichloromethane /methanol/ conc. ammonia 90:10:1) |
| 48 | 5-chloro-thiophene-2-carboxylic acid-{1-[3-chloro-4-(2-oxo-azepan-1-yl)-phenyl]-5-oxo-pyrrolidin-3-yl}-amide | Σ: 2.3% | $(M - H)^-$ = 464/466 (chlorine isotopes) | 0.45 (silica gel, dichloromethane /methanol/ conc. ammonia 90:10:1) |
| 68 | tert. butyl 4-(2-chloro-4-{4-[5-chloro-thiophene-2-carbonyl)-amino]-2-oxo-pyrrolidin-1-yl}-phenyl)-piperazine-1-carboxylate | Σ: 6.6% | $(M - H)^-$ = 537/539/541 (chlorine isotopes) | 0.32 (silica gel, dichloromethane /mehtanol 20:1) |
| 69 | tert. butyl 4-(2-chloro-4-{4-[5-bromo-thiophene-2-carbonyl)-amino]-2-oxo-pyrrolidin-1-yl}-phenyl)-piperazine-1-carboxylate | Σ: 17% | $(M + H)^+$ = 583/585/587 (bromine, chlorine isotopes) | 0.45 (silica gel, dichloromethane /methanol 15:1) |

-continued

| No. | Structural formula | Yield | Mass peak(s) | R_f value or R_t |
|---|---|---|---|---|
| 70 | 5-chloro-thiophene-2-carboxylic acid-[1-(3-chloro-4-piperazin-1-yl-phenyl)-5-oxo-pyrrolidin-3-yl]-amide (as the hydrochloride salt) | Σ: 5.7% | $(M+H)^+$ = 439/441/443 (chlorine isotopes) | 0.76 (silica gel, dichloromethane /methanol/conc. ammonia (.2:0.1) |
| 71 | 5-bromo-thiophene-2-carboxylic acid-[1-(3-chloro-4-piperazin-1-yl-phenyl)-5-oxo-pyrrolidin-3-yl]-amide (as the hydrochloride salt) | Σ: 7.0% | $(M+H)^+$ = 483/485/487 (bromine, chlorine isotopes) | 0.76 (silica gel, dichloromethane /methanol/conc. ammonia (.2:0.1) |
| 72 | 5-chloro-thiophene-2-carboxylic acid-(1-{3-chloro-4-[2-(2-diethylamino-ethyl)-piperidin-1-yl]-phenyl}-5-oxo-pyrrolidin-3-yl)-amide (as the trifluoroacetate salt) | Σ: 0.7% | $(M+H)^+$ = 537/539/541 (chlorine isotopes) | 0.35 (silica gel, dichloromethane /methanol/ conc. ammonia 90:10:1) |
| 73 | 5-bromo-thiophene-2-carboxylic acid-[1-(4-azepan-1-yl-3-chloro-phenyl)-5-oxo-pyrrolidin-3-yl]-amide | Σ: 6.7% | $(M-H)^-$ = 494/496/498 (bromine, chlorine isotopes) | 0.32 (silica gel, dichloromethane /methanol 15:1) |

-continued

| No. | Structural formula | Yield | Mass peak(s) | R$_f$ value or R$_t$ |
|---|---|---|---|---|
| 74 | 5-chloro-thiophene-2-carboxylic acid-[1-(3-chloro-4-[1,4]oxazepan-4-yl-phenyl)-5-oxo-pyrrolidin-3-yl]-amide | Σ: 2.4% | (M − H)$^-$ = 452/454/456 (chlorine isotopes) | 0.32 (silica gel, dichloromethane /methanol 15:1) |
| 75 | 5-bromo-thiophene-2-carboxylic acid-[1-(3-chloro-4-[1,4]oxazepan-4-yl-phenyl)-5-oxo-pyrrolidin-3-yl]-amide | Σ: 2.2% | (M − H)$^-$ = 496/498/500 (bromine, chlorine isotopes) | 0.22 (silica gel, dichloromethane /methanol 15:1) |
| 76 | 5-chloro-thiophene-2-carboxylic acid-[1-(3-chloro-4-[1,4]diazepan-1-yl-phenyl)-5-oxo-pyrrolidin-3-yl]-amide (as the hydrochloride salt) | Σ: 0.6% | (M + H)$^+$ = 453/455 (chlorine isotopes) | 0.17 (silica gel, dichloromethane /methanol/ conc. ammonia 90:10:1) |
| 77 | 1-(2-chloro-4-{4-[5-chloro-thiophene-2-carbonyl)-amino]-2-oxo-pyrrolidin-1-yl}-phenyl)-piperidin-3-carboxylic acid diethylamide | Σ: 4.3% | (M + H)$^+$ = 537/539/541 (chlorine isotopes) | 0.57 (silica gel, dichloromethane /methanol 15:1) |

| No. | Structural formula | Yield | Mass peak(s) | $R_f$ value or $R_t$ |
|---|---|---|---|---|
| 78 | ![structure 78]<br>5-bromo-thiophene-2-carboxylic acid-[1-(3-chloro-4-[1,4]oxazepan-4-yl-phenyl)-5-oxo-pyrrolidin-3-yl]-amide | Σ: 3.3% | $(M + H)^+$= 581/583/585 (bromine, chlorine isotopes) | 0.56 (silica gel, dichloromethane /methanol 9:1) |
| 79 | ![structure 79]<br>5-bromo-thiophene-2-carboxylic acid-[1-(3-chloro-4-[1,4]diazepan-1-yl-phenyl)-5-oxo-pyrrolidin-3-yl]-amide (as the trifluoroacetate salt) | Σ: 0.4% | $(M + H)^+$= 497/499/501 (bromine, chlorine isotopes) | 0.17 (silica gel, dichloromethane /methanol/ conc. ammonia 90:10:1) |

EXAMPLE 2

(R)-5-bromo-thiophene-2-carboxylic acid-{1-[2-fluoro-4-(3-oxo-morpholin-4-yl)-phenyl]-5-oxo-pyrrolidin-3-yl}-amide

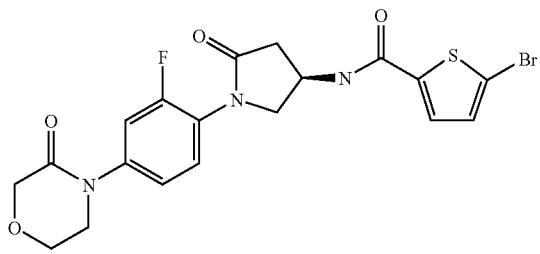

(a) 4-(4-amino-3-fluoro-phenyl)-morpholin-3-one 2.0 g (8.4 mmol) 2-fluoro-4-iodo-aniline, 860 mg (8.5 mmol) morpholin-3-one, 162 mg (0.86 mmol) copper(I)iodide, 2.33 g (16.86 mmol) potassium carbonate and 91 µl N,N'-dimethylethylenediamine are suspended in 18 ml of toluene under an argon atmosphere and stirred for two hours in a microwave at a power of 35 Watts at 140° C. Water is added and the mixture is extracted three times with ethyl acetate. The combined organic phases are dried over sodium sulphate and evaporated to dryness. The residue is purified by chromatography on silica gel (eluant: dichloromethane/methanol 50:1).

Yield: 590 mg (33%) $R_f$ value: 0.60 (silica gel; dichloromethane/methanol 9:1) $C_{10}H_{11}FN_2O_2$ (210.21) Mass spectrum: $(M+H)^+$=211

(b) benzyl (2-hydroxy-(1R)-1-{[2-fluoro-4-(3-oxo-morpholin-4-yl)-phenylcarbamoyl]-methyl}-ethyl)-carbamate 490 mg (2.3 mmol) 4-(4-amino-2-fluoro-phenyl)-morpholin-3-one are dissolved in 3 ml dichloromethane and at ambient temperature slowly combined with 1.18 ml of a solution of trimethylaluminium in toluene (2M, 2.35 mmol). The mixture is stirred for 15 min and then 554 mg (2.3 mmol) benzyl (R)-(5-oxo-tetrahydrofuran-3-yl)-carbamate are added and stirring is continued for 16 hours at ambient temperature. Subsequently the mixture is acidified with 2.5 ml of 2N hydrochloric acid, diluted with water and extracted three times with ethyl acetate. The combined organic phases are dried over sodium sulphate and evaporated to dryness. The crude product thus obtained is purified by chromatography on silica gel (eluant: dichloromethane/methanol 20:1).

Yield: 310 mg (30%) $R_f$ value: 0.60 (silica gel; dichloromethane/methanol 9:1) $C_{22}H_{24}FN_3O_6$ (445.44) Mass spectrum: $(M+H)^+$=446

(c) benzyl (R)-{1-[2-fluoro-4-(3-oxo-morpholin-4-yl)-phenyl]-5-oxo-pyrrolidin-3-yl}-carbamate 310 mg (0.7 mmol) benzyl (2-hydroxy-(1R)-1-{[2-fluoro-4-(3-oxo-morpholin-4-yl)-phenylcarbamoyl]-methyl}-ethyl)-carbamate are dissolved in 3.5 ml THF. While cooling with ice a mixture of 205 mg (0.89 mmol) di-tert.-butyl azodicarboxylate and 210 µl (0.83 mmol) tributylphosphine in 6 ml THF is added. The mixture is slowly heated to ambient temperature and stirred for 16 hours. The mixture is then evaporated to dryness. The residue is purified by reversed-phase chromatography.

Yield: 210 mg (71%) R$_f$ value: 2.59 min C$_{23}$H$_{25}$N$_3$O$_5$ (427.23) Mass spectrum: (M+H)$^+$=428

(d) (R)-4-[4-(4-amino-2-oxo-pyrrolidin-1-yl)-3-fluoro-phenyl]-morpholin-3-one 260 mg (0.6 mmol) benzyl (R)-{1-[2-fluoro-4-(3-oxo-morpholin-4-yl)-phenyl]-5-oxo-pyrrolidin-3-yl}-carbamate are dissolved in 10 ml of methanol, combined with 180 mg palladium on charcoal and hydrogenated for 3.75 hours in a Parr apparatus at 3 bar hydrogen pressure at ambient temperature.

The mixture is filtered to remove the catalyst and evaporated to dryness using the rotary evaporator.

Yield: 124 mg (70%) R$_f$ value: 0.15 (silica gel; dichloromethane/methanol 95:5) C$_{15}$H$_{19}$N$_3$O$_3$ (293.29) Mass spectrum: (M+H)$^+$=294

(e) (R)-5-bromo-thiophene-2-carboxylic acid-{1-[2-fluoro-4-(3-oxo-morpholin-4-yl)-phenyl]-5-oxo-pyrrolidin-3-yl}-amide Prepared analogously to Example 1g from 5-bromo-thiophene-2-carboxylic acid and (R)-4-[4-(4-amino-2-oxo-pyrrolidin-1-yl)-3-fluoro-phenyl]-morpholin-3-one with TBTU and NMM in DMF and subsequent purification by reversed-phase chromatography.

Yield: 42% R$_f$ value: 0.54 (silica gel; dichloromethane/methanol 95:5) C$_{19}$H$_{17}$BrFN$_3$O$_4$S (482.33) Mass spectrum: (M+H)$^+$=482/484 (bromine isotope)

The following compounds were prepared analogously:

| No. | Structural formula | Yield | Mass peak(s) | R$_f$ value or R$_t$ |
|---|---|---|---|---|
|   | Name |   |   |   |
| 9 | | Σ: 8.1% | (M+H)$^+$ 478/480 (bromine isotope) | 2.70 min |
|   | (R)-5-bromo-thiophene-2-carboxylic acid-{1-[3-methyl-4-(3-oxo-morpholin-4-yl)-phenyl]-5-oxo-pyrrolidin-3-yl}-amide | | | |
| 10 | | Σ: 0.4% | (M−H)$^−$ 463/465 (bromine isotope) | 0.06 (silica gel, dichloromethane/ethanol 95:5) |
|   | (R)-5-bromo-thiophene-2-carboxylic acid-{5-oxo-1-[5-(3-oxo-morpholin-4-yl)-pyridin-2-yl]-pyrrolidin-3-yl}-amide | | | |
| 11 | | Σ: 12.2% | (M+H)$^+$ 478/480 (bromine isotope) | 2.63 min |
|   | (S)-5-bromo-thiophene-2-carboxylic acid-{1-[3-methyl-4-(3-oxo-morpholin-4-yl)-phenyl]-5-oxo-pyrrolidin-3-yl}-amide | | | |

| No. | Structural formula | Yield | Mass peak(s) | $R_f$-value or $R_t$ |
|---|---|---|---|---|
| 12 | (R)-5-chloro-thiophene-2-carboxylic acid-{1-[2-fluoro-4-(3-oxo-morpholin-4-yl)-phenyl]-5-oxo-pyrrolidin-3-yl}-amide | Σ: 2.0% | $(M+H)^+ =$ 438/440 (bromine isotope) | 0.51 (silica gel, dichloromethane/methanol = 95:5) |
| 19 | (R)-5-bromo-thiophene-2-carboxylic acid-{1-[2,5-difluoro-4-(3-oxo-morpholin-4-yl)-phenyl]-5-oxo-pyrrolidin-3-yl}-amide | Σ: 5.2% | $(M+H)^+ =$ 500/502 (bromine isotope) | 2.73 min |
| 21 | (R)-5-ethynyl-thiophene-2-carboxylic acid-{1-[3-methyl-4-(3-oxo-morpholin-4-yl)-phenyl]-5-oxo-pyrrolidin-3-yl}-amide | Σ: 1.7% | $(M+H)^+ =$ 424 | 2.58 min |
| 33 | 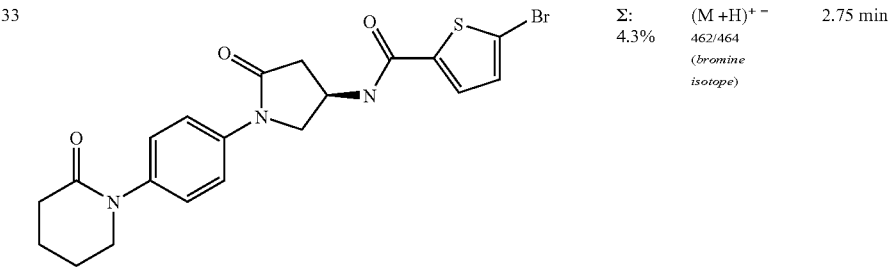 (R)-5-bromo-thiophene-2-carboxylic acid-{5-oxo-1-[4-(2-oxo-piperidin-1-yl)-phenyl]-pyrrolidin-3-yl}-amide | Σ: 4.3% | $(M+H)^+ =$ 462/464 (bromine isotope) | 2.75 min |

| No. | Structural formula | Yield | Mass peak(s) | $R_f$ value or $R_t$ |
|---|---|---|---|---|
| 34 | 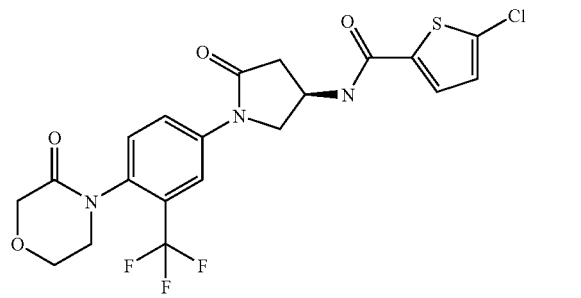 (R)-5-ethynyl-thiophene-2-carboxylic acid-{5-oxo-1-[4-(2-oxo-piperidin-1-yl)-phenyl]-pyrrolidin-3-yl}-amide | Σ: 5.9% | $(M-H)^-$ 406 | 2.63 min |
| 35 | (R)-5-ethynyl-thiophene-2-carboxylic acid-{5-oxo-1-[4-(3-oxo-morpholin-4-yl)-3-trifluoromethyl-phenyl]-pyrrolidin-3-yl}-amide | Σ: 2.8% | $(M-H)^-$ 476 | 2.78 min |
| 36 | (R)-5-bromo-thiophene-2-carboxylic acid-{5-oxo-1-[4-(3-oxo-morpholin-4-yl)-3-trifluoromethyl-phenyl]-pyrrolidin-3-yL}-amide | Σ: 6.1% | $(M+H)^+$ 532/354 (*bromine isotope*) | 2.88 min |
| 37 | (R)-5-chloro-thiophene-2-carboxylic acid-{5-oxo-1-[4-(3-oxo-morpholin-4-yl)-3-trifluoromethyl-phenyl]-pyrrolidin-3-yl}-amide | Σ: 5.5% | $(M-H)^-$ 486/488 (*chlorine isotopes*) | 2.85 min |

-continued

| No. | Structural formula | Yield | Mass peak(s) | R_f value or R_t |
|---|---|---|---|---|
| 41 | (R)-5-bromo-thiophene-2-carboxylic acid-{1-[3-chloro-4-(2-oxo-tetrahydro-pyrimidin-1-yl)-phenyl]-5-oxo-pyrrolidin-3-yl}-amide | Σ: 0.03% | $(M+H)^+$ = 497/499/501 (bromine/chlorine isotopes) | 2.71 min |
| 50 | (R)-5-bromo-thiophene-2-carboxylic acid-{1-[3-methyl-4-(2-oxo-[1,3]oxazepan-3-yl)-phenyl]-5-oxo-pyrrolidin-3-yl}-amide | Σ: 2.7% | $(M+NH_4)^+$ = 509/511 (bromine isotopes) | 2.82 min |
| 51 | (R)-5-bromo-thiophene-2-carboxylic acid-{1-[4-(1[-dioxo-1□$^6$-isothiazolidin-2-yl)-3-methyl-phenyl]-5-oxo-pyrrolidin-3-yl}-amide | Σ: 14.2% | $(M+H)^+$ = 498/500 (bromine isotopes) | 2.89 min |
| 53 | (R)-5-bromo-thiophene-2-carboxylic acid-{1-[3-methyl-4-(2-oxo-pyrrolidin-1-yl)-phenyl]-5-oxo-pyrrolidin-3-yl}-amide | Σ: 2.9% | $(M+H)^+$ = 462/464 (bromine isotopes) | 2.75 min |

| No. | Structural formula | Yield | Mass peak(s) | $R_f$ value or $R_t$ |
|---|---|---|---|---|
| 54 | | Σ: 3.3% | $(M+H)^+ =$ 418/420 (chlorine isotopes) | 2.71 min |
| | (R)-5-chloro-thiophene-2-carboxylic acid-{1-[3-methyl-4-(2-oxo-pyrrolidin-1-yl)-phenyl]-5-oxo-pyrrolidin-3-yl}-amide | | | |
| 55 | | Σ: 3.9% | $(M+H)^+ =$ 408 | 2.62 min |
| | (R)-5-ethynyl-thiophene-2-carboxylic acid-{1-[3-chloro-4-(2-oxo-tetrahydro-pyrimidin-1-yl)-phenyl]-5-oxo-pyrrolidin-3-yl}-amide | | | |
| 56 | | Σ: 1.1% | $(M+H)^+ =$ 492/494 (bromine isotopes) | 2.75 min |
| | (R)-5-bromo-thiophene-2-carboxylic acid-{1-[3-methoxy-4-(2-oxo-piperidin-1-yl)-phenyl]-5-oxo-pyrrolidin-3-yl}-amide | | | |
| 57 | 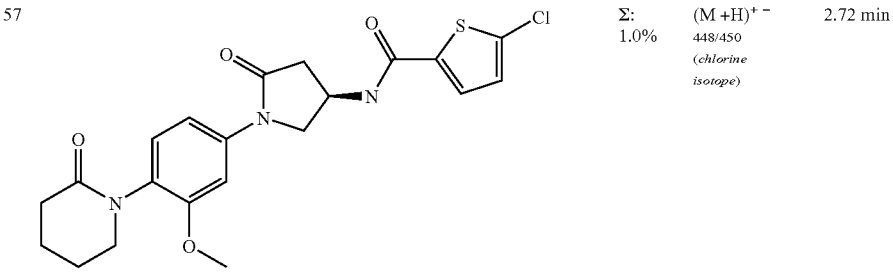 | Σ: 1.0% | $(M+H)^+ =$ 448/450 (chlorine isotope) | 2.72 min |
| | (R)-5-chloro-thiophene-2-carboxylic acid-{1-[3-methoxy-4-(2-oxo-piperidin-1-yl)-phenyl]-5-oxo-pyrrolidin-3-yl}-amide | | | |

| No. | Structural formula | Yield | Mass peak(s) | $R_f$ value or $R_t$ |
|---|---|---|---|---|
| 66 | | Σ: 13.8% | $(M+NH_4)^{+-}$ 455/457 (chlorine isotopes) | 2.63 min |

(R)-5-chloro-thiophene-2-carboxylic acid-{1-[3-fluoro-4-(3-oxo-morpholin-4-yl)-phenyl]-5-oxo-pyrrolidin-3-yl}-amide

EXAMPLE 13

5-bromo-thiophene-2-carboxylic acid-{1-[2-fluoro-4-(2-oxo-2H-pyridin-1-yl)-phenyl]-5-oxo-pyrrolidin-3-yl}-amide

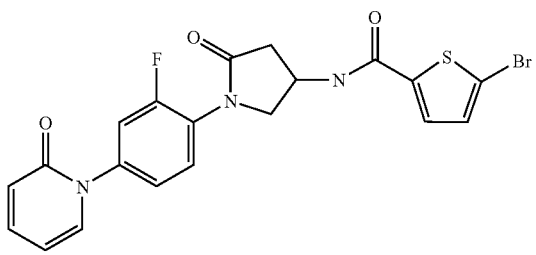

(a) 1-(3-fluoro-4-nitro-phenyl)-1H-pyridin-2-one 2.5 g (26.3 mmol) 2-hydroxypyridine, 2.9 ml (26.3 mmol) 2,4-difluoronitrobenzene, are dissolved in 100 ml acetone, combined with 4.0 g (28.9 mmol) potassium carbonate and stirred for one day at ambient temperature. The undissolved matter is filtered off and the salt residues are rinsed with acetone. The combined organic phases are evaporated to dryness. The residue is purified by chromatography (silica gel; eluant: cyclohexane-ethyl acetate gradient).

Yield: 1.3 g (21%) $R_t$ value: 3.67 min (K value: 4.650) $C_{11}H_7FN_2O_3$ (234.18) Mass spectrum: $(M+H)^+=235$ (b) 1-(4-amino-3-fluoro-phenyl)-1H-pyridin-2-one 1.8 g (7.7 mmol) 1-(3-fluoro-4-nitro-phenyl)-1H-pyridin-2-one are dissolved in 360 ml of ethanol, combined with 8.7 g (38.4 mmol) tin(II)chloride-hydrate and refluxed for 45 min. The mixture is cooled and concentrated to dryness. The residue is combined with equal amounts of 1N sodium hydroxide solution and ethyl acetate. The precipitate is filtered off, water is added to the filtrate, the organic phase is separated off and the aqueous phase is extracted twice with ethyl acetate. The combined organic phases are dried over sodium sulphate and evaporated to dryness.

Yield: quantitative $R_t$ value: 3.03 min (K value: 3.655) $C_{11}H_9FN_2O$ (204.20) Mass spectrum: $(M+H)^+=205$ (c) 1-[2-fluoro-4-(2-oxo-2H-pyridin-1-yl)-phenyl]-5-oxo-pyrrolidine-3-carboxylic acid Prepared analogously to Example 1d from 1-(4-amino-3-fluoro-phenyl)-1H-pyridin-2-one by melting with itaconic acid. The crude product is purified by reversed-phase chromatography.

Yield: 22% $R_t$ value: 2.89 min $C_{16}H_{13}FN_2O_4$ (316.28) Mass spectrum: $(M+H)^+=317$ (d) tert. butyl {-[2-fluoro-4-(2-oxo-2H-pyridin-1-yl)-phenyl]-5-oxo-pyrrolidin-3-yl}-carbamate Prepared analogously to Example 1e from 1-[2-fluoro-4-(2-oxo-2H-pyridin-1-yl)-phenyl]-5-oxo-pyrrolidine-3-carboxylic acid by carboxylic acid breakdown by means of DPPA, tert.-butanol and triethylamine.

Yield: 19% $R_t$ value: 3.91 min (K value: 5.011) $C_{20}H_{22}FN_3O_4$ (387.41) Mass spectrum: $(M+H)^+=388$ (e) 1-[4-amino-2-oxo-pyrrolidin-1-yl)-3-fluoro-phenyl]-1H-pyridin-2-one-hydrochloride 154 mg (0.4 mmol) tert. butyl {1-[2-fluoro-4-(2-oxo-2H-pyridin-1-yl)-phenyl]-5-oxo-pyrrolidin-3-yl}-carbamate are suspended in 5 ml hydrochloric acid solution in dioxane (4-molar) and stirred for 45 minutes at ambient temperature. Then a further 5 ml hydrochloric acid solution in dioxane are added and the mixture is stirred for another two hours.

The suspension is evaporated to dryness.

Yield: quantitative $R_t$ value: 2.76 min (K value: 3.247) $C_{15}H_{14}FN_3O_2$ (287.30) Mass spectrum: $(M+H)^+=288$ (f) 5-bromo-thiophene-2-carboxylic acid-{1-[2-fluoro-4-(2-oxo-2H-pyridin-1-yl)-phenyl]-5-oxo-pyrrolidin-3-yl}-amide Prepared analogously to Example 1g from 5-bromo-thiophene-2-carboxylic acid and 1-[4-amino-2-oxo-pyrrolidin-1-yl)-3-fluoro-phenyl]-1H-pyridin-2-one-hydrochloride with TBTU and NMM in DMF and subsequent purification by reversed-phase chromatography.

Yield: 35% $R_t$ value: 4.12 min (K value: 5.337) $C_{20}H_{15}BrFN_3O_3S$ (476.32) Mass spectrum: $(M+H)^+=476/478$ (bromine isotope)

The following compound was prepared analogously:

| No. | Structural formula / Name | Yield | Mass peak(s) | $R_f$ value or $R_t$ |
|---|---|---|---|---|
| 14 | 5-chloro-thiophene-2-carboxylic acid-{1-[2-fluoro-4-(2-oxo-2H-pyridin-1-yl)-phenyl]-5-oxo-pyrrolidin-3-yl}-amide | Σ: 0.5% | $(M + H)^{+ -}$ 432/434 (chlorine isotopes) | 4.05 min |

EXAMPLE 18

5-bromo-thiophene-2-carboxylic acid-{(3R,4R)-4-methyl-1-[3-methyl-4-(3-oxo-morpholin-4-yl)-phenyl]-5-oxo-pyrrolidin-3-yl}-amide

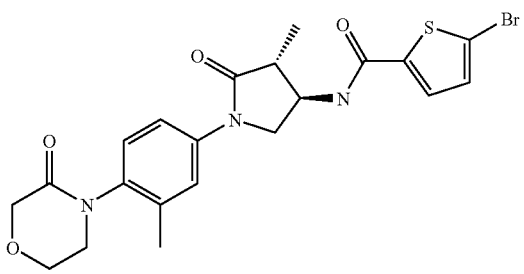

(a) Benzyl [(3R,4R)-4-methyl-5-oxo-tetrahydrofuran-3-yl]-carbamate

272 μl (1.9 mmol) diisopropylamine are placed in 3 ml THF and while cooling with ice 1.2 ml (1.9 mmol) of an n-butyllithium solution in hexane (1.6M) are added. The mixture is stirred for 10 minutes at 0° C., then cooled to −78° C. and a solution of 200 mg (0.85 mmol) benzyl (R)-(5-oxo-tetrahydrofuran-3-yl)-carbamate in 1 ml THF is added dropwise. The mixture is stirred for one hour at −78° C. Then 210 μl (3.3 mmol) methyl iodide are added dropwise, and the mixture is heated to −60° C. within one hour. Then 0.5 ml sat. ammonium chloride solution is added and the mixture is heated to ambient temperature. Water is added and the mixture is extracted three times with ethyl acetate. The combined organic phases are dried over sodium sulphate and evaporated to dryness. The residue is taken up in DMF, acidified with TFA and purified by reversed-phase chromatography.

Yield: 78 mg (37%) $R_t$ value: 2.73 min $C_{13}H_{15}NO_4$ (249.26) Mass spectrum: $(M-H)^- = 248$ (b) benzyl {(1R,2R)-1-hydroxymethyl-2-[3-methyl-4-(3-oxo-morpholin-4-yl)-phenylcarbamoyl]-propyl}-carbamate Prepared analogously to Example 2b from 4-(4-amino-2-methyl-phenyl)-morpholin-3-one and benzyl [(3R,4R)-4-methyl-5-oxo-tetrahydrofuran-3-yl]-carbamate with trimethylaluminium in THF and subsequent purification by reversed-phase chromatography.

Yield: 40% $R_t$ value: 2.48 min $C_{24}H_{29}N_3O_6$ (455.50) Mass spectrum: $(M+H)^+ = 456$ (c) benzyl {(3R,4R)-4-methyl-1-[3-methyl-4-(3-oxo-morpholin-4-yl)-phenyl]-5-oxo-pyrrolidin-3-yl}-carbamate Prepared analogously to Example 2c from benzyl {(1R,2R)-1-hydroxymethyl-2-[3-methyl-4-(3-oxo-morpholin-4-yl)-phenylcarbamoyl]-propyl}-carbamate with di-tert.-butyl azodicarboxylate and tributylphosphine in THF and subsequent purification by reversed-phase chromatography.

Yield: 57% $R_t$ value: 2.74 min $C_{24}H_{27}N_3O_5$ (437.39) Mass spectrum: $(M+H)^+ = 438$ (d) 4-{4-[(3R,4R)-4-amino-3-methyl-2-oxo-pyrrolidin-1-yl]-2-methyl-phenyl}-morpholin-3-one Prepared analogously to Example 2d from benzyl {(3R,4R)-4-methyl-1-[3-methyl-4-(3-oxo-morpholin-4-yl)-phenyl]-5-oxo-pyrrolidin-3-yl}-carbamate and subsequent purification by chromatography on silica gel.

Yield: 98% $R_f$ value: 0.05 (silica gel; dichloromethane/methanol 95:5) $C_{16}H_{21}N_3O_3$ (303.36) Mass spectrum: $(M+H)^+ = 304$ (e) 5-bromo-thiophene-2-carboxylic acid-{(3R,4R)-4-methyl-1-[3-methyl-4-(3-oxo-morpholin-4-yl)-phenyl]-5-oxo-pyrrolidin-3-yl}-amide Prepared analogously to Example 1d from 5-bromo-thiophene-2-carboxylic acid and 4-{4-[(3R,4R)-4-amino-3-methyl-2-oxo-pyrrolidin-1-yl]-2-methyl-phenyl}-morpholin-3-one with TBTU and NMM in DMF and subsequent purification by reversed-phase chromatography.

Yield: 31% $R_t$ value: 2.83 min $C_{21}H_{22}BrN_3O_4S$ (492.39) Mass spectrum: $(M+H)^+ = 492/494$ (bromine isotope)

The following compounds were prepared analogously:

| No. | Structural formula | Yield | Mass peak(s) | $R_f$ value or $R_t$ |
|---|---|---|---|---|
| | uz,4/7 Name | | | |
| 25 | | Σ: 2.6% | $(M + H)^+$ = 438 | 2.67 min |
| | 5-ethynyl-thiophene-2-carboxylic acid-{(3R, 4R)-4-methyl-1-[3-methyl-4-(3-oxo-morpholin-4-yl)-phenyl]-5-oxo-pyrrolidin-3-yl}-amide | | | |
| 52 | | Σ: 0.7% | $(M + H)^+$ = 520/522 (bromine isotopes) | 3.03 min |
| | 5-bromo-thiophene-2-carboxylic acid-{(3R, 4R)-1-[3-methyl-4-(3-oxo-morpholin-4-yl)-phenyl]-5-oxo-4-propyl-pyrrolidin-3-yl}-amide | | | |
| 58 | | Σ: 1.0% | $(M + H)^+$ = 522/524 (bromine isotopes) | 2.76 min |
| | 5-bromo-thiophene-2-carboxylic acid-{(3R, 4R)-4-methoxymethyl-1-[3-methyl-4-(3-oxo-morpholin-4-yl)-phenyl]-5-oxo-pyrrolidin-3-yl}-amide | | | |

-continued

| No. | Structural formula | Yield | Mass peak(s) | $R_f$-value or $R_t$ |
|---|---|---|---|---|
| 59 | | Σ: 4.0% | (M + H)⁺ = 524/526 (chlorine isotopes) | 3.13 min |

5-chloro-thiophene-2-carboxylic acid-{(3R, 4R)-4-benzyl-1-[3-methyl-4-(3-oxo-morpholin-4-yl)-phenyl]-5-oxo-pyrrolidin-3-yl}-amide

| 60 | | Σ: 4.0% | (M + H)⁺ = 568/570 (bromine isotopes) | 3.13 min |

5-bromo-thiophene-2-carboxylic acid-{(3R, 4R)-4-benzyl-1-[3-methyl-4-(3-oxo-morpholin-4-yl)-phenyl]-5-oxo-pyrrolidin-3-yl}-amide

| 61 | 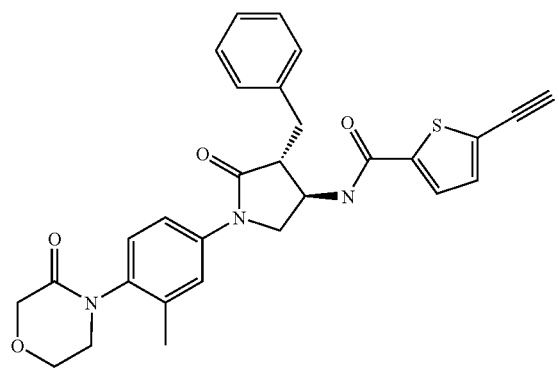 | Σ: 3.4% | (M + H)⁺ = 514 | 3.01 min |

5-ethynyl-thiophene-2-carboxylic acid-{(3R, 4R)-4-benzyl-1-[3-methyl-4-(3-oxo-morpholin-4-yl)-phenyl]-5-oxo-pyrrolidin-3-yl}-amide -continued

| No. | Structural formula | Yield | Mass peak(s) | R$_f$ value or R$_t$ |
|---|---|---|---|---|
| 62 | 5-chloro-thiophene-2-carboxylic acid-{(3R, 4R)-4-methoxymethyl-5-oxo-1-[4-(3-oxo-morpholin-4-yl)-phenyl]-pyrrolidin-3-yl}-amide | Σ: 0.5% | (M − H)$^-$ = 462/464 (chlorine isotopes) | 2.68 min |
| 63 | 5-chloro-thiophene-2-carboxylic acid-{(3R, 4R)-4-allyl-1-[3-methyl-4-(3-oxo-morpholin-4-yl)-phenyl]-5-oxo-pyrrolidin-3-yl}-amide | Σ: 0.8% | (M − H)$^-$ = 472/474 (chlorine isotopes) | 2.79 min |
| 64 | 5-bromo-thiophene-2-carboxylic acid-{(3R, 4R)-4-allyl-1-[3-methyl-4-(3-oxo-morpholin-4-yl)-phenyl]-5-oxo-pyrrolidin-3-yl}-amide | Σ: 0.8% | (M + H)$^+$ = 518/520 (bromine isotopes) | 2.94 min |
| 67 | 5-chloro-thiophene-2-carboxylic acid-{(3R, 4R)-4-methoxymethyl-1-[3-methyl-4-(3-oxo-morpholin-4-yl)-phenyl]-5-oxo-pyrrolidin-3-yl}-amide | Σ: 0.8% | (M + NH$_4$)$^+$ = 495/497 (chlorine isotopes) | 2.68 min |

EXAMPLE 24

5-bromo-thiophene-2-carboxylic acid-{1-[3-methyl-4-(2-oxo-[1,3]oxazepan-3-yl)-phenyl]-5-oxo-pyrrolidin-3-yl}-amide

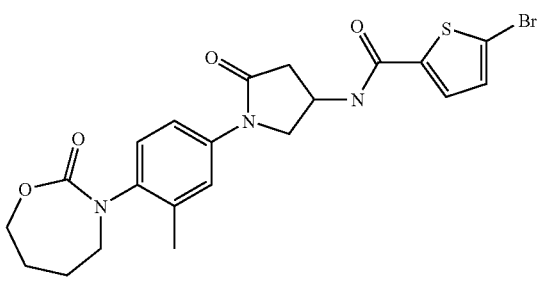

(a) 4-chlorobutyl (2-methyl-4-nitro-phenyl)-carbamate

Prepared from 2-methyl-4-nitroaniline and diphosgene and subsequent reaction with 4-chloro-butan-1-ol analogously to Example1a and subsequent recrystallisation from cyclohexane.

Yield: 68% $R_f$ value: 5.21 min $C_{12}H_{15}ClN_2O_4$ (286.71) Mass spectrum: $(M+H)^+=285/287$ (chlorine isotopes)

(b) 3-(2-methyl-4-nitro-phenyl)-[1,3]oxazepan-2-one 20.2 g (63.4 mmol) 4-chlorobutyl (2-methyl-4-nitro-phenyl)-carbamate are dissolved in 500 ml DMF and added to a suspension of 7.8 g (69.8 mmol) potassium-tert.-butoxide in 500 ml DMF. The reaction solution is stirred for four hours at 90° C.; then the solvent is eliminated in vacuo using the rotary evaporator. The residue is combined with water and extracted three times with ethyl acetate. The combined organic phases are extracted twice with sat. ammonium chloride solution, then dried over sodium sulphate and filtered. The filtrate is evaporated to dryness i. vac. The residue is purified by reversed phase HPLC.

Yield: 1.95 g (12%) $R_f$ value: 4.26 min $C_{12}H_{14}N_2O_4$ (250.25) Mass spectrum: $(M+H)^+=251$ (c) 3-(4-amino-2-methyl-phenyl)-[1,3]oxazepan-2-one 1.95 g (7.79 mmol) 3-(2-methyl-4-nitro-phenyl)-[1,3]oxazepan-2-one are dissolved in 200 ml of tetrahydrofuran and combined with 700 mg Raney nickel. The mixture is hydrogenated in a Parr apparatus at ambient temperature at 1 bar hydrogen pressure for four hours. Then the catalyst is filtered off and the filtrate is evaporated down i. vac.

Yield: quantitative $R_f$ value: 2.76 min $C_{12}H_{16}N_2O_2$ (220.27) Mass spectrum: $(M+H)^+=221$ (d) 3-[2-methyl-4-(4-nitro-2-oxo-pyrrolidin-1-yl)-phenyl]-[1,3]oxazepan-2-one 1.52 g (6.89 mmol) 3-(4-amino-2-methyl-phenyl)-[1,3]oxazepan-2-one and 1.0 g (6.89 mmol) methyl 3-nitro-but-3-enoate (prepared analogously to M. Mühlstädt, B. Schulze *J. Prakt. Chem.* 1971, 313(4), 745-753) are melted together at 130° C. for 50 minutes. The mixture is allowed to cool and dissolved in DMF. The solution is acidified with TFA and purified by chromatography using reversed phase HPLC.

Yield: 100 mg (4%) $R_f$ value: 3.93 min $C_{16}H_{19}N_3O_5$ (333.34) Mass spectrum: $(M+H)^+=334$ (e) 3-[4-(4-amino-2-oxo-pyrrolidin-1-yl)-2-methyl-phenyl]-[1,3]oxazepan-2-one-trifluoroacetate 36 mg (150 μmol) nickel(II)chloride-hexahydrate are dissolved in 2 ml of methanol by treatment with ultrasound and combined with 15 mg (396 μmol) sodium borohydride. 100 mg (300 μmol) of 3-[2-methyl-4-(4-nitro-2-oxo-pyrrolidin-1-yl)-phenyl]-[1,3]-oxazepan-2-one are dissolved in 2 ml of methanol and added in two batches to the reaction solution. After the first quantity has been added a further 21 mg (555 μmol) sodium borohydride are put in. Then the remaining solution of the nitro compound is added in sequence followed by another 21 mg (555 μmol) of sodium borohydride. The mixture is then stirred for five hours at ambient temperature, acidified with TFA and purified by chromatography through reversed phase HPLC.

Yield: 30 mg (33%) $R_f$ value: 3.10 min $C_{16}H_{21}N_3O_3$ (303.36) Mass spectrum: $(M+H)^+=304$ (f) 5-bromo-thiophene-2-carboxylic acid-{1-[3-methyl-4-(2-oxo-[1,3]oxazepan-3-yl)-phenyl]-5-oxo-pyrrolidin-3-yl}-amide Prepared from 3-[4-(4-amino-2-oxo-pyrrolidin-1-yl)-2-methyl-phenyl]-[1,3]-oxazepan-2-one-trifluoroacetate, TBTU, NMM and 5-bromo-thiophene-2-carboxylic acid analogously to Example 1g and subsequent purification by reversed-phase chromatography.

Yield: 63% $R_f$ value : 4.50 min $C_{21}H_{22}BrN_3O_4S$ (492.39) Mass spectrum: $(M+H)^+=492/494$ (bromine isotope)

EXAMPLE 26

(R)-5-bromo-thiophene-2-carboxylic acid-{1-[6-methyl-5-(3-oxo-morpholin-4-yl)-pyridin-2-yl]-5-oxo-pyrrolidin-3-yl}-amide

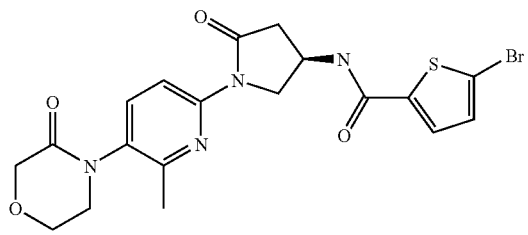

(a) benzyl (R)-[1-hydroxymethyl-2-(6-methyl-5-nitro-pyridin-2-yl-carbamoyl)-ethyl]-carbamate Prepared analogously to Example 2b from 6-methyl-5-nitro-pyridin-2-ylamine and benzyl (R)-(5-oxo-tetrahydrofuran-3-yl)-carbamate with trimethylaluminium activation in THF and subsequent purification by chromatography on silica gel (dichloromethane/methanol 20:1).

Yield: 13% $R_f$ value: 0.29 (silica gel, dichloromethane/methanol 95:5) $R_f$ value: 2.81 min $C_{18}H_{20}N_4O_6$ (388.38) Mass spectrum: $(M+H)^+=389$ (b) benzyl (R)-[1-(6-methyl-5-nitro-pyridin-2-yl)-5-oxo-pyrrolidin-3-yl]-carbamate Prepared analogously to Example 2c from benzyl (R)-[1-hydroxymethyl-2-(6-methyl-5-nitro-pyridin-2-yl-carbamoyl)-ethyl]-carbamate with di-tert.-butyl azodicarboxylate and tributylphosphine in THF and subsequent purification by reversed-phase chromatography.

Yield: 71% $R_f$ value: 3.08 min $C_{18}H_{18}N_4O_5$ (370.36) Mass spectrum: $(M+H)^+=371$ (c) benzyl (R)-[1-(5-amino-6-methyl-pyridin-2-yl)-5-oxo-pyrrolidin-3-yl]-carbamate 250 mg (0.68 mmol) benzyl (R)-[1-(6-methyl-5-nitro-pyridin-2-yl)-5-oxo-pyrrolidin-3-yl]-carbamate are dissolved in 4 ml THF and 5 mL methanol and combined with 50 mg Raney nickel. The mixture is hydrogenated in a Parr apparatus at ambient temperature at 1 bar hydrogen pressure for four hours. Then the catalyst is filtered off and the filtrate is evaporated down i. vac..

Yield: 200 mg (87%) $R_f$ value: 0.25 (silica gel, dichloromethane/methanol 95:5) $C_{18}H_{20}N_4O_3$ (340.38) Mass spectrum: $(M+H)^+=341$ (d) benzyl (R)-(1{5-[2-(2-chloro-ethoxy)-acetylamino]-6-methyl-pyridin-2-yl}-5-oxo-pyrrolidin-3-yl)-carbamate 200 mg (0.59 mmol) of benzyl (R)-[1-(5-amino-6-methyl-pyridin-2-yl)-5-oxo-pyrrolidin-3-yl]-carbamate and 112 mg (0.71 mmol) of (2-chloro-ethoxy)-acetyl-chloride are dissolved in 2 ml THF, then 246 μl (1.78 mmol) triethylamine is metered in and the mixture is stirred for one hour at ambient temperature. Then the reaction mixture is combined with water and extracted three times with ethyl acetate. The combined organic phases are dried over sodium sulphate, filtered off and the filtrate is evaporated to dryness.

Yield: quantitative $R_t$ value: 2.90 min $C_{22}H_{25}ClN_4O_5$ (460.91) Mass spectrum: $(M+H)^+=461/463$ (chlorine isotopes)

(e) benzyl (R)-{1-[6-methyl-5-(3-oxo-morpholin-4-yl)-pyridin-2-yl]-5-oxo-pyrrolidin-3-yl}-carbamate 50 mg (0.11 mmol) of benzyl (R)-1-{5-[2-(2-chloro-ethoxy)-acetylamino]-6-methyl-pyridin-2-yl}-5-oxo-pyrrolidin-3-yl)-carbamate are dissolved in 1 ml DMF, then 19.0 mg (0.17 mmol) potassium-tert.-butoxide and 1 mg sodium iodide are added. The reaction mixture is heated to 60° C. and stirred for 3 hours at this temperature. Then it is cooled to ambient temperature, the solution is acidified with TFA and purified by reversed-phase chromatography.

Yield: 40 mg (87%) $R_t$ value: 2.65 min $C_{22}H_{24}N_4O_5$ (424.45) Mass spectrum: $(M+H)^+=425$ (f) (R)-4-[6-(4-amino-2-oxo-pyrrolidin-1-yl)-2-methyl-pyridin-3-yl]-morpholin-3-one 230 mg (0.54 mmol) of benzyl (R)-{1-[6-methyl-5-(3-oxo-morpholin-4-yl)-pyridin-2-yl]-5-oxo-pyrrolidin-3-yl}-carbamate are dissolved in 5 ml THF and 10 mL methanol and combined with 180 mg palladium/charcoal. The mixture is hydrogenated in a Parr apparatus at ambient temperature at 1 bar hydrogen pressure for 3 hours. Then the catalyst is filtered off and the filtrate is evaporated down i. vac.

Yield: 148 mg (94%) $R_f$ value: 0.04 (silica gel, dichloromethane/methanol 95:5) $R_t$ value: 1.34 min $C_{14}H_{18}N_4O_3$ (290.32) Mass spectrum: $(M+H)^+=291$ (g) (R)-5-bromo-thiophene-2-carboxylic acid-{1-[6-methyl-5-(3-oxo-morpholin-4-yl)-pyridin-2-yl]-5-oxo-pyrrolidin-3-yl}-amide Prepared from (R)-4-[6-(4-amino-2-oxo-pyrrolidin-1-yl)-2-methyl-pyridin-3-yl]-morpholin-3-one, TBTU, NMM and 5-bromo-thiophene-2-carboxylic acid analogously to Example 1g and subsequent purification by reversed-phase chromatography.

Yield: 64% $R_t$ value: 2.71 min $C_{19}H_{19}BrN_4O_4S$ (479.35) Mass spectrum: $(M+H)^++=479/481$ (bromine isotope)

The following compounds were prepared analogously:

| No. | Structural formula | Yield | Mass peak(s) | $R_f$ value or $R_t$ |
|-----|-------------------|-------|--------------|----------------------|
| | Name | | | |
| 27 | 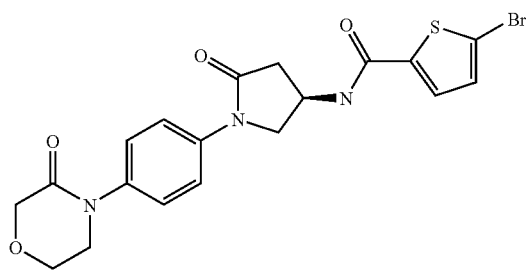<br>(R)-5-bromo-thiophene-2-carboxylic acid-{1-[4-(3-oxo-morpholin-4-yl)-phenyl]-5-oxo-pyrrolidin-3-yl}-amide | Σ: 5.0% | $(M-H)^-=$ 462/464 (bromine isotope) | 2.58 min |
| 28 | 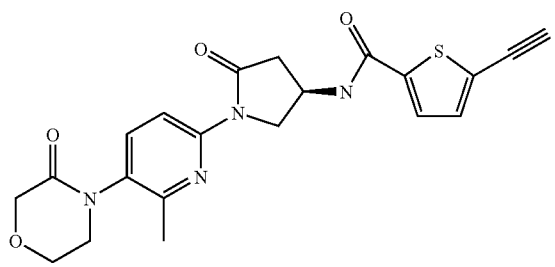<br>(R)-5-ethynyl-thiophene-2-carboxylic acid-{5-oxo-1-[6-methyl-5-(3-oxo-morpholin-4-yl)-pyridin-2-yl]-pyrrolidin-3-yl}-amide | Σ: 3.9% | $(M-H)^-=$ 423 | 2.61 min |

-continued

| No. | Structural formula | Yield | Mass peak(s) | $R_f$ value or $R_t$ |
|---|---|---|---|---|
| 29 | 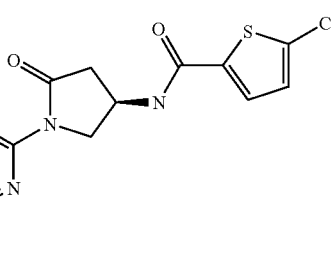 (R)-5-chloro-thiophene-2-carboxylic acid-{1-[6-methyl-5-(3-oxo-morpholin-4-yl)-pyridin-2-yl]-5-oxo-pyrrolidin-3-yl}-amide | Σ: 4.4% | $(M - H)^- =$ 433/435 (bromine isotope) | 2.66 min |
| 30 | 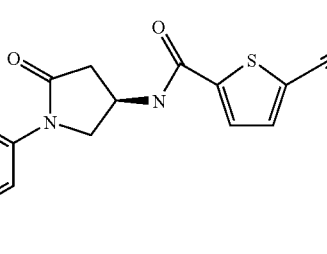 (R)-5-ethynyl-thiophene-2-carboxylic acid-{5-oxo-1-[4-(3-oxo-morpholin-4-yl)-phenyl]-pyrrolidin-3-yl}-amide | Σ: 5.6% | $(M - H)^- =$ 408 | 2.56 min |
| 31 | 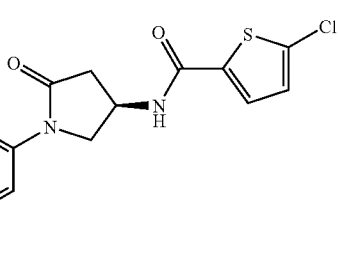 (R)-5-chloro-thiophene-2-carboxylic acid-{5-oxo-1-[4-(3-oxo-morpholin-4-yl)-phenyl]-pyrrolidin-3-yl}-amide | Σ: 3.2% | $(M - H)^- =$ 418/420 (chlorine isotope) | 2.56 min |
| 32 | 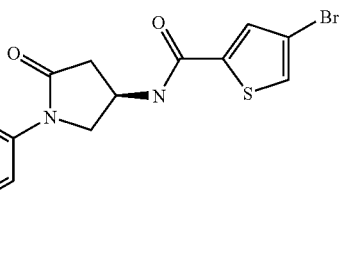 (R)-4-bromo-thiophene-2-carboxylic acid-{1-[5-oxo-4-(3-oxo-morpholin-4-yl)-phenyl]-pyrrolidin-3-yl}-amide | Σ: 4.6% | $(M + H)^+ =$ 454/456 (bromine isotope) | 2.81 min |

| No. | Structural formula | Yield | Mass peak(s) | $R_f$ value or $R_t$ |
|---|---|---|---|---|
| 42 | (R)-4-bromo-thiophene-2-carboxylic acid-{1-[4-(1,1-dioxo-1$\square^6$-[1,2,6]thiadiazinan-2-yl)-3-methyl-phenyl]-5-oxo-pyrrolidin-3-yl}-amide | Σ: 0.7% | $(M + H)^+$ = 513/515 (bromine isotope) | xxx min |
| 43 | (R)-4-bromo-thiophene-2-carboxylic acid-{1-[3-methyl-4-(3-oxo-[1,4]oxazepan-4-yl)-phenyl]-5-oxo-pyrrolidin-3-yl}-amide | Σ: 2.1% | $(M + H)^+$ = 492/494 (bromine isotope) | 2.76 min |

EXAMPLE 38

(R)-5-chloro-thiophene-2-carboxylic acid-{1-[4-(1,1-dioxo-1$\square^6$-[1,2]thiazinan-2-yl)-phenyl]-5-oxo-pyrrolidin-3-yl}-amide

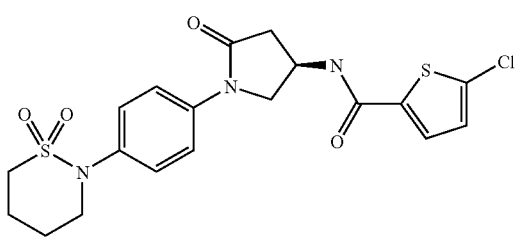

(a) 2-(4-nitrophenyl)-[1,2]thiazinane-1,1-dioxide 500 mg (3.7 mmol) [1,2]thiazinane-1,1-dioxide, dissolved in 10 ml DMF, are added to a suspension of 163 mg sodium hydride dispersion in mineral oil (60%, 4.07 mmol) in 5 ml DMF. The mixture is stirred for 15 minutes, then a solution of 522 mg (3.7 mmol) 1-fluoro-4-nitrobenzene in 10 ml DMF is added dropwise. After two hours the reaction mixture is poured onto ice water. The solid is filtered off, washed with water and dried.

Yield: 707 mg (75%) $R_t$ value: 4.45 min $C_{10}H_{12}N_2O_4S$ (256.28) Mass spectrum: $(M+H)^+$=257

(b) 4-(1,1-dioxo-1$\square^6$-[1,2]thiazinan-2-yl)-phenylamine

Prepared from 2-(4-nitrophenyl)-[1,2]thiazinan-1,1-dioxide analogously to Example 1c with Raney nickel in methanol under 50 psi hydrogen pressure.

Yield: 91% $R_t$ value: 2.94 min $C_{10}H_{14}BrN_2O_2S$ (226.30) Mass spectrum: $(M+H)^+$=227

(c) benzyl (R)-(1-{[4-(1,1-dioxo-1$\square^6$-[1,2]thiazinan-2-yl)-phenylcarbamoyl]-methyl}-2-hydroxy-ethyl)-carbamate Prepared analogously to Example 2b from 4-(1,1-dioxo-1$\square^6$-[1,2]thiazinan-2-yl)-phenylamine and benzyl (R)-(5-oxo-tetrahydrofuran-3-yl)-carbamate with trimethylaluminium activation in THF and subsequent purification by chromatography on silica gel (dichloromethane/methanol 20:1).

Yield: 22% $R_t$ value: 4.08 min (K-factor: 5.087) $C_{22}H_{27}N_3O_6S$ (461.53) Mass spectrum: $(M+H)^+$=462

(d) benzyl (R)-{1-[4-(1,1-dioxo-1$\square^6$-[1,2]thiazininan-2-yl)-phenyl]-5-oxo-pyrrolidin-2-yl}-carbamate Prepared analogously to Example 2c from benzyl (R)-(1-{[4-(1,1-dioxo-1$\square^6$-[1,2]thiazinan-2-yl)-phenylcarbamoyl]-methyl}-2-hydroxy-ethyl)-carbamate with di-tert.-butyl azodicarboxylate and tributylphosphine in THF and subsequent purification by chromatography on silica gel (dichloromethane/methanol 20:1).

Yield: 84% $R_t$ value: 2.88 min $C_{18}H_{18}N_4O_5$ (443.52) Mass spectrum: $(M+H)^+$=444

(e) (R)-4-amino-1-[4-(1,1-dioxo-1$\square^6$-[1,2]thiazinan-2-yl)-phenyl]-pyrrolidin-2-one Prepared analogously to Example 2d from benzyl (R)-{1-[4-(1,1-dioxo-1-$\square^6$-[1,2]thiazininan-2-yl)-phenyl]-5-oxo-pyrrolidin-2-yl}-carbamate and subsequent purification by chromatography on silica gel (dichloromethane/methanol 20:1).

Yield: 43% $R_t$ value: 1.85 min $C_{14}H_{19}N_3O_3S$ (309.39) Mass spectrum: $(M+H)^+$=310

(f) (R)-5-chloro-thiophene-2-carboxylic acid-{1-[4-(1,1-dioxo-1☐⁶-[1,2]thiazinan-2-yl)-phenyl]-5-oxo-pyrrolidin-3-yl}-amide Prepared from (R)-4-amino-1-[4-(1,1-dioxo-1☐⁶-[1,2]thiazinan-2-yl)-phenyl]-pyrrolidin-2-one, TBTU, NMM and 5-chloro-thiophene-2-carboxylic acid analogously to Example 1g and subsequent purification by reversed-phase chromatography.

Yield: 61% $R_f$ value: 2.89 min $C_{19}H_{20}ClN_3O_4S_2$ (453.97)
Mass spectrum: (M+H)⁺=454/456 (chlorine isotopes)
The following compounds were prepared analogously:

at this temperature and then cooled to −80° C. Then 100 mg of (R)-5-bromo-thiophene-2-carboxylic acid-{1-[3-methyl-4-(3-oxo-morpholin-4-yl)-phenyl]-5-oxo-pyrrolidin-3-yl}-amide (209 μmol), dissolved in 1 ml THF, are added dropwise. The mixture is stirred for 30 minutes at −80° C. 77 mg (2R,8aS)-(+)-(camphorylsulphonyl)-oxaziridine (336 μmol), dissolved in 1 ml THF, are added dropwise to this mixture. Within 1.5 hours the mixture is heated to −60° C. 0.5 ml saturated ammonium chloride solution is added and the mixture is further heated to ambient temperature. The mixture is combined with water and extracted three times with ethyl

| No. | Structural formula<br>Name | Yield | Mass peak(s) | $R_f$ value or $R_t$ |
|---|---|---|---|---|
| 39 | (R)-5-bromo-thiophene-2-carboxylic acid-{1-[4-(1,1-dioxo-1☐⁶-[1,2]thiazinan-2-yl)-phenyl]-5-oxo-pyrrolidin-3-yl}-amide | Σ:<br>2.9% | (M − H)⁻=<br>498/500<br>(bromine<br>isotope) | 2.91 min |
| 40 | (R)-5-ethynyl-thiophene-2-carboxylic acid-{1-[4-(1,1-dioxo-1☐⁶-[1,2]thiazinan-2-yl)-phenyl]-5-oxo-pyrrolidin-3-yl}-amide | Σ:<br>2.2% | (M − H)⁻=444 | 2.82 min |

EXAMPLE 49

5-bromo-thiophene-2-carboxylic acid-{(3R,4S)-4-hydroxy-1-[3-methyl-4-(3-oxo-morpholin-4-yl)-phenyl]-5-oxo-pyrrolidin-3-yl}-amide

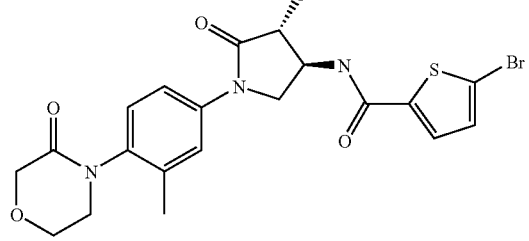

(a) 5-bromo-thiophene-2-carboxylic acid-{(3R,4S)-4-hydroxy-1-[3-methyl-4-(3-oxo-morpholin-4-yl)-phenyl]-5-oxo-pyrrolidin-3-yl}-amide 476 μl butyllithium solution (1.6 M in n-hexane) are added dropwise at 0° C. to a solution of 105 μl diisopropylamine (747 μmol) in 5 ml THF; the mixture is stirred for 10 minutes acetate. The combined organic phases are dried over sodium sulphate, filtered off and the filtrate is evaporated to dryness. The residue is purified by reversed-phase chromatography.

Yield: 31 mg (30%) $R_t$ value: 2.53 min $C_{20}H_{20}BrN_3O_5S$ (494.36) Mass spectrum: (M+H)⁺=494/496 (bromine isotope)

EXAMPLE 65

5-chloro-thiophene-2-carboxylic acid-{3-methyl-1-[3-methyl-4-(3-oxo-morpholin-4-yl)-phenyl]-5-oxo-pyrrolidin-3-yl}-amide

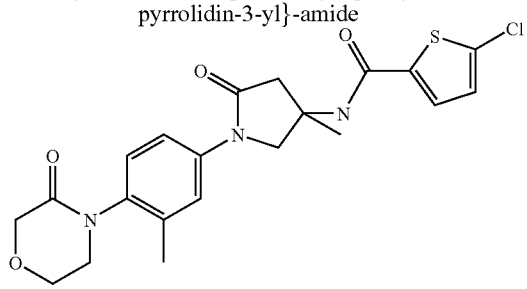

(a) 5-chloro-thiophene-2-carboxylic acid-(3-methyl-5-oxo-tetrahydro-furan-3-yl)-amide 4.45 g (39 mmol) methallyl acetate are placed under argon in a pressurised vessel at −60° C. and combined with 3 ml (34.5 mmol) chlorosulphonyl isocyanate. The pressurised vessel is sealed and the mixture is allowed to heat up to +10° C. within 20 hours. It is then cooled to −60° C. again and the jelly-like mixture is carefully rinsed with 15 ml of ethanol in 25 ml of 5N sodium hydroxide solution. After the initial exothermic reaction has died down the mixture is stirred for one hour at 60° C. Then it is acidified with 20 ml of conc. hydrochloric acid, refluxed for one hour and the solvent is evaporated off under reduced pressure. The viscous residue is dissolved in 60 ml of water and extracted twice with ethyl acetate. The aqueous phase is then lyophilised. 12.6 g of a colourless solid is obtained which is suspended in 80 ml DCM.

5.6 g (34.5 mmol) 5-chlorothiophene-2-carboxylic acid are dissolved in 20 ml of thionyl chloride, combined with one drop of DMF, and refluxed for one hour with stirring. Then excess solvent is eliminated using the rotary evaporator. The crude product, dissolved in 10 ml DCM, is added dropwise to the suspension at −78° C. Then 20 ml (0.14 mol) triethylamine is added and the mixture is heated to ambient temperature for four hours. The mixture is then kept at reflux temperature for a further hour.

The reaction mixture is cooled and the solvents are distilled off. The residue is dissolved in ethyl acetate and washed with 1N hydrochloric acid. The aqueous phase is extracted three times with ethyl acetate. The combined organic phases are washed with 1N sodium hydroxide solution and saturated saline solution, dried over sodium sulphate and evaporated to dryness. The residue thus obtained is purified by chromatography by RP-HPLC. A white solid is obtained.

Yield: 1.48 g (17% over three steps) $R_t$ value: 2.70 min $R_f$ value: 0.70 (silica gel, dichloromethane/methanol 9:1) $C_{10}H_{10}ClNO_3S$ (259.71) Mass spectrum: $(M+H)^+=260/262$ (chlorine isotopes)

(b) 5-chloro-thiophene-2-carboxylic acid-(2-hydroxy-1-methyl-1-{[3-methyl-4-(3-oxo-morpholin-4-yl)-phenylcarbamoyl]-methyl}-ethyl)-amide Prepared analogously to Example 2b from 4-(4-amino-2-methyl-phenyl)-morpholin-3-one and 5-chloro-thiophene-2-carboxylic acid-(3-methyl-5-oxo-tetrahydro-furan-3-yl)-amide with trimethylaluminium activation in THF and subsequent purification by chromatography on silica gel (dichloromethane/methanol 20:1).

Yield: 67% $R_f$ value: 0.30 (silica gel, dichloromethane/methanol 95:5) $C_{21}H_{24}ClN_3O_5S$ (465.95) Mass spectrum: $(M+H)^+=466/468$ (chlorine isotopes)

(c) 5-chloro-thiophene-2-carboxylic acid-{3-methyl-1-[3-methyl-4-(3-oxo-morpholin-4-yl)-phenyl]-5-oxo-pyrrolidin-3-yl}-amide Prepared analogously to Example 2c from 5-chloro-thiophene-2-carboxylic acid-(2-hydroxy-1-methyl-1-{[3-methyl-4-(3-oxo-morpholin-4-yl)-phenylcarbamoyl]-methyl}-ethyl)-amide with diisopropyl azodicarboxylate and triphenylphosphine in THF and subsequent purification by chromatography on silica gel (dichloromethane/methanol 50:1).

Yield: 18% $R_t$ value: 2.54 min $C_{21}H_{22}ClN_3O_4S$ (447.94) Mass spectrum: $(M+H)^+=448/450$ (chlorine isotopes)

What is claimed is:
1. A compound of the formula

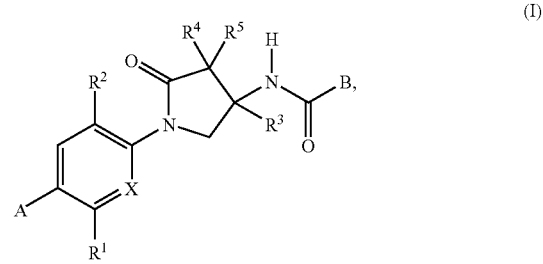

(I)

wherein,

A denotes a group of the formula

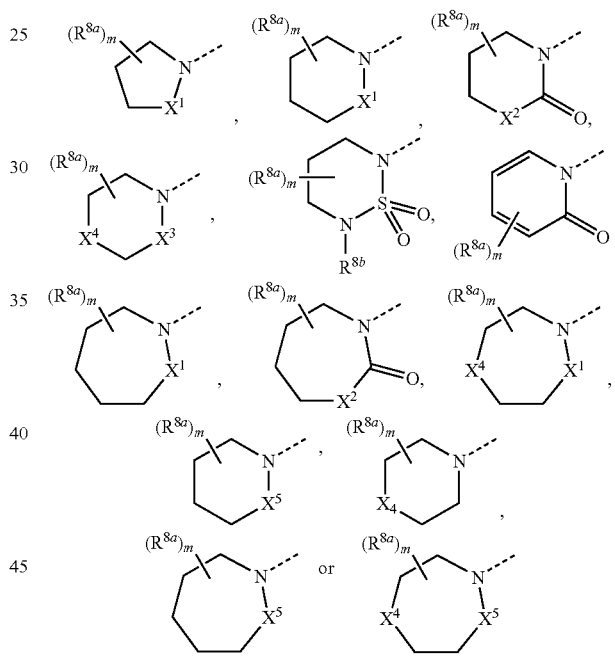

wherein m is the number 1 or 2, $R^{8a}$ in each case independently of one another denote a hydrogen or halogen atom or a $C_{1-5}$-alkyl, hydroxy, hydroxy-$C_{1-5}$-alkyl, $C_{1-5}$-alkoxy, $C_{1-5}$-alkoxy-$C_{1-5}$-alkyl, amino, $C_{1-5}$-alkylamino, di-($C_{1-5}$-alkyl)-amino, amino-$C_{1-5}$-alkyl, $C_{1-5}$-alkylamino-$C_{1-5}$-alkyl, di-($C_{1-5}$-alkyl)-amino-$C_{1-5}$-alkyl, aminocarbonyl, $C_{1-5}$-alkylaminocarbonyl, di-($C_{1-5}$-alkyl)-aminocarbonyl or $C_{1-5}$-alkylcarbonylamino group, while in the previously mentioned substituted 5- to 7-membered groups A the heteroatoms F, Cl, Br, I, O or N optionally introduced with $R^{8a}$ as substituents are not separated by precisely one carbon atom from a heteroatom selected from among N, O and S, $R^{8b}$ each independently of one another denote a hydrogen atom or a $C_{1-5}$-alkyl group, $R^{8c}$ each independently of one another denote a hydrogen atom, a $C_{1-5}$-alkyl, $C_{1-5}$-alkylcarbonyl, $C_{1-5}$-alkyloxycarbonyl or $C_{1-5}$-alkylsulphonyl group, $X^1$ denotes a carbonyl, thiocarbonyl, C=$NR^{8c}$, C=N—$OR^{8c}$, C=N—$NO_2$, C=N—CN or sulphonyl group, $X^2$ denotes an oxygen atom or an —$NR^{8b}$ group, $X^3$ denotes a carbonyl, thiocarbonyl, C=$NR^{8c}$, C=N—$OR^{8c}$, C=N—$NO_2$, C=N—CN or sulphonyl group, $X^4$ denotes an oxygen or sulphur atom or an —$NR^{8c}$ group, $X^5$ denotes an oxygen atom or a —$CH_2$, —$CHR^{8a}$ or —$NR^{8c}$ group, $R^1$ denotes a hydrogen or halogen atom, a $C_{1-3}$-alkyl or $C_{1-3}$-alkoxy group, while the hydrogen atoms of the $C_{1-3}$-alkyl or $C_{1-3}$-alkoxy group may optionally be wholly or partly replaced by fluorine atoms, a $C_{2-3}$-alkenyl, $C_{2-3}$-alkynyl, nitrile, nitro or amino group, $R^2$ denotes a hydrogen or halogen atom or a $C_{1-3}$-alkyl group, X denotes a nitrogen atom or a CH group, $R^3$ denotes a hydrogen atom or a $C_{1-3}$-alkyl group, $R^4$ and $R^5$ each independently of one another denote a hydrogen atom, a hydroxy group, a $OR^9$ group, a $C_{2-6}$-alkenyl or $C_{2-6}$-alkynyl group, a straight-chain or branched $C_{1-6}$-alkyl group, while the hydrogen atoms of the straight-chain or branched $C_{1-6}$-alkyl group may optionally be wholly or partly replaced by fluorine atoms, and which may optionally be substituted by a $C_{3-5}$-cycloalkyl group, a nitrile, hydroxy, a $C_{1-5}$-alkyloxy group, while the hydrogen atoms of the $C_{1-5}$-alkyloxy group may optionally be wholly or partly replaced by fluorine atoms, an allyloxy, propargyloxy, benzyloxy, $C_{1-5}$-alkylcarbonyloxy, $C_{1-5}$-alkyloxycarbonyloxy, carboxy-$C_{1-5}$-alkyloxy, $C_{1-5}$-alkyloxycarbonyl-$C_{1-5}$-alkyloxy, mercapto, $C_{1-5}$-alkylsulphanyl, $C_{1-5}$-alkylsulphonyl, carboxy, $C_{1-5}$-alkyloxycarbonyl, aminocarbonyl, $C_{1-5}$-alkylaminocarbonyl, di-($C_{1-5}$-alkyl)-aminocarbonyl, $C_{3-6}$-cycloalkyleneiminocarbonyl, aminosulphonyl, $C_{1-5}$-alkylaminosulphonyl, di-($C_{1-5}$-alkyl)-aminosulphonyl, $C_{3-6}$-cycloalkyleneiminosulphonyl, amino, $C_{1-5}$-alkylamino, di-($C_{1-5}$-alkyl)-amino, $C_{1-5}$-alkylcarbonylamino, $C_{1-5}$-alkyl-sulphonylamino, N-($C_{1-5}$-alkylsulphonyl)-$C_{1-5}$-alkylamino or $C_{3-6}$-cycloalkylcarbonylamino group, while the 6- to 7-membered cyclic groups of the $C_{3-6}$-cycloalkyleneiminocarbonyl group in the cyclic moiety a methylene group in the 4 position of a 6- or 7-membered cycloalkyleneimino group may be replaced by an oxygen or sulphur atom, by a carbonyl, sulphinyl, sulphonyl or —$NR^{8c}$ group and additionally a methylene group adjacent to an above-mentioned —$NR^{8c}$ group may be replaced by a carbonyl group, a phenyl, or heteroaryl group which may optionally be mono- to trisubstituted in the phenyl or heteroaryl moiety by identical or different substituents selected from among halogen atoms, $C_{1-5}$-alkyl, di-($C_{1-5}$-alkyl)-amino, hydroxy, $C_{1-5}$-alkyloxy, mono-, di- or trifluoromethoxy, carboxy- and $C_{1-5}$-alkyloxycarbonyl groups, a phenyl-$C_{1-5}$-alkyl or heteroaryl-$C_{1-5}$-alkyl group, which may optionally be mono- to trisubstituted in the phenyl or heteroaryl moiety by identical or different substituents selected from among halogen atoms, $C_{1-5}$-alkyl, di-($C_{1-5}$-alkyl)-amino, hydroxy, $C_{1-5}$-alkyloxy, mono-, di- or trifluoromethoxy, carboxy- and $C_{1-5}$-alkyloxycarbonyl groups, and which may optionally be substituted in the $C_{1-5}$-alkyl-moiety by a hydroxy, a $C_{1-5}$-alkyloxy group, while the hydrogen atoms of the $C_{1-5}$-alkyloxy group may optionally be wholly or partly replaced by fluorine atoms, an allyloxy, propargyloxy, benzyloxy, $C_{1-5}$-alkylcarbonyloxy, $C_{1-5}$-alkyloxycarbonyloxy, carboxy-$C_{1-5}$-alkyloxy, or a $C_{1-5}$-alkyloxycarbonyl-$C_{1-5}$-alkyloxy group;

a 3- to 7-membered cycloalkyl, cycloalkyleneimino, cycloalkyl-$C_{1-5}$-alkyl or cycloalkyleneimino-$C_{1-3}$-alkyl group, wherein in 4- to 7-membered cyclic groups in the cyclic moiety a methylene group may optionally be replaced by an —$N(R^{8c})$ group, an oxygen or sulphur atom or a —S(O) or —$S(O)_2$ group, or wherein in 4- to 7-membered cyclic groups in the cyclic moiety two adjacent methylene groups together may optionally be replaced by a —C(O)N ($R^{8b}$) or —$S(O)_2N(R^{8b})$ group, or wherein in 6- to 7-membered cyclic groups in the cyclic moiety three adjacent methylene groups together may optionally be replaced by a substituted —$OC(O)N(R^{8b})$ or —$N(R^{8b})C(O)N(R^{8b})$ or —$N(R^{8b})S(O)_2N(R^{8b})$ group, with the proviso that a 3- to 7-membered cycloalkyl, cycloalkyleneimino, cycloalkyl-$C_{1-5}$-alkyl or cycloalkyleneimino-$C_{1-3}$-alkyl group as hereinbefore defined wherein two heteroatoms from the group oxygen and nitrogen are separated from one another by precisely one optionally substituted —$CH_2$ group, is excluded, while a 3- to 7-membered cycloalkyl, cycloalkyleneimino, cycloalkyl-$C_{1-5}$-alkyl or cycloalkyleneimino-$C_{1-3}$-alkyl group as hereinbefore defined may be substituted at one or two —$CH_2$ groups by one or two $C_{1-3}$-alkyl groups in each case, with the proviso that $R^4$ and $R^5$ may not simultaneously be defined as hydroxy or $OR^9$ groups, or $R^4$ and $R^5$ together with the carbon atom to which they are bound form a $C_{3-8}$-cycloalkyl or $C_{3-8}$-cycloalkenyl group, while one of the methylene groups of a $C_{4-8}$-cycloalkyl group may be replaced by an oxygen or sulphur atom or an —$N(R^{8c})$, or a carbonyl, sulphinyl or sulphonyl group, and/or two directly adjacent methylene groups of a $C_{4-8}$-cycloalkyl group may together be replaced by a —$C(O)N(R^{8b})$ or —$S(O)_2N(R^{8b})$ group, and/or three directly adjacent methylene groups of a $C_{6-8}$-cycloalkyl group may together be replaced by a —$OC(O)N(R^{8b})$, —$N(R^{8b})C(O)N(R^{8b})$ or —$N(R^{8b})S(O)_2 N(R^{8b})$ group, while 1 to 3 carbon atoms of a $C_{3-8}$-cycloalkyl group may optionally be substituted independently of one another by in each case one or two identical or different halogen atoms or $C_{1-5}$-alkyl, nitrile, hydroxy, $C_{1-5}$-alkyloxy, $C_{1-5}$-alkylcarbonyloxy, carboxy-$C_{1-5}$-alkyl, $C_{1-5}$-alkyloxycarbonyl-$C_{1-5}$-alkyl, $C_{1-5}$-alkylsulphanyl, $C_{1-5}$-alkylsulphonyl, carboxy, $C_{1-5}$-alkyloxycarbonyl, aminocarbonyl, $C_{1-5}$-alkylaminocarbonyl, di-($C_{1-5}$-alkyl)-aminocarbonyl, $C_{3-6}$-cycloalkyleneiminocarbonyl, aminosulphonyl, $C_{1-5}$-alkylaminosulphonyl, di-($C_{1-5}$-alkyl)-aminosulphonyl, $C_{3-6}$-cycloalkyleneiminosulphonyl, amino, $C_{1-5}$-alkylamino, di-($C_{1-5}$-alkyl)-amino, $C_{1-5}$-alkylcarbonylamino, $C_{1-5}$-alkylsulphonylamino, N-($C_{1-5}$-alkylsulphonyl)-$C_{1-5}$-alkylamino or $C_{3-6}$-cycloalkylcarbonylamino groups, while 1 to 2 carbon atoms of a $C_{3-8}$-cycloalkenyl group may optionally be substituted independently of one another by in each case a $C_{1-5}$-alkyl, nitrile, carboxy-$C_{1-5}$-alkyl, $C_{1-5}$-alkyloxycarbonyl-$C_{1-5}$-alkyl, carboxy, $C_{1-5}$-alkyloxycarbonyl, aminocarbonyl, $C_{1-5}$-alkylaminocarbonyl, di-($C_{1-5}$-alkyl)-aminocarbonyl, $C_{3-6}$-cycloalkyleneiminocarbonyl, aminosulphonyl, $C_{1-5}$-alkylaminosulphonyl, di-($C_{1-5}$-alkyl)-aminosulphonyl, $C_{3-6}$-cycloalkyleneiminosulphonyl groups, and 1 to 2 carbon atoms of a $C_{4-8}$-cycloalkenyl group which are not bound by a double bond to another carbon atom, may optionally be substituted independently of one another by a fluorine atom or a hydroxy, $C_{1-5}$-alkyloxy, $C_{1-5}$-alkylcarbonyloxy, $C_{1-5}$-alkylsulphanyl, $C_{1-5}$-alkylsulphonyl, amino, $C_{1-5}$-alkylamino, di-($C_{1-5}$-alkyl)-amino, $C_{1-5}$-alkylcarbonylamino, $C_{1-5}$-alkylsulphonylamino, N-($C_{1-5}$-alkylsulphonyl)-$C_{1-5}$-alkylamino or $C_{3-6}$-cycloalkylcarbonylamino groups, with the proviso that a $C_{3-8}$-cycloalkyl or $C_{3-8}$-cycloalkenyl group of this kind formed from $R^4$ and $R^5$ together, wherein two heteroatoms in the cyclic group selected from among oxygen and nitrogen are separated from one another by precisely one optionally substituted —$CH_2$ group, and/or wherein one or both methylene groups of the cyclic group, which are directly attached to the carbon atom to which the groups $R^4$ and $R^5$ are bound, are replaced by a heteroatom selected from the group among oxygen, nitrogen and sulphur, and/or wherein a substituent bound to the cyclic group, which is characterised in that a heteroatom selected from among oxygen, nitrogen, sulphur and halogen atom is bound directly to the cyclic group, is separated from another heteroatom selected from among oxygen, nitrogen and sulphur, with the exception of the sulphone group, by precisely one optionally substituted methylene group, and/or wherein two oxygen atoms are joined together directly, is excluded, $R^9$ denotes a straight-chain or branched $C_{1-6}$-alkyl group, while the hydrogen atoms of the straight-chain or branched $C_{1-6}$-alkyl group may optionally be wholly or partly replaced by fluorine atoms, and which may optionally be substituted by a $C_{3-5}$-cycloalkyl group, a hydroxy, a $C_{1-5}$-alkyloxy group, while the hydrogen atoms of the $C_{1-5}$-alkyloxy group may optionally be wholly or partly replaced by fluorine atoms, an allyloxy, propargyloxy, benzyloxy, $C_{1-5}$-alkylcarbonyloxy, $C_{1-5}$-alkyloxycarbonyloxy, carboxy-$C_{1-5}$-alkyloxy, $C_{1-5}$-alkyloxycarbonyl-$C_{1-5}$-alkyloxy, carboxy, $C_{1-5}$-alkyloxycarbonyl, aminocarbonyl, $C_{1-5}$-alkylaminocarbonyl, di-($C_{1-5}$-alkyl)-aminocarbonyl, $C_{3-6}$-cycloalkyleneiminocarbonyl, amino, $C_{1-5}$-alkylamino, di-($C_{1-5}$-alkyl)-amino, $C_{1-5}$-alkylcarbonylamino, $C_{1-5}$-alkyl-sulphonylamino, N-($C_{1-5}$-alkylsulphonyl)-$C_{1-5}$-alkylamino or $C_{3-6}$-cycloalkylcarbonylamino group, while the 6- to 7-membered cyclic groups of the $C_{3-6}$-cycloalkyleneiminocarbonyl group in the cyclic moiety a methylene group in the 4 position of a 6- or 7-membered cycloalkyleneimino group may be replaced by an oxygen or sulphur atom, by a carbonyl, sulphinyl, sulphonyl or —$NR^{8c}$ group and additionally a methylene group adjacent to an above-mentioned —$NR^{8c}$ group may be replaced by a carbonyl group, with the proviso that the replacement of hydrogen atoms of the first carbon atom of the straight-chain or branched $C_{1-6}$-alkyl group by substituents from the group comprising oxygen, sulphur or nitrogen is excluded, a phenyl, heteroaryl, phenyl-$C_{1-5}$-alkyl or heteroaryl-$C_{1-5}$-alkyl group, which may optionally be mono- to trisubstituted in the phenyl or heteroaryl moiety by identical or different substituents selected from among halogen atoms, $C_{1-5}$-alkyl, di-($C_{1-5}$-alkyl)-amino, hydroxy, $C_{1-5}$-alkyloxy, mono-, di- or trifluoromethoxy, carboxy- and $C_{1-5}$-alkyloxycarbonyl groups, a 3- to 7-membered cycloalkyl, cycloalkyl-$C_{1-5}$-alkyl or cycloalkyleneimino-$C_{2-3}$-alkyl group, wherein in 4- to 7-membered cyclic groups in the cyclic moiety a methylene group may optionally be replaced by an —$N(R^{8c})$ group, an oxygen or sulphur atom or a —$S(O)$ or —$S(O)_2$ group, or wherein in 4- to 7-membered cyclic groups in the cyclic moiety two adjacent methylene groups together may optionally be replaced by a —$C(O)N(R^{8b})$ or —$S(O)_2N(R^{8b})$ group, or wherein in 6- to 7-membered cyclic groups in the cyclic moiety three adjacent methylene groups together may optionally be replaced by a substituted —$OC(O)N(R^{8b})$ or —$N(R^{8b})C(O)N(R^{8b})$ or —$N(R^{8b})S(O)_2N(R^{8b})$ group, with the proviso that a 3- to 7-membered cycloalkyl, cycloalkyl-$C_{1-5}$-alkyl or cycloalkyleneimino-$C_{2-3}$-alkyl group as hereinbefore defined wherein two heteroatoms from the group comprising oxygen and nitrogen are separated from one another by precisely one optionally substituted —$CH_2$ group, is excluded, while a 3- to 7-membered cycloalkyl, cycloalkyl-$C_{1-5}$-alkyl or cycloalkyleneimino-$C_{2-3}$-alkyl group as hereinbefore defined may be substituted at one or two —$CH_2$ groups by one or two $C_{1-3}$-alkyl groups in each case, B denotes a group of the formula

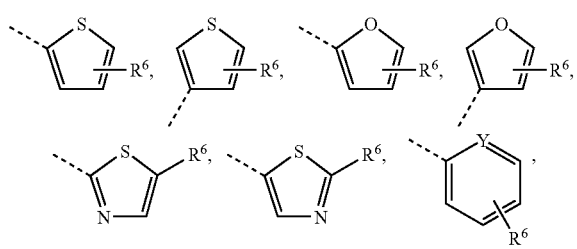

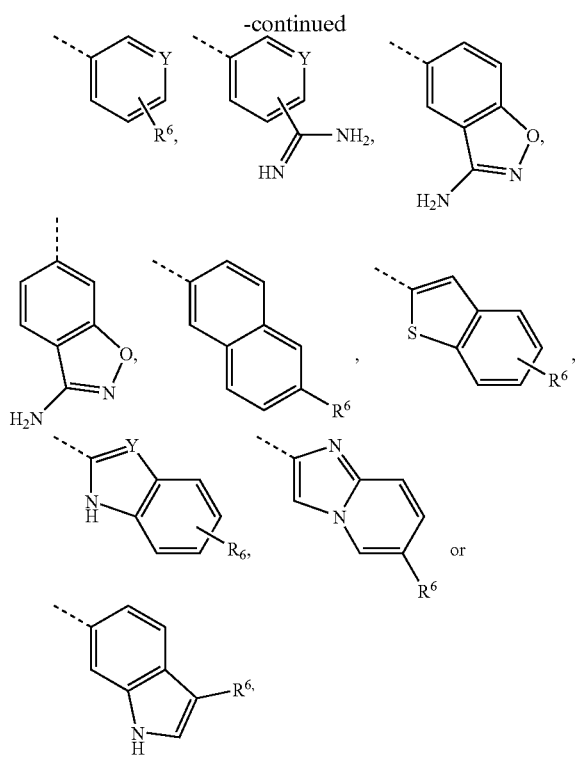

Y denotes a nitrogen atom or a CH group,

R⁶ denotes a hydrogen, a halogen atom, a nitrile group, a $C_{2-3}$-alkenyl, $C_{2-3}$-alkynyl, a $C_{1-3}$-alkyl group, or a $C_{1-3}$-alkoxy group, while the hydrogen atoms of the $C_{1-3}$-alkyl or $C_{1-3}$-alkoxy group may optionally be wholly or partly replaced by fluorine atoms, while, unless otherwise stated, by the term "heteroaryl group" mentioned hereinbefore in the definitions is meant a monocyclic 5- or 6-membered heteroaryl group, while the 6-membered heteroaryl group contains one, two or three nitrogen atoms and the 5-membered heteroaryl group contains an imino group optionally substituted by a $C_{1-3}$-alkyl, phenyl or phenyl-$C_{1-3}$-alkyl group, or an oxygen or sulphur atom or an imino group optionally substituted by a $C_{1-3}$-alkyl, phenyl, amino-$C_{2-3}$-alkyl, $C_{1-3}$-alkylamino-$C_{2-3}$-alkyl, di-($C_{1-3}$-alkyl)-amino-$C_{2-3}$-alkyl, a $C_{3-6}$-cycloalkyleneimino-$C_{1-3}$-alkyl or phenyl-$C_{1-3}$-alkyl group, or an oxygen or sulphur atom and additionally a nitrogen atom or an imino group optionally substituted by a $C_{1-3}$-alkyl or phenyl-$C_{1-3}$-alkyl group and two or three nitrogen atoms, and moreover a phenyl ring optionally substituted by a fluorine, chlorine or bromine atom, a $C_{1-3}$-alkyl, hydroxy, $C_{1-3}$-alkyloxy group, amino, $C_{1-3}$-alkylamino, di-($C_{1-3}$-alkyl)-amino or $C_{3-6}$-cycloalkyleneimino group may be fused to the above-mentioned monocyclic heteroaryl groups via two adjacent carbon atoms and the bond is effected via a nitrogen atom or a carbon atom of the heterocyclic moiety or a fused-on phenyl ring, while, unless otherwise stated, by the term "halogen atom" mentioned hereinbefore in the definitions is meant an atom selected from among fluorine, chlorine, bromine and iodine, while the alkyl, alkenyl, alkynyl and alkoxy groups contained in the above-mentioned definitions which have more than two carbon atoms, unless otherwise stated, be straight-chain or branched and the alkyl groups in the previously mentioned dialkylated groups, for example the dialkylamino groups, may be identical or different, and the hydrogen atoms of the methyl or ethyl groups contained in the foregoing definitions, unless otherwise stated, may be wholly or partly replaced by fluorine atoms, or a tautomer or salt thereof.

2. A compound of the formula I according to claim 1, wherein

A denotes a group of the formula

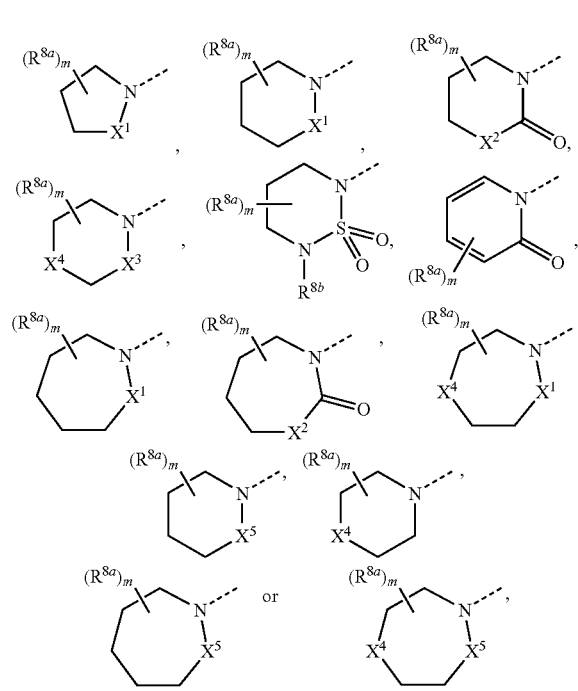

wherein m is the number 1 or 2, $R^{8a}$ each independently of one another denote a hydrogen or halogen atom or a $C_{1-5}$-alkyl, hydroxy, hydroxy-$C_{1-5}$-alkyl, $C_{1-5}$-alkoxy, $C_{1-5}$-alkoxy-$C_{1-5}$-alkyl, amino, $C_{1-5}$-alkylamino, di-($C_{1-5}$-alkyl)-amino, amino-$C_{1-5}$-alkyl, $C_{1-5}$-alkylamino-$C_{1-5}$-alkyl, di-($C_{1-5}$-alkyl)-amino-$C_{1-5}$-alkyl, aminocarbonyl, $C_{1-5}$-alkylaminocarbonyl, di-($C_{-5}$-alkyl)-aminocarbonyl or $C_{1-5}$-alkylcarbonylamino group denotes, while in the previously mentioned substituted 5- to 7-membered groups A the heteroatoms F, Cl, Br, I, O or N optionally introduced with $R^{8a}$ as substituents are not separated by precisely one carbon atom from a heteroatom selected from among N, O and S, $R^{8b}$ each independently of one another denote a hydrogen atom or a $C_{1-5}$-alkyl group, $R^{8c}$ each independently of one another denote a hydrogen atom, a $C_{1-5}$-alkyl, $C_{1-5}$-alkylcarbonyl, $C_{1-5}$-alkyloxycarbonyl or $C_{1-5}$-alkylsulphonyl group, $X^1$ denotes a carbonyl, thiocarbonyl, $C=NR^{8c}$, $C=N-OR^{8c}$, $C=N-NO_2$, $C=N-CN$ or sulphonyl group, $X^2$ denotes an oxygen atom or an $-NR^{8b}$ group, $X^3$ denotes a carbonyl, thiocarbonyl, $C=NR^{8c}$, $C=N-OR^{8c}$, $C=N-NO_2$, $C=N-CN$ or sulphonyl group, $X^4$ denotes an oxygen or sulphur atom or an $-NR^{8c}$ group, $X^5$ denotes an oxygen atom or a $-CH_2$, $-CHR^{8a}$ or $-NR^{8c}$ group, $R^1$ denotes a hydrogen or halogen atom, a $C_{1-3}$-alkyl or $C_{1-3}$-alkoxy group, while the hydrogen atoms of the $C_{1-3}$-alkyl or $C_{1-3}$-alkoxy group may optionally be wholly or partly replaced by fluorine atoms, a $C_{2-3}$-alkenyl, $C_{2-3}$-alkynyl, nitrile, nitro or amino group, $R^2$ denotes a hydrogen or halogen atom or a $C_{1-3}$-alkyl group, X denotes a nitrogen atom or a CH group, $R^3$ denotes a hydrogen atom or a $C_{1-3}$-alkyl group, $R^4$ and $R^5$ each independently of one another denote a hydrogen atom, a hydroxy group, a $OR^9$ group, a $C_{2-6}$-alkenyl or $C_{2-6}$-alkynyl group, a straight-chain or branched $C_{1-6}$-alkyl group, while the hydrogen atoms of the straight-chain or branched $C_{1-6}$-alkyl group may optionally be wholly or partly replaced by fluorine atoms, and which may optionally be substituted by a $C_{3-5}$-cycloalkyl group, a nitrile, hydroxy, a $C_{1-5}$-alkyloxy group, while the hydrogen atoms of the $C_{1-5}$-alkyloxy group may optionally be wholly or partly replaced by fluorine atoms, an allyloxy, propargyloxy, benzyloxy, $C_{1-5}$-alkylcarbonyloxy, $C_{1-5}$-alkyloxycarbonyloxy, carboxy-$C_{1-5}$-alkyloxy, $C_{1-5}$-alkyloxycarbonyl-$C_{1-5}$-alkyloxy, mercapto, $C_{1-5}$-alkylsulphanyl, $C_{1-5}$-alkylsulphonyl, carboxy, $C_{1-5}$-alkyloxycarbonyl, aminocarbonyl, $C_{1-5}$-alkylaminocarbonyl, di-($C_{1-5}$-alkyl)-aminocarbonyl, $C_{3-6}$-cycloalkyleneiminocarbonyl, aminosulphonyl, $C_{1-5}$-alkylaminosulphonyl, di-($C_{1-5}$-alkyl)-aminosulphonyl, $C_{3-6}$-cycloalkyleneiminosulphonyl, amino, $C_{1-5}$-alkylamino, di-($C_{1-5}$-alkyl)-amino, $C_{1-5}$-alkylcarbonylamino, $C_{1-5}$-alkylsulphonylamino, N-($C_{1-5}$-alkylsulphonyl)-$C_{1-5}$-alkylamino or $C_{3-6}$-cycloalkylcarbonylamino group, while the 6- to 7-membered cyclic groups of the $C_{3-6}$-cycloalkyleneiminocarbonyl group in the cyclic moiety a methylene group in the 4 position of a 6- or 7-membered cycloalkyleneimino group may be replaced by an oxygen or sulphur atom, by a carbonyl, sulphinyl, sulphonyl or $-NR^{8c}$ group and additionally a methylene group adjacent to an above-mentioned $-NR^{8c}$ group may be replaced by a carbonyl group, a phenyl or heteroaryl group which may optionally be mono- to trisubstituted in the phenyl or heteroaryl moiety by identical or different substituents selected from among halogen atoms, $C_{1-5}$-alkyl, di-($C_{1-5}$-alkyl)-amino, hydroxy, $C_{1-5}$-alkyloxy, mono-, di- or trifluoromethoxy, carboxy- and $C_{1-5}$-alkyloxycarbonyl groups, a phenyl-$C_{1-5}$-alkyl or heteroaryl-$C_{1-5}$-alkyl group, which may optionally be mono- to trisubstituted in the phenyl or heteroaryl moiety by identical or different substituents selected from among halogen atoms, $C_{1-5}$-alkyl, di-($C_{1-5}$-alkyl)-amino, hydroxy, $C_{1-5}$-alkyloxy, mono-, di- or trifluoromethoxy, carboxy- and $C_{1-5}$-alkyloxycarbonyl groups, and which may optionally be substituted in the $C_{1-5}$-alkyl-moiety by a hydroxy, a $C_{1-5}$-alkyloxy group, while the hydrogen atoms of the $C_{1-5}$-alkyloxy group may optionally be wholly or partly replaced by fluorine atoms, an allyloxy, propargyloxy, benzyloxy, $C_{1-5}$-alkylcarbonyloxy, $C_{1-5}$-alkyloxycarbonyloxy, carboxy-$C_{1-5}$-alkyloxy, or a $C_{1-5}$-alkyloxycarbonyl-$C_{1-5}$-alkyloxy group;

a 3- to 7-membered cycloalkyl, cycloalkyleneimino, cycloalkyl-$C_{1-5}$-alkyl or cycloalkyleneimino-$C_{1-3}$-alkyl group, wherein in 4- to 7-membered cyclic groups in the cyclic moiety a methylene group may optionally be replaced by an $-N(R^{8c})$ group, an oxygen or sulphur atom or a $-S(O)$ or $-S(O)_2$ group, or wherein in 4- to 7-membered cyclic groups in the cyclic moiety two adjacent methylene groups together may optionally be replaced by a $-C(O)N(R^{8b})$ or $-S(O)_2N(R^{8b})$ group, or wherein in 6- to 7-membered cyclic groups in the cyclic moiety three adjacent methylene groups together may optionally be replaced by a substituted $-OC(O)N(R^{8b})$ or $-N(R^{8b})C(O)N(R^{8b})$ or $-N(R^{8b})S(O)_2N(R^{8b})$ group, with the proviso that a 3- to 7-membered cycloalkyl, cycloalkyleneimino, cycloalkyl-$C_{1-5}$-alkyl or cycloalkyleneimino-$C_{1-3}$-alkyl group as hereinbefore defined wherein two heteroatoms from the group comprising oxygen and nitrogen are separated from one another by precisely one optionally substituted $-CH_2$ group, is excluded, while a 3- to 7-membered cycloalkyl, cycloalkyleneimino, cycloalkyl-$C_{1-5}$-alkyl or cycloalkyleneimino-$C_{1-3}$-alkyl group as hereinbefore defined may be substituted at one or two $-CH_2$ groups by one or two $C_{1-3}$-alkyl groups in each case, with the proviso that $R^4$ and $R^5$ cannot simultaneously be defined as hydroxy or $OR^9$ groups, or $R^4$ and $R^5$ together with the carbon atom to which they are bound form a $C_{3-8}$-cycloalkyl or $C_{3-8}$-cycloalkenyl group, while one of the methylene groups of a $C_{4-8}$-cycloalkyl group may be replaced by an oxygen or sulphur atom or an $-N(R^{8c})$, or a carbonyl, sulphinyl or sulphonyl group, and/or two directly adjacent methylene groups of a $C_{4-8}$-cycloalkyl group may together be replaced by a $-C(O)N(R^{8b})$ or $-S(O)_2N(R^{8b})$ group, and/or three directly adjacent methylene groups of a $C_{6-8}$-cycloalkyl group may together be replaced by a $-OC(O)N(R^{8b})$, $-N(R^{8b})C(O)N(R^{8b})$ or $-N(R^{8b})S(O)_2N(R^{8b})$ group, while 1 to 3 carbon atoms of a $C_{3-8}$-cycloalkyl group may optionally be substituted independently of one another by in each case one or two identical or different halogen atoms or $C_{1-5}$-alkyl, nitrile, hydroxy, $C_{1-5}$-alkyloxy, $C_{1-5}$-alkylcarbonyloxy, carboxy-$C_{1-5}$-alkyl, $C_{1-5}$-alkyloxycarbonyl-$C_{1-5}$-alkyl, $C_{1-5}$-alkylsulphanyl, $C_{1-5}$-alkylsulphonyl, carboxy, $C_{1-5}$-alkyloxycarbonyl, aminocarbonyl, $C_{1-5}$-alkylaminocarbonyl, di-($C_{1-5}$-alkyl)-aminocarbonyl, $C_{3-6}$-cycloalkyleneiminocarbonyl, aminosulphonyl, $C_{1-5}$-alkylaminosulphonyl, di-($C_{1-5}$-alkyl)-aminosulphonyl, $C_{3-6}$-cycloalkyleneiminosulphonyl, amino, $C_{1-5}$-alkylamino, di-($C_{1-5}$-alkyl)-amino, $C_{1-5}$-alkylcarbonylamino, $C_{1-5}$-alkyl-sulphonylamino, N-($C_{1-5}$-alkylsulphonyl)-$C_{1-5}$-alkylamino or $C_{3-6}$-cycloalkylcarbonylamino groups, while 1 to 2 carbon atoms of a $C_{3-8}$-cycloalkenyl group may optionally be substituted independently of one another by in each case a $C_{1-5}$-alkyl, nitrile, carboxy-$C_{1-5}$-alkyl, $C_{1-5}$-alkyloxycarbonyl-$C_{1-5}$-alkyl, carboxy, $C_{1-5}$-alkyloxycarbonyl, aminocarbonyl, $C_{1-5}$-alkylaminocarbonyl, di-($C_{1-5}$-alkyl)-aminocarbonyl, $C_{3-6}$-cycloalkyleneiminocarbonyl, aminosulphonyl, $C_{1-5}$-alkylaminosulphonyl, di-($C_{1-5}$-alkyl)-aminosulphonyl, $C_{3-6}$-cycloalkyleneiminosulphonyl groups, and 1 to 2 carbon atoms of a $C_{4-8}$-cycloalkenyl group which are not bound by a double bond to another carbon atom may optionally be substituted independently of one another by a fluorine atom or a hydroxy, $C_{1-5}$-alkyloxy, $C_{1-5}$-alkylcarbonyloxy, $C_{1-5}$-alkylsulphanyl, $C_{1-5}$-alkylsulphonyl, amino, $C_{1-5}$-alkylamino, di-($C_{1-5}$-alkyl)-amino, $C_{1-5}$-alkylcarbonylamino, $C_{1-5}$-alkylsulphonylamino, N-($C_{1-5}$-alkylsulphonyl)-$C_{1-5}$-alkylamino or $C_{3-6}$-cycloalkylcarbonyl-amino groups, with the proviso that a $C_{3-8}$-cycloalkyl or $C_{3-8}$-cycloalkenyl group of this kind formed from $R^4$ and $R^5$ together, wherein two heteroatoms in the cyclic group selected from among oxygen and nitrogen are separated from one another by precisely one optionally substituted —$CH_2$ group, and/or wherein one or both methylene groups of the cyclic group, which are directly attached to the carbon atom to which the groups $R^4$ and $R^5$ are bound, are replaced by a heteroatom from the group comprising oxygen, nitrogen and sulphur, and/or wherein a substituent bound to the cyclic group, which is characterised in that a heteroatom selected from among oxygen, nitrogen, sulphur and halogen atom is bound directly to the cyclic group, is separated from another heteroatom selected from among oxygen, nitrogen and sulphur, with the exception of the sulphone group, by precisely one, optionally substituted methylene group, and/or wherein two oxygen atoms are joined together directly, is excluded, $R^9$ denotes a straight-chain or branched $C_{1-6}$-alkyl group, while the hydrogen atoms of the straight-chain or branched $C_{1-6}$-alkyl group may optionally be wholly or partly replaced by fluorine atoms, and which may optionally be substituted by a $C_{3-5}$-cycloalkyl group, a hydroxy, a $C_{1-5}$-alkyloxy group, while the hydrogen atoms of the $C_{1-5}$-alkyloxy group may optionally be wholly or partly replaced by fluorine atoms, an allyloxy, propargyloxy, benzyloxy, $C_{1-5}$-alkylcarbonyloxy, $C_{1-5}$-alkyloxycarbonyloxy, carboxy-$C_{1-5}$-alkyloxy, $C_{1-5}$-alkyloxycarbonyl-$C_{1-5}$-alkyloxy, carboxy, $C_{1-5}$-alkyloxycarbonyl, aminocarbonyl, $C_{1-5}$-alkylaminocarbonyl, di-($C_{1-5}$-alkyl)-aminocarbonyl, $C_{3-6}$-cycloalkyleneiminocarbonyl, amino, $C_{1-5}$-alkylamino, di-($C_{1-5}$-alkyl)-amino, $C_{1-5}$-alkylcarbonylamino, $C_{1-5}$-alkyl-sulphonylamino, N-($C_{1-5}$-alkylsulphonyl)-$C_{1-5}$-alkylamino or $C_{3-6}$-cycloalkylcarbonylamino group, while the 6- to 7-membered cyclic groups of the $C_{3-6}$-cycloalkyleneiminocarbonyl group in the cyclic moiety a methylene group in the 4 position of a 6- or 7-membered cycloalkyleneimino group may be replaced by an oxygen or sulphur atom, by a carbonyl, sulphinyl, sulphonyl or —$NR^{8c}$ group and additionally a methylene group adjacent to an above-mentioned —$NR^{8c}$ group may be replaced by a carbonyl group, with the proviso that the replacement of hydrogen atoms of the first carbon atom of the straight-chain or branched $C_{1-6}$-alkyl group by substituents from the group comprising oxygen, sulphur or nitrogen is excluded, a phenyl, heteroaryl, phenyl-$C_{1-5}$-alkyl or heteroaryl-$C_{1-5}$-alkyl group, which may optionally be mono- to trisubstituted in the phenyl or heteroaryl moiety by identical or different substituents selected from among halogen atoms, $C_{1-5}$-alkyl, di-($C_{1-5}$-alkyl)-amino, hydroxy, $C_{1-5}$-alkyloxy, mono-, di- or trifluoromethoxy, carboxy- and $C_{1-5}$-alkyloxycarbonyl groups, a 3- to 7-membered cycloalkyl, cycloalkyl-$C_{1-5}$-alkyl or cycloalkyleneimino-$C_{2-3}$-alkyl group, wherein in 4- to 7-membered cyclic groups in the cyclic moiety a methylene group may optionally be replaced by an —$N(R^{8c})$ group, an oxygen or sulphur atom or a —$S(O)$ or —$S(O)_2$ group, or wherein in 4- to 7-membered cyclic groups in the cyclic moiety two adjacent methylene groups together may optionally be replaced by a —$C(O)N(R^{8b})$ or —$S(O)_2N(R^{8b})$ group, or wherein in 6- to 7-membered cyclic groups in the cyclic moiety three adjacent methylene groups together may optionally be replaced by a substituted —$OC(O)N(R^{8b})$ or —$N(R^{8b})C(O)N(R^{8b})$ or —$N(R^{8b})S(O)_2N(R^{8b})$ group, with the proviso that a 3- to 7-membered cycloalkyl, cycloalkyl-$C_{1-5}$-alkyl or cycloalkyleneimino-$C_{2-3}$-alkyl group as hereinbefore defined wherein two heteroatoms from the group comprising oxygen and nitrogen are separated from one another by precisely one optionally substituted —$CH_2$ group, is excluded, while a 3- to 7-membered cycloalkyl, cycloalkyl-$C_{1-5}$-alkyl or cycloalkyleneimino-$C_{2-3}$-alkyl group as hereinbefore defined may be substituted at one or two —$CH_2$ groups by one or two $C_{1-3}$-alkyl groups in each case, B denotes a group of the formula

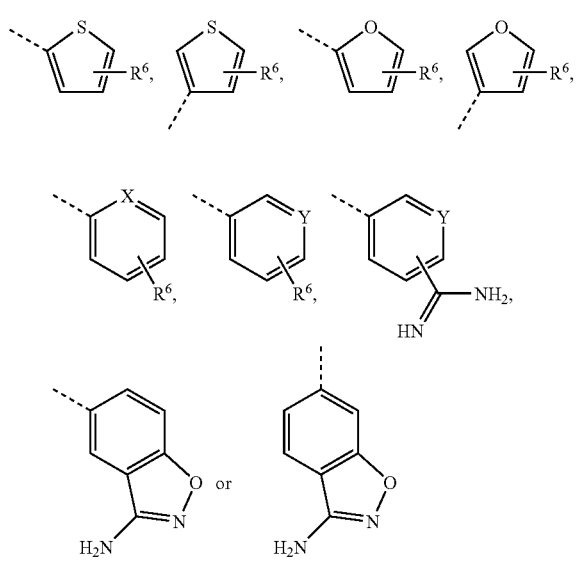

Y denotes a nitrogen atom or a CH group, $R^6$ denotes a hydrogen, a halogen atom, a nitrile group, a $C_{2-3}$-alkenyl, $C_{2-3}$-alkynyl, a $C_{1-3}$-alkyl group, or a $C_{1-3}$-alkoxy group, while the hydrogen atoms of the $C_{1-3}$-alkyl or $C_{1-3}$-alkoxy group may optionally be wholly or partly replaced by fluorine atoms, while, unless otherwise stated, by the term "heteroaryl group" mentioned hereinbefore in the definitions is meant a monocyclic 5- or 6-membered heteroaryl group, while the 6-membered heteroaryl group contains one, two or three nitrogen atoms and the 5-membered heteroaryl group contains an imino group optionally substituted by a $C_{1-3}$-alkyl, phenyl or phenyl-$C_{1-3}$-alkyl group, or an oxygen or sulphur atom or an imino group optionally substituted by a $C_{1-3}$-alkyl, phenyl, amino-$C_{2-3}$-alkyl, $C_{1-3}$-alkylamino-$C_{2-3}$-alkyl, di-($C_{1-3}$-alkyl)-amino-$C_{2-3}$-alkyl, a $C_{3-6}$-cycloalkyleneimino-$C_{1-3}$-alkyl or phenyl-$C_{1-3}$-alkyl group, or an oxygen or sulphur atom and additionally a nitrogen atom or an imino group optionally substituted by a $C_{1-3}$-alkyl or phenyl-$C_{1-3}$-alkyl group and two or three nitrogen atoms, and moreover a phenyl ring optionally substituted by a fluorine, chlorine or bromine atom, a $C_{1-3}$-alkyl, hydroxy, $C_{1-3}$-alkyloxy group, amino, $C_{1-3}$-alkylamino, di-($C_{1-3}$-alkyl)-amino or $C_{3-6}$-cycloalkyleneimino group may be fused to the above-mentioned monocyclic heteroaryl groups via two adjacent carbon atoms and the bond is effected via a nitrogen atom or a carbon atom of the heterocyclic moiety or a fused-on phenyl ring, while, unless otherwise stated, by the term "halogen atom" mentioned hereinbefore in the definitions is meant an atom selected from among fluorine, chlorine, bromine and iodine, while the alkyl, alkenyl, alkynyl and alkoxy groups contained in the above-mentioned definitions which have more than two carbon atoms, unless otherwise stated, may be straight-chain or branched and the alkyl groups in the previously mentioned dialkylated groups, for example the dialkylamino groups, may be identical or different, and the hydrogen atoms of the methyl or ethyl groups contained in the foregoing definitions, unless otherwise stated, may be wholly or partly replaced by fluorine atoms, or a tautomer or salt thereof.

3. A compound of the formula I according to claim 1, wherein,

A denotes a group of the formula

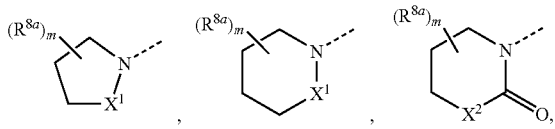

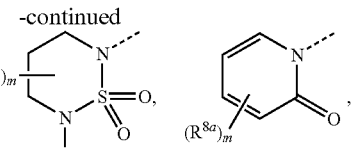

-continued

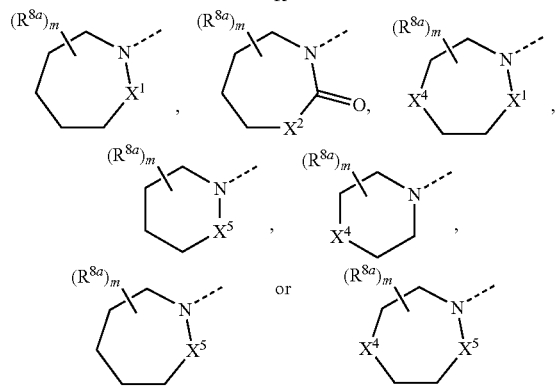

wherein m is the number 1 or 2, $R^{8a}$ each independently of one another denote a hydrogen or fluorine atom or a $C_{1-3}$-alkyl, hydroxy, hydroxy-$C_{1-3}$-alkyl, $C_{1-3}$-alkoxy, $C_{1-3}$-alkoxy-$C_{1-3}$-alkyl, amino, $C_{1-3}$-alkylamino, di-($C_{1-3}$-alkyl)-amino, amino-$C_{1-3}$-alkyl, $C_{1-3}$-alkylamino-$C_{1-3}$-alkyl, or di-($C_{1-3}$-alkyl)-amino-$C_{1-3}$-alkyl group, while in the previously mentioned substituted 5- to 7-membered groups A the heteroatoms F, O or N optionally introduced with $R^{8a}$ as substituents are not separated by precisely one carbon atom from a heteroatom selected from among N, O and S, $R^{8b}$ each independently of one another denote a hydrogen atom or a $C_{1-3}$-alkyl group, $R^{8c}$ each independently of one another denote a hydrogen atom, a $C_{1-3}$-alkyl, $C_{1-3}$-alkylcarbonyl, $C_{1-3}$-alkyloxycarbonyl or $C_{1-3}$-alkylsulphonyl group, $X^1$ denotes a carbonyl, thiocarbonyl, C=$NR^{8c}$, C=N—$OR^{8c}$, C=N—$NO_2$, C=N—CN or sulphonyl group, $X^2$ denotes an oxygen atom or an —$NR^{8b}$ group, $X^3$ denotes a carbonyl, thiocarbonyl, C=$NR^{8c}$, C=N—$OR^{8c}$, C=N—$NO_2$, C=N—CN or sulphonyl group, $X^4$ denotes an oxygen or sulphur atom or an —$NR^{8c}$ group, $X^5$ denotes an oxygen atom or a —$CH_2$, —$CHR^{8a}$ or —$NR^{8c}$ group, $R^1$ denotes a hydrogen or halogen atom, a $C_{1-3}$-alkyl or $C_{1-3}$-alkoxy group, while the hydrogen atoms of the $C_{1-3}$-alkyl or $C_{1-3}$-alkoxy group may optionally be wholly or partly replaced by fluorine atoms, a $C_{2-3}$-alkenyl, $C_{2-3}$-alkynyl, nitrile, nitro or amino group, $R^2$ denotes a hydrogen or halogen atom or a methyl group, X denotes a nitrogen atom or a CH group, $R^3$ denotes a hydrogen atom or a $C_{1-3}$-alkyl group, $R^4$ and $R^5$ each independently of one another denote a hydrogen atom, a hydroxy group, a $OR^9$ group, a $C_{2-6}$-alkenyl or $C_{2-6}$-alkynyl group, a straight-chain or branched $C_{1-6}$-alkyl group, while the hydrogen atoms of the straight-chain or branched $C_{1-6}$-alkyl group may optionally be wholly or partly replaced by fluorine atoms, and which may optionally be substituted by a $C_{3-5}$-cycloalkyl group, a nitrile, hydroxy, a $C_{1-5}$-alkyloxy group, while the hydrogen atoms of the $C_{1-5}$-alkyloxy group may optionally be wholly or partly replaced by fluorine atoms, an allyloxy, propargyloxy, benzyloxy, $C_{1-5}$-alkylcarbonyloxy, $C_{1-5}$-alkyloxycarbonyloxy, carboxy-$C_{1-5}$-alkyloxy, $C_{1-5}$-alkyloxycarbonyl-$C_{1-5}$-alkyloxy, mercapto, $C_{1-5}$-alkylsulphanyl, $C_{1-5}$-alkylsulphonyl, carboxy, $C_{1-5}$-alkyloxycarbonyl, aminocarbonyl, $C_{1-5}$-alkylaminocarbonyl, di-($C_{1-5}$-alkyl)-aminocarbonyl, $C_{3-6}$-cycloalkyleneiminocarbonyl, aminosulphonyl, $C_{1-5}$-alkylaminosulphonyl, di-($C_{1-5}$-alkyl)-aminosulphonyl, $C_{3-6}$-cycloalkyleneiminosulphonyl, amino, $C_{1-5}$-alkylamino, di-($C_{1-5}$-alkyl)-amino, $C_{1-5}$-alkylcarbonylamino, $C_{1-5}$-alkyl-sulphonylamino, N-($C_{1-5}$-alkylsulphonyl)-$C_{1-5}$-alkylamino or $C_{3-6}$-cycloalkylcarbonylamino group, while the 6- to 7-membered cyclic groups of the $C_{3-6}$-cycloalkyleneiminocarbonyl group in the cyclic moiety a methylene group in the 4 position of a 6- or 7-membered cycloalkyleneimino group may be replaced by an oxygen or sulphur atom, by a carbonyl, sulphinyl, sulphonyl or —NR$^{8c}$ group and additionally a methylene group adjacent to an above-mentioned —NR$^{8c}$ group may be replaced by a carbonyl group, a phenyl, heteroaryl, phenyl-$C_{1-5}$-alkyl or heteroaryl-$C_{1-5}$-alkyl group,
which may optionally be mono- to trisubstituted in the phenyl or heteroaryl moiety by identical or different substituents selected from among halogen atoms, $C_{1-5}$-alkyl, di-($C_{1-5}$-alkyl)-amino, hydroxy, $C_{1-5}$-alkyloxy, mono-, di- or trifluoromethoxy, carboxy- and $C_{1-5}$-alkyloxycarbonyl groups, a 3- to 7-membered cycloalkyl, cycloalkyleneimino, cycloalkyl-$C_{1-5}$-alkyl or cycloalkyleneimino-$C_{1-3}$-alkyl group,
wherein in 4- to 7-membered cyclic groups in the cyclic moiety a methylene group may optionally be replaced by an —N(R$^{8c}$) group, an oxygen or sulphur atom or a —S(O) or —S(O)$_2$ group, or
wherein in 4- to 7-membered cyclic groups in the cyclic moiety two adjacent methylene groups together may optionally be replaced by a —C(O)N(R$^{8b}$) or —S(O)$_2$N(R$^{8b}$) group, or
wherein in 6- to 7-membered cyclic groups in the cyclic moiety three adjacent methylene groups together may optionally be replaced by a substituted —OC(O)N(R$^{8b}$) or —N(R$^{8b}$)C(O)N(R$^{8b}$) or —N(R$^{8b}$)S(O)$_2$N(R$^{8b}$) group, with the proviso that a 3- to 7-membered cycloalkyl, cycloalkyleneimino, cycloalkyl-$C_{1-5}$-alkyl or cycloalkyleneimino-$C_{1-3}$-alkyl group as hereinbefore defined wherein two heteroatoms from the group comprising oxygen and nitrogen are separated from one another by precisely one optionally substituted —CH$_2$ group, is excluded, while a 3- to 7-membered cycloalkyl, cycloalkyleneimino, cycloalkyl-$C_{1-5}$-alkyl or cycloalkyleneimino-$C_{1-3}$-alkyl group as hereinbefore defined may be substituted at one or two —CH$_2$ groups by one or two $C_{1-3}$-alkyl groups in each case, with the proviso that R$^4$ and R$^5$ cannot simultaneously be defined as hydroxy or OR$^9$ groups, R$^9$ denotes a straight-chain or branched $C_{1-6}$-alkyl group, while the hydrogen atoms of the straight-chain or branched $C_{1-6}$-alkyl group may optionally be wholly or partly replaced by fluorine atoms, and which may optionally be substituted by a $C_{3-5}$-cycloalkyl group, a hydroxy, a $C_{1-5}$-alkyloxy group, while the hydrogen atoms of the $C_{1-5}$-alkyloxy group may optionally be wholly or partly replaced by fluorine atoms, an allyloxy, propargyloxy, benzyloxy, $C_{1-5}$-alkylcarbonyloxy, $C_{1-5}$-alkyloxycarbonyloxy, carboxy-$C_{1-5}$-alkyloxy, $C_{1-5}$-alkyloxycarbonyl-$C_{1-5}$-alkyloxy, carboxy, $C_{1-5}$-alkyloxycarbonyl, aminocarbonyl, $C_{1-5}$-alkylaminocarbonyl, di-($C_{1-5}$-alkyl)-aminocarbonyl, $C_{3-6}$-cycloalkyleneiminocarbonyl, amino, $C_{1-5}$-alkylamino, di-($C_{1-5}$-alkyl)-amino, $C_{1-5}$-alkylcarbonylamino, $C_{1-5}$-alkylsulphonylamino, N-($C_{1-5}$-alkylsulphonyl)-$C_{1-5}$-alkylamino or $C_{3-6}$-cycloalkylcarbonylamino group, while the 6- to 7-membered cyclic groups of the $C_{3-6}$-cycloalkyleneiminocarbonyl group in the cyclic moiety a methylene group in the 4 position of a 6- or 7-membered cycloalkyleneimino group by an oxygen or sulphur atom may be replaced by a carbonyl, sulphinyl, sulphonyl or —NR$^{8c}$ group and additionally a methylene group adjacent to an above-mentioned —NR$^{8c}$ group may be replaced by a carbonyl group, with the proviso that the replacement of hydrogen atoms of the first carbon atom of the straight-chain or branched $C_{1-6}$-alkyl group by substituents from the group comprising oxygen, sulphur or nitrogen is excluded, a phenyl or heteroaryl group
which may optionally be mono- to trisubstituted in the phenyl or heteroaryl moiety by identical or different substituents selected from among halogen atoms, $C_{1-5}$-alkyl, di-($C_{1-5}$-alkyl)-amino, hydroxy, $C_{1-5}$-alkyloxy, mono-, di- or trifluoromethoxy, carboxy- and $C_{1-5}$-alkyloxycarbonyl groups, a phenyl-$C_{1-5}$-alkyl or heteroaryl-$C_{1-5}$-alkyl group,
which may optionally be mono- to trisubstituted in the phenyl or heteroaryl moiety by identical or different substituents selected from among halogen atoms, $C_{1-5}$-alkyl, di-($C_{1-5}$-alkyl)-amino, hydroxy, $C_{1-5}$-alkyloxy, mono-, di- or trifluoromethoxy, carboxy- and $C_{1-5}$-alkyloxycarbonyl groups, and which may optionally be substituted in the $C_{1-5}$-alkyl-moiety by a hydroxy, a $C_{1-5}$-alkyloxy group, while the hydrogen atoms of the $C_{1-5}$-alkyloxy group may optionally be wholly or partly replaced by fluorine atoms, an allyloxy, propargyloxy, benzyloxy, $C_{1-5}$-alkylcarbonyloxy, $C_{1-5}$-alkyloxycarbonyloxy, carboxy-$C_{1-5}$-alkyloxy, or a $C_{1-5}$-alkyloxycarbonyl-$C_{1-5}$-alkyloxy group;

a 3- to 7-membered cycloalkyl, cycloalkyl-$C_{1-5}$-alkyl or cycloalkyleneimino-$C_{2-3}$-alkyl group,
wherein in 4- to 7-membered cyclic groups in the cyclic moiety a methylene group may optionally be replaced by an —N(R$^{8c}$) group, an oxygen or sulphur atom or a —S(O) or —S(O)$_2$ group, or
wherein in 4- to 7-membered cyclic groups in the cyclic moiety two adjacent methylene groups together may optionally be replaced by a —C(O)N(R$^{8b}$) or —S(O)$_2$N(R$^{8b}$) group, or
wherein in 6- to 7-membered cyclic groups in the cyclic moiety three adjacent methylene groups together may optionally be replaced by a substituted —OC(O)N(R$^{8b}$) or —N(R$^{8b}$)C(O)N(R$^{8b}$) or —N(R$^{8b}$)S(O)$_2$N(R$^{8b}$) group, with the proviso that a 3- to 7-membered cycloalkyl, cycloalkyl-$C_{1-5}$-alkyl or cycloalkyleneimino-$C_{2-3}$-alkyl group as hereinbefore defined wherein two heteroatoms from the group comprising oxygen and nitrogen are separated from one another by precisely one optionally substituted —$CH_2$ group, is excluded, while a 3- to 7-membered cycloalkyl, cycloalkyl-$C_{1-5}$-alkyl or cycloalkyleneimino-$C_{2-3}$-alkyl group as hereinbefore defined may be substituted at one or two —$CH_2$ groups by one or two $C_{1-3}$-alkyl groups in each case, B denotes a group of the formula

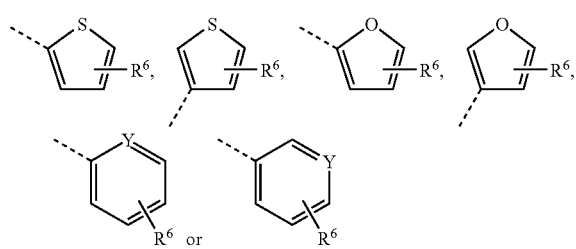

Y denotes a nitrogen atom or a CH group, $R^6$ denotes a hydrogen, a halogen atom, an ethynyl, a methyl group, a methoxy group, while the hydrogen atoms of the methoxy group may optionally be wholly or partly replaced by fluorine atoms, while, unless otherwise stated, by the term "heteroaryl group" mentioned hereinbefore in the definitions is meant a monocyclic 5- or 6-membered heteroaryl group, while the 6-membered heteroaryl group contains one, two or three nitrogen atoms and the 5-membered heteroaryl group contains an imino group optionally substituted by a $C_{1-3}$-alkyl, phenyl or phenyl-$C_{1-3}$-alkyl group, an oxygen or sulphur atom or an imino group optionally substituted by a $C_{1-3}$-alkyl, phenyl, amino-$C_{2-3}$-alkyl, $C_{1-3}$-alkylamino-$C_{2-3}$-alkyl, di-($C_{1-3}$-alkyl)-amino-$C_{2-3}$-alkyl, a $C_{3-6}$-cycloalkyleneimino-$C_{1-3}$-alkyl or phenyl-$C_{1-3}$-alkyl group or an oxygen or sulphur atom and additionally a nitrogen atom or an imino group optionally substituted by a $C_{1-3}$-alkyl or phenyl-$C_{1-3}$-alkyl group and two or three nitrogen atoms, and moreover a phenyl ring optionally substituted by a fluorine, chlorine or bromine atom, a $C_{1-3}$-alkyl, hydroxy, $C_{1-3}$-alkyloxy group, amino, $C_{1-3}$-alkylamino, di-($C_{1-3}$-alkyl)-amino or $C_{3-6}$-cycloalkyleneimino group may be fused to the above-mentioned monocyclic heteroaryl groups via two adjacent carbon atoms and the bond is effected via a nitrogen atom or a carbon atom of the heterocyclic moiety or a fused-on phenyl ring, while, unless otherwise stated, by the term "halogen atom" mentioned hereinbefore in the definitions is meant an atom selected from among fluorine, chlorine, bromine and iodine, while the alkyl, alkenyl, alkynyl and alkoxy groups contained in the above-mentioned definitions which have more than two carbon atoms, unless otherwise stated, may be straight-chain or branched and the alkyl groups in the previously mentioned dialkylated groups, for example the dialkylamino groups, may be identical or different, and the hydrogen atoms of the methyl or ethyl groups contained in the foregoing definitions, unless otherwise stated, may be wholly or partly replaced by fluorine atoms, or a tautomer or salt thereof.

4. A compound of the formula I according to claim 1, wherein,

A denotes a group of the formula

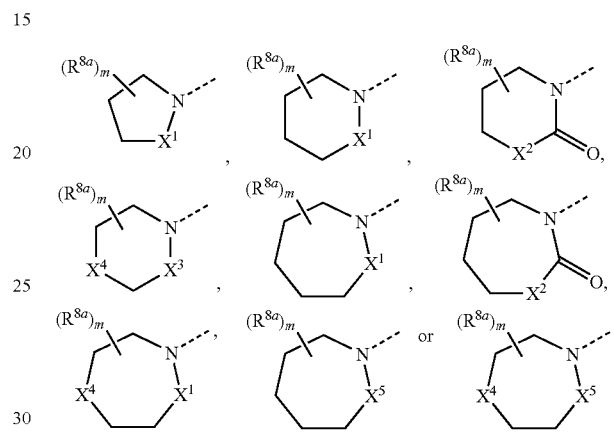

wherein m is the number 1 or 2, $R^{8a}$ each independently of one another denote a hydrogen or fluorine atom or a $C_{1-3}$-alkyl, hydroxy, hydroxy-$C_{1-3}$-alkyl, $C_{1-3}$-alkoxy, $C_{1-3}$-alkoxy-$C_{1-3}$-alkyl, amino, $C_{1-3}$-alkylamino, di-($C_{1-3}$-alkyl)-amino, amino-$C_{1-3}$-alkyl, $C_{1-3}$-alkylamino-$C_{1-3}$-alkyl, or di-($C_{1-3}$-alkyl)-amino-$C_{1-3}$-alkyl group, while in the previously mentioned substituted 5- to 7-membered groups A the heteroatoms F, O or N optionally introduced with $R^{8a}$ as substituents are not separated by precisely one carbon atom from a heteroatom selected from among N, O and S, $R^{8b}$ each independently of one another denote a hydrogen atom or a $C_{1-3}$-alkyl group, $R^{8c}$ each independently of one another denote a hydrogen atom, a $C_{1-3}$-alkyl, $C_{1-3}$-alkylcarbonyl, $C_{1-3}$-alkyloxycarbonyl or $C_{1-3}$-alkylsulphonyl group, $X^1$ denotes a carbonyl, or sulphonyl group, $X^2$ denotes an oxygen atom or an —$NR^{8b}$ group, $X^3$ denotes a carbonyl, thiocarbonyl, C=$NR^{8c}$, C=N—$OR^{8c}$, C=N—$NO_2$, C=N—CN or sulphonyl group, $X^4$ denotes an oxygen or sulphur atom or an —$NR^{8c}$ group, $X^5$ denotes an oxygen atom or a —$CH_2$, —$CHR^{8a}$ or —$NR^{8c}$ group, $R^1$ denotes a hydrogen or halogen atom, a $C_{1-3}$-alkyl or $C_{1-3}$-alkoxy group, while the hydrogen atoms of the $C_{1-3}$-alkyl or $C_{1-3}$-alkoxy group may optionally be wholly or partly replaced by fluorine atoms, a $C_{2-3}$-alkenyl, $C_{2-3}$-alkynyl, nitrile, nitro or amino group, $R^2$ denotes a hydrogen or fluorine atom or a methyl group, X denotes a nitrogen atom or a CH group, $R^3$ denotes a hydrogen atom or a $C_{1-3}$-alkyl group, $R^4$ denotes a hydrogen atom, a straight-chain or branched $C_{1-4}$-alkyl group, while the hydrogen atoms of the straight-chain or branched $C_{1-4}$-alkyl group may optionally be wholly or partly replaced by fluorine atoms, and which may optionally be substituted by a $C_{1-3}$-alkyloxy group, while the hydrogen atoms of the $C_{1-3}$-alkyloxy group may optionally be wholly or partly replaced by fluorine atoms, $R^5$ denotes a hydrogen atom, a hydroxy group, a $OR^9$ group, a $C_{2-4}$-alkenyl or $C_{2-4}$-alkynyl group, a straight-chain or branched $C_{1-4}$-alkyl group, while the hydrogen atoms of the straight-chain or branched $C_{1-4}$-alkyl group may optionally be wholly or partly replaced by fluorine atoms, and which may optionally be substituted by a $C_{3-5}$-cycloalkyl group, a nitrile, hydroxy, a $C_{1-5}$-alkyloxy group, while the hydrogen atoms of the $C_{1-5}$-alkyloxy group may optionally be wholly or partly replaced by fluorine atoms, an allyloxy, propargyloxy, benzyloxy, $C_{1-5}$-alkylcarbonyloxy, $C_{1-5}$-alkyloxycarbonyloxy, carboxy-$C_{1-5}$-alkyloxy, $C_{1-5}$-alkyloxycarbonyl-$C_{1-5}$-alkyloxy, mercapto, $C_{1-5}$-alkylsulphanyl, $C_{1-5}$-alkylsulphonyl, carboxy, $C_{1-5}$-alkyloxycarbonyl, aminocarbonyl, $C_{1-5}$-alkylaminocarbonyl, di-($C_{1-5}$-alkyl)-aminocarbonyl, $C_{3-6}$-cycloalkyleneiminocarbonyl, aminosulphonyl, $C_{1-5}$-alkylaminosulphonyl, di-($C_{1-5}$-alkyl)-aminosulphonyl, $C_{3-6}$-cycloalkyleneiminosulphonyl, amino, $C_{1-5}$-alkylamino, di-($C_{1-5}$-alkyl)-amino, $C_{1-5}$-alkylcarbonylamino, $C_{1-5}$-alkyl-sulphonylamino, N-($C_{1-5}$-alkylsulphonyl)-$C_{1-5}$-alkylamino or $C_{3-6}$-cycloalkylcarbonylamino group, while the 6- to 7-membered cyclic groups of the $C_{3-6}$-cycloalkyleneiminocarbonyl group in the cyclic moiety a methylene group in the 4 position of a 6- or 7-membered cycloalkyleneimino group may be replaced by an oxygen or sulphur atom, by a carbonyl, sulphinyl, sulphonyl or —$NR^{8c}$ group and additionally a methylene group adjacent to an above-mentioned —$NR^{8c}$ group may be replaced by a carbonyl group, a phenyl, heteroaryl, phenyl-$C_{1-5}$-alkyl or heteroaryl-$C_{1-5}$-alkyl group, which may optionally be mono- to trisubstituted in the phenyl or heteroaryl moiety may be substituted by identical or different substituents selected from among halogen atoms, $C_{1-5}$-alkyl, di-($C_{1-5}$-alkyl)-amino, hydroxy, $C_{1-5}$-alkyloxy, mono-, di- or trifluoromethoxy, carboxy- and $C_{1-5}$-alkyloxycarbonyl groups, $R^9$ denotes a straight-chain or branched $C_{1-4}$-alkyl group, while the hydrogen atoms of the straight-chain or branched $C_{1-4}$-alkyl group may optionally be wholly or partly replaced by fluorine atoms, and which may optionally be substituted by a $C_{3-5}$-cycloalkyl group, a hydroxy, a $C_{1-5}$-alkyloxy group, while the hydrogen atoms of the $C_{1-5}$-alkyloxy group may optionally be wholly or partly replaced by fluorine atoms, an allyloxy, propargyloxy, benzyloxy, $C_{1-5}$-alkylcarbonyloxy, $C_{1-5}$-alkyloxycarbonyloxy, carboxy-$C_{1-5}$-alkyloxy, $C_{1-5}$-alkyloxycarbonyl-$C_{1-5}$-alkyloxy, carboxy, $C_{1-5}$-alkyloxycarbonyl, aminocarbonyl, $C_{1-5}$-alkylaminocarbonyl, di-($C_{1-5}$-alkyl)-aminocarbonyl, $C_{3-6}$-cycloalkyleneiminocarbonyl, amino, $C_{1-5}$-alkylamino, di-($C_{1-5}$-alkyl)-amino, $C_{1-5}$-alkylcarbonylamino, $C_{1-5}$-alkylsulphonylamino, N-($C_{1-5}$-alkylsulphonyl)-$C_{1-5}$-alkylamino or $C_{3-6}$-cycloalkylcarbonylamino group, while the 6- to 7-membered cyclic groups of the $C_{3-6}$-cycloalkyleneiminocarbonyl group in the cyclic moiety a methylene group in the 4 position of a 6- or 7-membered cycloalkyleneimino group may be replaced by an oxygen or sulphur atom, by a carbonyl, sulphinyl, sulphonyl or —$NR^{8c}$ group and additionally a methylene group adjacent to an above-mentioned —$NR^{8c}$ group may be replaced by a carbonyl group, with the proviso that the replacement of hydrogen atoms of the first carbon atom of the straight-chain or branched $C_{1-4}$-alkyl group by substituents from the group comprising oxygen, sulphur or nitrogen is excluded, a phenyl or heteroaryl group which may optionally be mono- to trisubstituted in the phenyl or heteroaryl moiety by identical or different substituents selected from among halogen atoms, $C_{1-5}$-alkyl, di-($C_{1-5}$-alkyl)-amino, hydroxy, $C_{1-5}$-alkyloxy, mono-, di- or trifluoromethoxy, carboxy- and $C_{1-5}$-alkyloxycarbonyl groups, a phenyl-$C_{1-5}$-alkyl or heteroaryl-$C_{1-5}$-alkyl group, which may optionally be mono- to trisubstituted in the phenyl or heteroaryl moiety by identical or different substituents selected from among halogen atoms, $C_{1-5}$-alkyl, di-($C_{1-5}$-alkyl)-amino, hydroxy, $C_{1-5}$-alkyloxy, mono-, di- or trifluoromethoxy, carboxy- and $C_{1-5}$-alkyloxycarbonyl groups, and which may optionally be substituted in the $C_{1-5}$-alkyl-moiety by a hydroxy, a $C_{1-5}$-alkyloxy group, while the hydrogen atoms of the $C_{1-5}$-alkyloxy group may optionally be wholly or partly replaced by fluorine atoms, an allyloxy, propargyloxy, benzyloxy, $C_{1-5}$-alkylcarbonyloxy, $C_{1-5}$-alkyloxycarbonyloxy, carboxy-$C_{1-5}$-alkyloxy, or a $C_{1-5}$-alkyloxycarbonyl-$C_{1-5}$-alkyloxy group;

B denotes a group of the formula

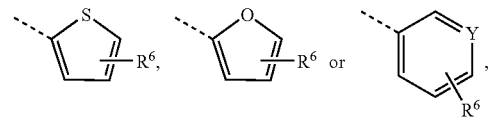

Y denotes a nitrogen atom or a CH group, $R^6$ denotes a hydrogen, a halogen atom, an ethynyl, a methyl group, a methoxy group, while the hydrogen atoms of the methoxy group may optionally be wholly or partly replaced by fluorine atoms, while, unless otherwise stated, by the term "heteroaryl group" mentioned hereinbefore in the definitions is meant a monocyclic 5- or 6-membered heteroaryl group, while the 6-membered heteroaryl group contains one, two or three nitrogen atoms and the 5-membered heteroaryl group contains an imino group optionally substituted by a $C_{1-3}$-alkyl, phenyl or phenyl-$C_{1-3}$-alkyl group, or an oxygen or sulphur atom or an imino group optionally substituted by a $C_{1-3}$-alkyl, phenyl, amino-$C_{2-3}$-alkyl, $C_{1-3}$-alkylamino-$C_{2-3}$- alkyl, di-($C_{1-3}$-alkyl)-amino-$C_{2-3}$-alkyl, a $C_{3-6}$-cycloalkyleneimino-$C_{1-3}$-alkyl or phenyl-$C_{1-3}$-alkyl group, or an oxygen or sulphur atom and additionally a nitrogen atom or an imino group optionally substituted by a $C_{1-3}$-alkyl or phenyl-$C_{1-3}$-alkyl group and two or three nitrogen atoms, and moreover a phenyl ring optionally substituted by a fluorine, chlorine or bromine atom, a $C_{1-3}$-alkyl, hydroxy, $C_{1-3}$-alkyloxy group, amino, $C_{1-3}$-alkylamino, di-($C_{1-3}$-alkyl)-amino or $C_{3-6}$-cycloalkyleneimino group may be fused to the above-mentioned monocyclic heteroaryl groups via two adjacent carbon atoms and the bond is effected via a nitrogen atom or a carbon atom of the heterocyclic moiety or a fused-on phenyl ring, while, unless otherwise stated, by the term "halogen atom" mentioned hereinbefore in the definitions is meant an atom selected from among fluorine, chlorine, bromine and iodine, while the alkyl, alkenyl, alkynyl and alkoxy groups contained in the above-mentioned definitions which have more than two carbon atoms, unless otherwise stated, may be straight-chain or branched and the alkyl groups in the previously mentioned dialkylated groups, for example the dialkylamino groups, may be identical or different, and the hydrogen atoms of the methyl or ethyl groups contained in the foregoing definitions, unless otherwise stated, may be wholly or partly replaced by fluorine atoms, or a tautomer or salt thereof.

5. A compound of the formula I according to claim 1, wherein,

A denotes a group of the formula

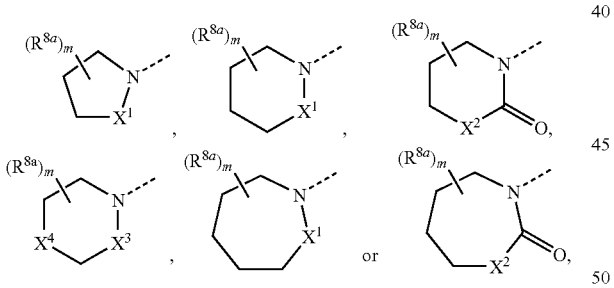

wherein m is the number 1 or 2, $R^{8a}$ each independently of one another denote a hydrogen or fluorine atom or a $C_{1-3}$-alkyl, hydroxy, hydroxy-$C_{1-3}$-alkyl, $C_{1-3}$-alkoxy, $C_{1-3}$-alkoxy-$C_{1-3}$-alkyl, amino, $C_{1-3}$-alkylamino, di-($C_{1-3}$-alkyl)-amino, amino-$C_{1-3}$-alkyl, $C_{1-3}$-alkylamino-$C_{1-3}$-alkyl, or di-($C_{1-3}$-alkyl)-amino-$C_{1-3}$-alkyl group, while in the previously mentioned substituted 5- to 7-membered groups A the heteroatoms F, O or N optionally introduced with $R^{8a}$ as substituents are not separated by precisely one carbon atom from a heteroatom selected from among N, O and S, $R^{8b}$ each independently of one another denote a hydrogen atom or a $C_{1-3}$-alkyl group, $R^{8c}$ each independently of one another denote a hydrogen atom, a $C_{1-3}$-alkyl, $C_{1-3}$-alkylcarbonyl, $C_{1-3}$-alkyloxycarbonyl or $C_{1-3}$-alkylsulphonyl group, $X^1$ denotes a carbonyl or sulphonyl group, $X^2$ denotes an oxygen atom or an —$NR^{8b}$ group, $X^3$ denotes a carbonyl, thiocarbonyl, C=$NR^{8c}$, C=N—$OR^{8c}$, C=N—$NO_2$, C=N—CN or sulphonyl group, $X^4$ denotes an oxygen or sulphur atom or an —$NR^{8c}$ group, $R^1$ denotes a hydrogen, fluorine, chlorine or bromine atom, a methyl or methoxy group, while the hydrogen atoms of the methyl or methoxy group may optionally be wholly or partly replaced by fluorine atoms, $R^2$ denotes a hydrogen or fluorine atom, X denotes a nitrogen atom or a CH group, $R^3$ denotes a hydrogen atom or a $C_{1-3}$-alkyl group, $R^4$ denotes a hydrogen atom, $R^5$ denotes a hydrogen atom, a hydroxy group, a $OR^9$ group, a $C_{2-4}$-alkenyl or $C_{2-4}$-alkynyl group, a straight-chain or branched $C_{1-4}$-alkyl group, while the hydrogen atoms may optionally be wholly or partly replaced by fluorine atoms, and which may optionally be substituted by a hydroxy, a $C_{1-3}$-alkyloxy group, while the hydrogen atoms of the $C_{1-3}$-alkyloxy group may be wholly or partly replaced by fluorine atoms, a benzyloxy, $C_{1-3}$-alkylcarbonyloxy, $C_{1-3}$-alkyloxycarbonyl, aminocarbonyl, $C_{1-3}$-alkylaminocarbonyl, di-($C_{1-3}$-alkyl)-aminocarbonyl, $C_{3-6}$-cycloalkyleneiminocarbonyl, amino, $C_{1-3}$-alkylamino, di-($C_{1-3}$-alkyl)-amino, $C_{1-3}$-alkylcarbonylamino, or $C_{1-3}$-alkylsulphonylamino group, a phenyl, or C-linked heteroaryl group, while the heteroaryl group is selected from among pyrrolyl, oxazolyl, imidazolyl, furanyl, thiophenyl, thiazolyl, 1,2,3-triazolyl, 1,2,4-triazolyl, tetrazolyl, pyridinyl, pyrimidinyl and pyrazinyl, and which may optionally be mono- to disubstituted in the heteroaryl moiety by identical or different substituents selected from among halogen atoms, $C_{1-3}$-alkyl, hydroxy, a $C_{1-3}$-alkyloxy, mono-, di- and trifluoromethoxy groups, a phenyl-$C_{1-3}$-alkyl, heteroaryl-$C_{1-3}$-alkyl- group, while the heteroaryl group is selected from among pyrrolyl, oxazolyl, imidazolyl, furanyl, thiophenyl, thiazolyl, 1,2,3-triazolyl, 1,2,4-triazolyl, tetrazolyl, pyridinyl, pyrimidinyl and pyrazinyl, and which may optionally be mono- to disubstituted in the heteroaryl moiety by identical or different substituents selected from among halogen atoms, $C_{1-3}$-alkyl, hydroxy, $C_{1-3}$-alkyloxy, mono-, di- and trifluoromethoxy groups, and which may optionally be substituted in the $C_{1-3}$-alkyl moiety by a hydroxy, a $C_{1-3}$-alkyloxy group, while the hydrogen atoms of the $C_{1-3}$-alkyloxy group may optionally be wholly or partly replaced by fluorine atoms, a $C_{1-5}$-alkylcarbonyloxy, or a $C_{1-5}$-alkyloxycarbonyloxy group;

$R^9$ denotes a straight-chain or branched $C_{1-4}$-alkyl group, while the hydrogen atoms of the straight-chain or branched $C_{1-4}$-alkyl group may optionally be wholly or partly replaced by fluorine atoms, and which may optionally be substituted by a hydroxy, a $C_{1-3}$-alkyloxy group, while the hydrogen atoms of the $C_{1-3}$-alkyloxy group may optionally be wholly or partly replaced by fluorine atoms, a benzyloxy, $C_{1-3}$-alkyloxycarbonyl, aminocarbonyl, $C_{1-3}$-alkylaminocarbonyl, di-($C_{1-3}$-alkyl)-aminocarbonyl, $C_{3-6}$-cycloalkyleneiminocarbonyl, amino, $C_{1-3}$-alkylamino, di-($C_{1-3}$-alkyl)-amino, $C_{1-3}$-alkylcarbonylamino, $C_{1-3}$-alkylsulphonylamino group, with the proviso that the replacement of hydrogen atoms of the first carbon atom of the straight-chain or branched $C_{1-4}$-alkyl group by substituents from the group comprising oxygen, sulphur or nitrogen is excluded, a phenyl, phenyl-$C_{1-2}$-alkyl, heteroaryl-$C_{1-2}$-alkyl or C-linked heteroaryl group while the heteroaryl group is selected from among pyrrolyl, oxazolyl, imidazolyl, furanyl, thiophenyl, thiazolyl, 1,2,3-triazolyl, 1,2,4-triazolyl, tetrazolyl, pyridinyl, pyrimidinyl and pyrazinyl, and which may optionally be mono- to disubstituted in the heteroaryl moiety by identical or different substituents selected from among halogen atoms, $C_{1-3}$-alkyl, hydroxy, $C_{1-3}$-alkyloxy, mono-, di- and trifluoromethoxy groups, B denotes a group of general formula

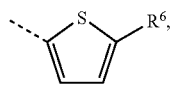

$R^6$ denotes a hydrogen, a chlorine or bromine atom, an ethynyl, a methyl or a methoxy group, while, unless otherwise stated, by the term "halogen atom" mentioned hereinbefore in the definitions is meant an atom selected from among fluorine, chlorine, bromine and iodine, while the alkyl, alkenyl, alkynyl and alkoxy groups contained in the above-mentioned definitions which have more than two carbon atoms, unless otherwise stated, may be straight-chain or branched and the alkyl groups in the previously mentioned dialkylated groups, for example the dialkylamino groups, may be identical or different, and the hydrogen atoms of the methyl or ethyl groups contained in the foregoing definitions, unless otherwise stated, may be wholly or partly replaced by fluorine atoms, or a tautomer or salt thereof.

6. A compound of the formula I according to claim 1, wherein,

A denotes a group of the formula

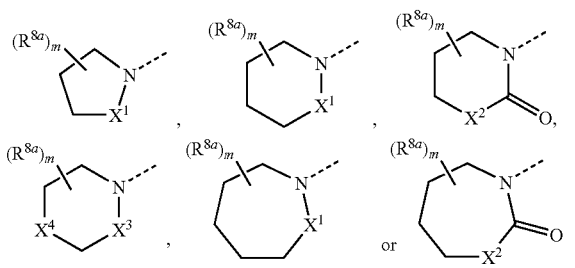

wherein m is the number 1 or 2, $R^{8a}$ each independently of one another denote a hydrogen or fluorine atom or a $C_{1-3}$-alkyl, hydroxy, hydroxy-$C_{1-3}$-alkyl, $C_{1-3}$-alkoxy, $C_{1-3}$-alkoxy-$C_{1-3}$-alkyl, amino, $C_{1-3}$-alkylamino, di-($C_{1-3}$-alkyl)-amino, amino-$C_{1-3}$-alkyl, $C_{1-3}$-alkylamino-$C_{1-3}$-alkyl, or di-($C_{1-3}$-alkyl)-amino-$C_{1-3}$-alkyl group, while in the previously mentioned substituted 5- to 7-membered groups A the heteroatoms F, O or N optionally introduced with $R^{8a}$ as substituents are not separated by precisely one carbon atom from a heteroatom selected from among N, O and S, $R^{8b}$ each independently of one another denote a hydrogen atom or a $C_{1-3}$-alkyl group, $R^{8c}$ each independently of one another denote a hydrogen atom, a $C_{1-3}$-alkyl, $C_{1-3}$-alkylcarbonyl, $C_{1-3}$-alkyloxycarbonyl or $C_{1-3}$-alkylsulphonyl group, $X^1$ denotes a carbonyl or sulphonyl group, $X^2$ denotes an oxygen atom or an —$NR^{8b}$ group, $X^3$ denotes a carbonyl or sulphonyl group, $X^4$ denotes an oxygen atom or an —$NR^{8c}$ group, $R^1$ denotes a hydrogen, fluorine, chlorine or bromine atom, a methyl, trifluoromethyl or methoxy group, $R^2$ denotes a hydrogen atom, X denotes a nitrogen atom or a CH group, $R^3$ denotes a hydrogen atom or a methyl group, $R^4$ denotes a hydrogen atom, $R^5$ denotes a hydrogen atom, a hydroxy group, a $OR^9$ group, an allyl or methallyl group, a methyl group which may optionally be substituted independently of one another by a $C_{1-3}$-alkyl, hydroxy, $OR^9$ group, aminocarbonyl, pyridin-4-yl, pyridin-3-yl, pyridin-2-yl, pyrazin-2-yl, pyrazin-3-yl or phenyl group, a phenyl group, $R^9$ a straight-chain or branched $C_{1-4}$-alkyl group, which may optionally be substituted by a hydroxy, a $C_{1-3}$-alkoxy group, a benzyloxy or a di-($C_{1-3}$-alkyl)-amino group, with the proviso that the replacement of hydrogen atoms of the first carbon atom of the straight-chain or branched $C_{1-4}$-alkyl group by substituents from the group comprising oxygen or nitrogen is excluded, B denotes a group of general formula

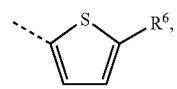

$R^6$ denotes a chlorine or bromine atom or an ethynyl group, while, unless otherwise stated, by the term "halogen atom" mentioned hereinbefore in the definitions is meant an atom selected from among fluorine, chlorine, bromine and iodine, while the alkyl, alkenyl, alkynyl and alkoxy groups contained in the above-mentioned definitions which have more than two carbon atoms, unless otherwise stated, may be straight-chain or branched and the alkyl groups in the previously mentioned dialkylated groups, for example the dialkylamino groups, may be identical or different, and the hydrogen atoms of the methyl or ethyl groups contained in the foregoing definitions, unless otherwise stated, may be wholly or partly replaced by fluorine atoms, or a tautomer or salt thereof.

7. A compound of the formula I according to claim 1 wherein,
the group B denotes the group

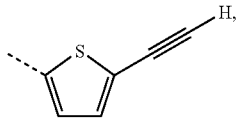

or a tautomer or salt thereof.

8. A compound of the formula I according to claim 1 wherein,
the group B denotes the group

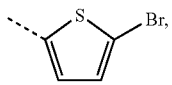

or a tautomer or salt thereof.

9. A compound selected from the group consisting of the following:
(1) 5-bromo-thiophene-2-carboxylic acid-{1-[3-chloro-4-(2-oxo-[1,3]oxazinan-3-yl)-phenyl]-5-oxo-pyrrolidin-3-yl}-amide
(2) 5-chloro-thiophene-2-carboxylic acid-{1-[3-methyl-4-(3-oxo-morpholin-4-yl)-phenyl]-5-oxo-pyrrolidin-3-yl}-amide
(3) 5-chloro-thiophene-2-carboxylic acid-{1-[3-chloro-4-(2-oxo-[1,3]oxazinan-3-yl)-phenyl]-5-oxo-pyrrolidin-3-yl}-amide
(4) (R)-5-bromo-thiophene-2-carboxylic acid-{1-[3-methyl-4-(3-oxo-morpholin-4-yl)-phenyl]-5-oxo-pyrrolidin-3-yl}-amide
(5) (R)-5-bromo-thiophene-2-carboxylic acid-{5-oxo-1-[5-(3-oxo-morpholin-4-yl )-pyridin-2-yl]-pyrrolidin-3-yl}-amide
(6) 5-bromo-thiophene-2-carboxylic acid-{(3R,4R)-4-methyl -1-[3-methyl-4-(3-oxo-morpholin-4-yl)-phenyl]-5-oxo-pyrrolidin-3-yl}-amide
(7) (R)-5-bromo-thiophene-2-carboxylic acid-{1-[2,5-difluoro-4-(3-oxo-morpholin-4-yl)-phenyl]-5-oxo-pyrrolidin-3-yl}-amide
(8) 5-bromo-thiophene-2-carboxylic acid-{1-[3-methyl-4-(5-oxo-[1,4]oxazepan-4-yl)-phenyl]-5-oxo-pyrrolidin-3-yl}-amide
(9)(R)-5-ethynyl-thiophene-2-carboxylic acid-{1-[3-methyl-4-(3-oxo-morpholin-4-yl)-phenyl]-5-oxo-pyrrolidin-3-yl}-amide
(10) 5-ethynyl-thiophene-2-carboxylic acid-{1-[3-methyl-4-(5-oxo-[1,4]oxazepan-4-yl)-phenyl]-5-oxo-pyrrolidin-3-yl}-amide
(11) 5-bromo-thiophene-2-carboxylic acid-{1-[3-methyl-4-(2-oxo-[1,3]oxazepan-3-yl)-phenyl]-5-oxo-pyrrolidin-3-yl}-amide
(12) 5-ethynyl-thiophene-2-carboxylic acid-{(3R,4R)-4-methyl-1-[3-methyl-4-(3-oxo-morphol in-4-yl)-phenyl]-5-oxo-pyrrolidin-3-yl}-amide
(13) (R)-5-bromo-thiophene-2-carboxylic acid-{1-[6-methyl-5-(3-oxo-morpholin-4-yl)-pyridin-2-yl]-5-oxo-pyrroldin-3-yl}-amide
(14) (R)-5-bromo-thiophene-2-carboxylic acid-{1-[4-(3-oxo-morpholin-4-yl)-phenyl]-5-oxo-pyrroldin-3-yl}-amide
(15) (R)-5-ethynyl-thiophene-2-carboxylic acid-{5-oxo-1-[6-methyl-5-(3-oxo-morpholin-4-yl )-pyridin-2-yl]-pyrrolidin-3-yl}-amide
(16) (R)-5-chloro-thiophene-2-carboxylic acid-{1-[6-methyl-5-(3-oxo-morpholin-4-yl)-pyridin-2-yl]-5-oxo-pyrroldin-3-yl}-amide
(17) (R)-5-ethynyl-thiophene-2-carboxylic acid-{5-oxo-1-[4-(3-oxo-morpholin-4-yl)-phenyl]-pyrrolidin-3-yl}-amide
(18) (R)-5-chloro-thiophene-2-carboxylic acid-{5-oxo-1-[4-(3-oxo-morpholin-4-yl )-phenyl]-pyrrolidin-3-yl}-amide
(19) (R)-4-bromo-thiophene-2-carboxylic acid-{1-[5-oxo-4-(3-oxo-morpholin-4-yl)- phenyl]-pyrrolidin-3-yl}-amide
(20) (R)-5-bromo-thiophene-2-carboxylic acid-{5-oxo-1-[4-(2-oxo-piperidin-1-yl )-phenyl]-pyrrolidin-3-yl}-amide
(21) (R)-5-ethynyl-thiophene-2-carboxylic acid-{5-oxo-1-[4-(2-oxo-piperidin-1-yl)-phenyl]-pyrrolidin-3-yl}-amide
(22) (R)-5-bromo-thiophene-2-carboxylic acid-{5-oxo-1-[4-(3-oxo-morpholin-4-yl )-3-trifluoromethyl-phenyl]-pyrrolidin-3-yl}-amide
(23) (R)-4-bromo-thiophene-2-carboxylic acid-{1-[3-methyl-4-(3-oxo-[1,4]oxazepan-4-yl)-phenyl]-5-oxo-pyrrolidin-3-yl}-amide
(24) 5-ethynyl-thiophene-2-carboxylic acid-{1-[3-methyl-4-(5-oxo-[1,4]oxazepan-4-yl)-phenyl]-5-oxo-pyrrolidin-3-yl}-amide
(25) 5-chloro-thiophene-2-carboxylic acid-{1-[3-chloro-4-(2-oxo-azepan-1-yl)-phenyl]-5-oxo-pyrroldin-3-yl}-amide
(26) 5-bromo-thiophene-2-carboxylic acid-{(3R,4S)-4-hydroxy-1-[3-methyl-4-(3-oxo-morpholin-4-yl)-phenyl]-5-oxo-pyrrolidin-3-yl}-amide
(27) 5-bromo-thiophene-2-carboxylic acid-{4-methoxy-1-[3-methyl-4-(3-oxo-morpholin-4-yl)-phenyl]-5-oxo-pyrrolidin-3-yl}-amide,
(28) 5-ethynyl-thiophene-2-carboxylic acid-{4-methoxy-1-[3-methyl-4-(3-oxo-morpholin-4-yl)-phenyl]-5-oxo-pyrrolidin-3-yl}-amide,
(29) 5-bromo-thiophene-2-carboxylic acid-{4-methoxy-1-[3-chloro-4-(3-oxo-morpholin-4-yl)-phenyl]-5-oxo-pyrrolidin-3-yl}-amide,
(30) 5-bromo-thiophene-2-carboxylic acid-{4-methoxy-1-[4-(3-oxo-morpholin-4-yl)-phenyl]-5-oxo-pyrrolidin-3-yl}-amide,
(31) 5-bromo-thiophene-2-carboxylic acid-{1-[3-chloro-4-(3-oxo-morpholin-4-yl)-phenyl]-5-oxo-4-pyridin-3-yl methyl-pyrroldin-3-yl}-amide
(32) 5-bromo-thiophene-2-carboxylic acid-{4-carbamoyl methyl-5-oxo-1-[3-methyl-4-(3-oxo-morpholin-4-yl)-phenyl]-pyrrolidin-3-yl}-amide
(33) 5-bromo-thiophene-2-carboxylic acid-{4-methyl-5-oxo-1-[4-(3-oxo-morpholin-4-yl)-phenyl]-pyrrolidin-3-yl}-amide
(34) 5-bromo-thiophene-2-carboxylic acid-{4-methyl-1-[6-methyl-5-(3-oxo-morpholin-4-yl )-pyridin-2-yl]-5-oxo-pyrroldin-3-yl}-amide
(35) 5-bromo-thiophene-2-carboxylic acid-{4-di methylaminocarbamoylmethyl-3-methyl-1-[3-methyl-4-(3-oxo-morpholin-4-yl)-phenyl]-5-oxo-pyrrolidin-3-yl}-amide,
(36) (R)-5-bromo-thiophene-2-carboxylic acid-{1-[3-chloro-4-(5-oxo-[1,4]oxazepan-4-yl)-phenyl]-5-oxo-pyrrolidin-3-yl}-amide

(37) (R)-5-chloro-thiophene-2-carboxylic acid-{1-[3-methyl-4-(5-oxo-[1,4]oxazepan-4-yl)-phenyl]-5-oxo-pyrrolidin-3-yl}-amide
(38) (R)-5-bromo-thiophene-2-carboxylic acid-{4-methoxy-1-[3-methyl-4-(5-oxo-[1,4]oxazepan-4-yl)-phenyl]-5-oxo-pyrrolidin-3-yl}-amide
(39) (R)-5-bromo-thiophene-2-carboxylic acid-{4-hydroxy-1-[3-methyl-4-(5-oxo-[1,4]oxazepan-4-yl)-phenyl]-5-oxo-pyrrolidin-3-yl}-amide
(40) 5-bromo-thiophene-2-carboxylic acid-{4-ethoxy-1-[3-methyl-4-(5-oxo-[1,4]oxazepan-4-yl)-phenyl]-5-oxo-pyrrolidin-3-yl}-amide
(41) 5-ethynyl-thiophene-2-carboxylic acid-{4-methoxy-1-[3-methyl-4-(5-oxo-[1,4]oxazepan-4-yl)-phenyl]-5-oxo-pyrrolidin-3-yl}-amide
(42) 5-bromo-thiophene-2-carboxylic acid-{4-(2-methoxy-ethoxy)-1-[3-methyl-4-(5-oxo-[1,4]oxazepan-4-yl)-phenyl]-5-oxo-pyrrolidin-3-yl}-amide
(43) 5-bromo-thiophene-2-carboxylic acid-{4-hydroxymethyl-1-[3-methyl-4-(3-oxo-morpholin-4-yl)-phenyl]-5-oxo-pyrrolidin-3-yl}-amide
(44) 5-bromo-thiophene-2-carboxylic acid-{4-methoxymethyl-1-[3-methyl-4-(3-oxo-morpholin-4-yl)-phenyl]-5-oxo-pyrrolidin-3-yl}-amide, and
(45) 5-bromo-thiophene-2-carboxylic acid-{4-(2-hydroxy-ethyl)-1-[3-methyl-4-(3-oxo-morpholin-4-yl)-phenyl]-5-oxo-pyrrolidin-3-yl}-amide, or a tautomer or salt thereof.

10. A physiologically acceptable salt of a compound according to one of claims 1 to 9.

11. A pharmaceutical composition containing a compound according to one of claims 1 to 9 or a physiologically acceptable salt thereof together with one or more inert carriers and/or diluents.

* * * * *